United States Patent
Shively et al.

(10) Patent No.: US 12,043,673 B2
(45) Date of Patent: Jul. 23, 2024

(54) COMPLEMENTARY RNA LINKED BISPECIFIC T-CELL ENGAGING ANTIBODIES

(71) Applicant: City of Hope, Duarte, CA (US)

(72) Inventors: John E. Shively, Duarte, CA (US); Lin Li, Duarte, CA (US); Maciej Kujawski, Duarte, CA (US); Piotr Swiderski, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 218 days.

(21) Appl. No.: 17/503,132

(22) Filed: Oct. 15, 2021

(65) Prior Publication Data

US 2022/0119552 A1    Apr. 21, 2022

Related U.S. Application Data

(60) Provisional application No. 63/092,426, filed on Oct. 15, 2020.

(51) Int. Cl.
| | | |
|---|---|---|
| *C07K 16/00* | (2006.01) | |
| *C07K 16/28* | (2006.01) | |
| *C07K 16/42* | (2006.01) | |
| *C07K 16/46* | (2006.01) | |
| *C07K 19/00* | (2006.01) | |

(52) U.S. Cl.
CPC ........ *C07K 16/4283* (2013.01); *C07K 16/283* (2013.01); *C07K 16/2878* (2013.01); *C07K 16/46* (2013.01); *C07K 2317/24* (2013.01); *C07K 2317/31* (2013.01); *C07K 2317/52* (2013.01)

(58) Field of Classification Search
CPC ..... C07K 2317/31; C07K 19/00; C07K 16/00
See application file for complete search history.

(56) References Cited

U.S. PATENT DOCUMENTS 5,635,602 A * 6/1997 Cantor et al.

FOREIGN PATENT DOCUMENTS

WO    WO2006137932 A2 * 12/2006    ............. H01L 21/00

OTHER PUBLICATIONS

Kujawski et al. (Sep. 5, 2019) "Generation of dual specific bivalent BiTEs (dbBIspecific T-cell engaging antibodies) for cellular immunotherapy" BMC cancer, 19(1), 1-14. (Year: 2019).*
Dovgan, I. et al. (Oct. 16, 2019, e-published Jul. 24, 2019). "Antibody-Oligonucleotide Conjugates as Therapeutic, Imaging, and Detection Agents," *Bioconjug Chem* 30(10):2483-2501.
Kujawski, M. et al. (Sep. 5, 2019). Generation of dual specific bivalent BiTEs (dbBIspecific T-cell engaging antibodies) for cellular immunotherapy, *BMC Cancer* 19(1):882.
Zhu, M. et al. (Oct. 2016). "Blinatumomab, a Bispecific T-cell Engager (BiTE(®)) for CD-19 Targeted Cancer Immunotherapy: Clinical Pharmacology and Its Implications," *Clin Pharmacokinet* 55(10):1271-1288.

* cited by examiner

*Primary Examiner* — James D Schultz
*Assistant Examiner* — James Joseph Graber
(74) *Attorney, Agent, or Firm* — MINTZ, LEVIN, COHN, FERRIS, GLOVSKY AND POPEO, P.C.

(57) ABSTRACT

The compositions and methods provide herein include, inter alia, antibodies attached to single-stranded oligoribonucleotides. Two antibodies are capable of forming complexes in vivo through hybridization of the respective complementary oligoribonucleotides they are bound to. For example, a first antibody bound to a first oligoribonucleotide through a first chemical linker may be administered to a subject, bind to a cell surface antigen in vivo and subsequently form an antibody complex in vivo with a second antibody bound to a second oligoribonucleotide through a second chemical linker, through complementary base-pairing between the first and the second oligoribonucleotide. The compositions and methods provided herein are, inter alia, useful for diagnostic and therapeutic purposes, for example, the treatment of cancer or autoimmune disease.

12 Claims, 41 Drawing Sheets

Specification includes a Sequence Listing.

FIG. 11
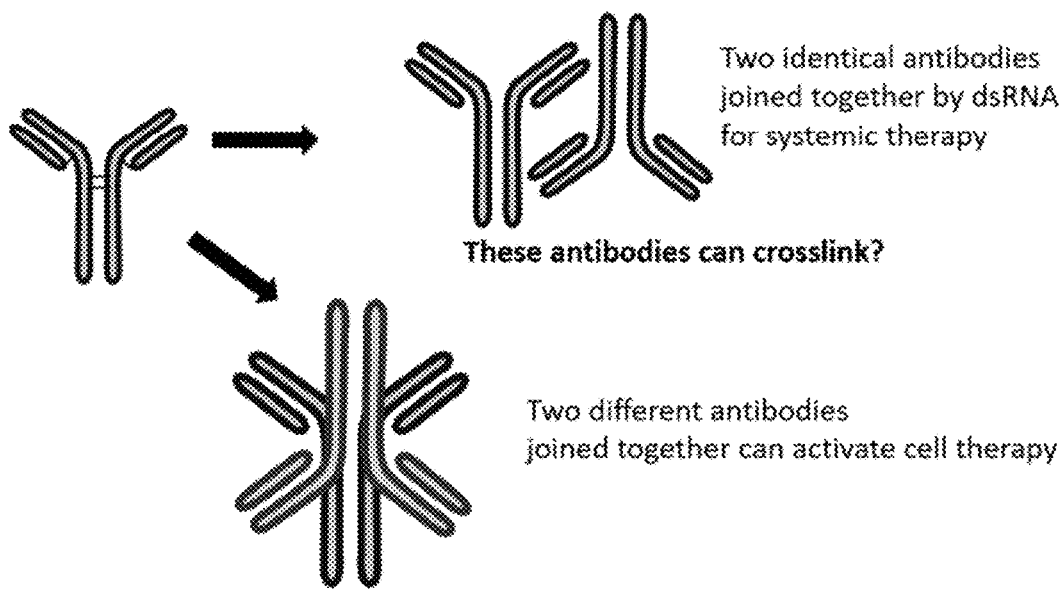
FIG. 12
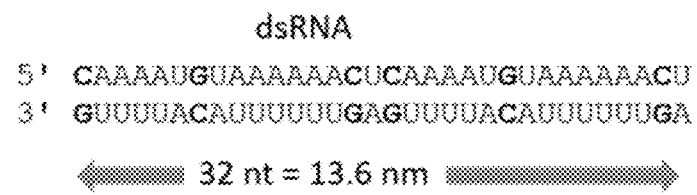
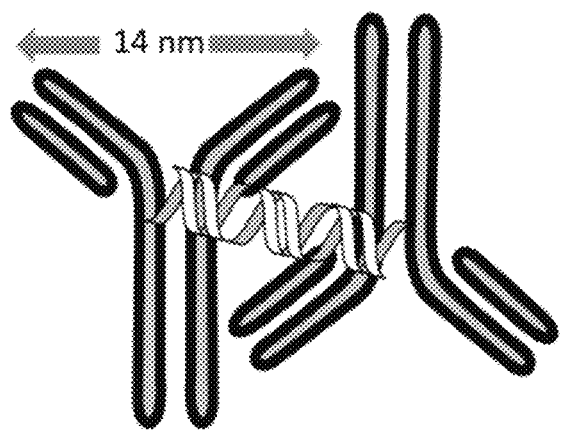

FIG. 14A

Primary Sequence: 5'- CAAAAUGUAAAAAACUCAAAAUGUAAAAAACU -3'
Secondary Sequence: 5'- AGUUUUUUACAUUUUGAGUUUUUUACAUUUUG -3'

Maximum Delta G: -53.94 kcal/mole
Delta G: -53.94 kcal/mole   Base Pairs: 32
5'  CAAAAUGUAAAAAACUCAAAAUGUAAAAAACU
    ||||||||||||||||||||||||||||||||
3'  GUUUUACAUUUUUUGAGUUUUACAUUUUUUGA

FIG. 14B

Delta G: -26.18 kcal/mole   Base Pairs: 16
5'                      CAAAAUGUAAAAAACUCAAAAUGUAAAAAACU
                        ||||||||||||||||
3'  GUUUUACAUUUUUUGAGUUUUACAUUUUUUGA

FIG. 14C

Delta G: -26.18 kcal/mole   Base Pairs: 16
5'  CAAAAUGUAAAAAACUCAAAAUGUAAAAAACU
                        ||||||||||||||||
3'                      GUUUUACAUUUUUUGAGUUUUACAUUUU

|     | OKT3  | dbBiTE | OKT3-oligo | dbBiTER |
|-----|-------|--------|------------|---------|
| 0h  | 93.0% | 94.9%  | 90.8%      | 94.9%   |
| 1h  | 62.8% | 83.1%  | 58.7%      | 93.5%   |
| 3h  | 56.7% | 71.0%  | 39.4%      | 89.8%   |
| 6h  | 56.1% | 71.2%  | 39.0%      | 82.1%   |

FIG. 19E

FIG. 21C
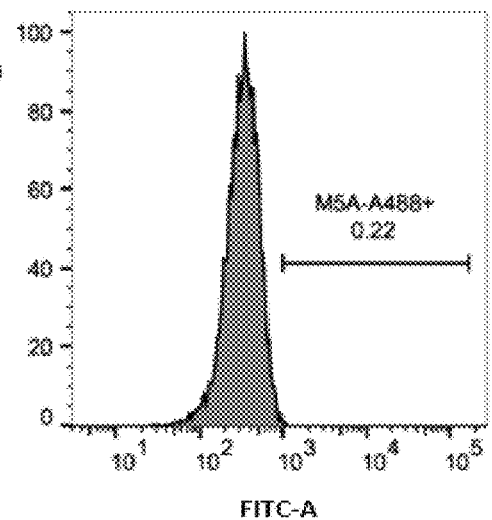
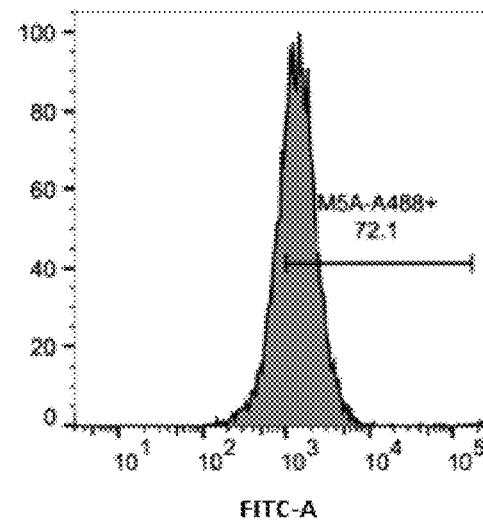
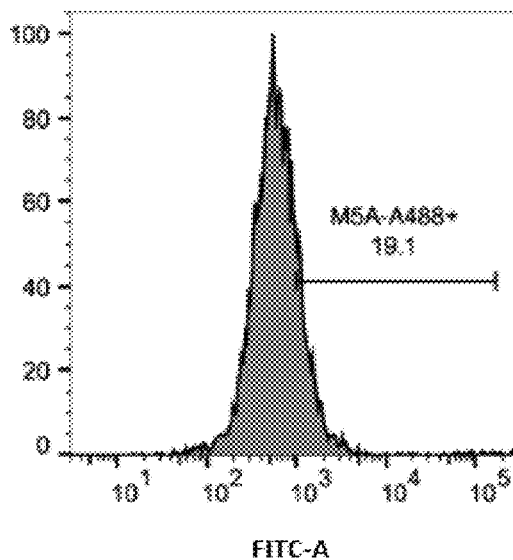
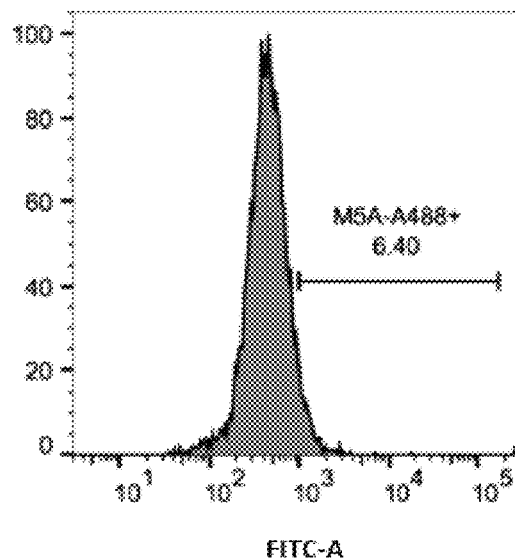

```
                    SEQUENCE LISTING

<160> NUMBER OF SEQ ID NOS: 6

<210> SEQ ID NO 1
<211> LENGTH: 32
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(32)
<223> OTHER INFORMATION: 2' O-Methyl modified base

<400> SEQUENCE: 1
aguuuuuuac auuuugaguu uuuuacauuu ug                            32

<210> SEQ ID NO 2
<211> LENGTH: 32
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(32)
<223> OTHER INFORMATION: 2' O-Methyl modified base

<400> SEQUENCE: 2
caaaauguaa aaacucaaa auguaaaaaa cu                             32

<210> SEQ ID NO 3
<211> LENGTH: 32
<212> TYPE: RNA
<213> ORGANISM: Artificial Sequence
<220> FEATURE:
<223> OTHER INFORMATION: Synthetic polynucleotide

<400> SEQUENCE: 3
caaaauguaa aaacucaaa auguaaaaaa cu                             32

<210> SEQ ID NO 4
<211> LENGTH: 32
<212> TYPE: RNA
<213> ORGANISM: Artificial Sequence
<220> FEATURE:
```

```
<223> OTHER INFORMATION: Synthetic polynucleotide

<400> SEQUENCE: 4
aguuuuuuac auuuugaguu uuuuacauuu ug                              32

<210> SEQ ID NO 5
<211> LENGTH: 32
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(32)
<223> OTHER INFORMATION: 2' O-Methyl modified base

<400> SEQUENCE: 5
auuggauuac agacacuuua cacuuacacu uu                              32

<210> SEQ ID NO 6
<211> LENGTH: 32
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (1)..(32)
<223> OTHER INFORMATION: 2' O-Methyl modified base

<400> SEQUENCE: 6
aaaguguaag uguaaagugu cuguaaucca au                              32
```

COMPLEMENTARY RNA LINKED BISPECIFIC T-CELL ENGAGING ANTIBODIES

CROSS-REFERENCES TO RELATED APPLICATIONS

This application claims the benefit of U.S. Provisional Application No. 63/092,426, filed Oct. 15, 2020, which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-784001US_SequenceListing_ST25.TXT, created on Oct. 15, 2021, and having a size of 4,096 bytes, machine format IBM-PC, MS-Windows operating system, is hereby incorporated by reference.

BACKGROUND

Antibodies have been modified for treatment of diseases, including cancer and autoimmune disorders. However, use of multimer antibody conjugates and multispecific antibodies have been limited by inefficient production methods. Further, previously generated multispecific antibodies lacked flexibility and/or stability, thus preventing their ability to effectively bind target antigens. Disclosed herein, inter alia, are solutions to these and other problems in the art.

BRIEF SUMMARY OF THE INVENTION

In an aspect is provided a pharmaceutical kit including: (i) a first dosage form including a first antibody covalently attached to a first oligoribonucleotide through a first chemical linker and a pharmaceutically acceptable excipient; and (ii) a second dosage form including a second antibody covalently attached to a second oligoribonucleotide through a second chemical linker and a pharmaceutically acceptable excipient.

In an aspect is provided a pharmaceutical composition including a therapeutically effective amount of a cell composition comprising a cell bound to a first antibody covalently attached to a first oligoribonucleotide through a first chemical linker and a pharmaceutically acceptable excipient.

In another aspect a method of treating a disease in a subject in need thereof is provided, the method including administering to a subject a therapeutically effective amount of: (i) a first antibody covalently attached to a first oligoribonucleotide through a first chemical linker; and (ii) a second antibody covalently attached to a second oligoribonucleotide through a second chemical linker.

In an aspect a method of treating a disease in a subject in need thereof is provided, the method including: (i) isolating a cell from a subject, thereby forming an isolated cell; (ii) contacting the isolated cell ex vivo with a first antibody covalently attached to a first oligoribonucleotide through a first chemical linker, thereby forming an antibody cell conjugate; and (iii) administering a therapeutically effective amount of the antibody cell conjugate to the subject.

In an aspect is provided a method of treating a disease in a subject in need thereof, said method including: (i) isolating a cell from the subject, thereby forming an isolated cell; (ii) contacting the isolated cell ex vivo with a first antigen-binding antibody covalently attached to a first oligoribonucleotide through a first chemical linker, thereby forming an antibody cell conjugate; (iii) contacting the antibody cell conjugate ex vivo with a second antibody covalently attached to a second oligoribonucleotide through a second chemical linker, wherein the first oligoribonucleotide and the second oligoribonucleotide hybridize, thereby forming a bispecific antibody cell conjugate; and (iv) administering a therapeutically effective amount of the bispecific antibody cell conjugate to the subject.

BRIEF DESCRIPTION OF THE DRAWINGS

FIG. 2A. shows structures of example 2'-OMe oligoribonucleotide sequences. FIG. 2B. shows a magnified portion of a 5'-end of an 2'-OMe oligoribonucleotide sequence. FIG. 2C. shows a magnified portion of a 3'-end of an 2'-OMe oligoribonucleotide sequence.

FIG. 3A. is chromatogram showing elution of the first oligo on SEC. Tallest, middle and smallest peaks represent eluent detected at 260 nm, 214 nm, and 280 nm, respectively. FIG. 3B. is an SEC chromatogram showing elution of ds RNA formed by mixing of a first oligo with a second complementary oligo. FIG. 3C. is an SEC chromatogram showing presence of RNA in the crosslinked antibody conjugate. DBCO derivatized antibody was mixed to demonstrate crosslinking of antibody to two ends of the dsRNA. The peak at 16.23 min is the cross-linked antibody. The peak at 26.75 min is unreacted antibody. Monitoring at 3 wavelengths demonstrates the presence of RNA in the cross-linked product.

FIG. 5A. Anti-CEA antibody M5A was reduced, reacted with Br-DBCO and 5'azido-2'OMe-oligo-S and purified by SEC. FIG. 5B. Anti-CD3 antibody OKT3 was reacted with Br-DBCO and 5'azido-2'OMe-oligo-S' and purified by SEC. FIG. 5C. The two RNA derivatized antibodies were mixed and purified by SEC. The peak at 26.09 min is unconjugated Abs (150 kDa). The peak at 20.91 min is conjugated bispecific antibody of approximate size 300 kDa. The peak at 18.70 min is a mix of multimers of bispecific antibodies. These peaks were further purified as shown in FIG. 6.

FIG. 6A. Repurification of 18.70 min peak shows it to be largely free of 20.91 min peak. FIG. 6B. Repurification of 20.91 min peak shows removal of 26.09 min peak by substantial contamination with 18.70 min peak.

FIG. 8A. Binding to activated human T cells detected by flow using anti-mouse Alexa Fluor 555 and anti-human Alexa Fluor 647 secondary antibodies. Unstained, secondary antibodies only, OKT3-RNA-S coated shown as controls. FIGS. 8B-8C. Binding to CEA negative (MDA-MB-231) and CEA positive (MDA-MB-231-CEA), respectively, detected by flow using anti-mouse Alexa555 and anti-human Alexa 647 secondary antibodies. Unstained, secondary antibodies only and M5A-RNA-S' shown as controls. FIG. 8D. dbBiTER redirected target cells lysis of CEA expressing cell lines, cytotoxicity measured by GFP fluorescence. OKT3-RNA-S coated T cells used as controls.

FIG. 9A. T cell is first coated with OKT3-RNA-S, then incubated with M5A-RNA-S', and dbBiTER formed on the T cell via duplex formation redirects cytotoxic response against a target cell. The primary sequences of the RNA are SEQ ID NO:3 and 4. FIG. 9B. Binding of OKT3-RNA-S and M5A-RNA-S' to T cells. Detected with anti-human Alexa Fluor 647 labeled secondary antibody and analyzed by flow cytometry. FIG. 9C. Efficiency of duplex formation of second antibody over the range 0-20 μg/mL/$10^7$ cells. Detected with anti-human Alexa Fluor 647 labeled secondary antibody and analyzed by flow cytometry. FIG. 9D. Redirected cytotoxicity of dbBiTER coated T cells on CEA negative vs CEA positive target cells, measured by GFP fluorescence.

FIG. 11. A schematic showing conjugation of identical antibodies or different antibodies. Two different antibodies joined together may localize effector cells and target cells by binding to effector antigens and target antigens. Two identical antibodies joined together may enhance systemic therapy, for example by crosslinking targets.

FIG. 12. A cartoon showing dimensions of an exemplary dsRNA linker and the distance between the antigen binding sites of an antibody. The primary sequences of the RNA are SEQ ID NO:3 and 4.

FIGS. 14A-14C. Complementary RNA sequences used to attach antibodies, and the quantitative measurement of their hybridization. FIG. 14A. The 32-base pair primary (SEQ ID NO:3) and secondary sequences (SEQ ID NO:4) fully hybridized. FIG. 14B. The 16 bases on the 5' end of the primary sequence (SEQ ID NO:3) may hybridize with complementary bases of the secondary sequence (SEQ ID NO:4). FIG. 14C. The 16 bases on the 3' end of the primary sequence (SEQ ID NO:3) may hybridize with complementary bases of the secondary sequence (SEQ ID NO: 4).

FIG. 15A. The structure of the 32-mer JSMK-8721 (SEQ ID NO:1) oligonucleotide derivatized with functional groups. FIG. 15B. A magnified portion of the 5'-end of the sequence. FIG. 15C. A magnified portion of the 3'-end of the sequence.

FIG. 17A. T cell is first coated with DBCO-hOKT3, then incubated with azide-M5A, the click reaction between DBCO and azide occurs, and dbBiTE formed on the T cell redirects cytotoxic response against a target cell. FIG. 17B. Click efficiency of binding of second antibody over the range 0-20 μg/mL/$10^7$ cells. Azide-M5A derivatized with Alexa Fluor 488 was detected by flow cytometry. FIG. 17C. Redirected cytotoxicity of dbBiTE coated T cells on CEA negative vs CEA positive target cells, measured by GFP fluorescence. FIG. 17D. IFNγ production measured by ELISA in media from cytotoxic assay shown in FIG. 17C at E:T ratio 10:1 on CEA negative vs CEA positive target cells.

FIG. 18A. Sequence of RNA oligo-S(SEQ ID NO:3) and S' (SEQ ID NO:4) and their duplex formation. FIG. 18B. Demonstration of oligo-S to oligo S' duplex formation by SEC. FIG. 18C. Quantitation of oligos on two antibodies by hybridization with Alexa Fluor 488 complementary oligos.

FIGS. 19A-19E. Comparison of antibody surface stability of on T cells. Activated T cells coated with: FIG. 19A. anti-CD3 OKT3, FIG. 19B. dbBiTEs, FIG. 19C. anti-CD3 OKT3-RNA-S, and FIG. 19D. on-cell generated dbBiTERs. After coating and washing with PBS, cells were incubated in full media in 37° C. for indicated times followed with secondary antibodies staining (anti-mouse Alexa Fluor 555 in FIGS. 19A and 19C, and anti-human Alexa Fluor 647 in FIGS. 19B and 19D) and detected by flow cytometry. FIG. 19E. Quantification of surface staining.

FIG. 20A. Activated T cells and tumor target cells were coated separately with complementary 2'OMe-RNA-antibodies. RNA sequences used are SEQ ID NO:3 and 4. FIG. 20B. Redirected targets lysis after T cells and target cells were incubated together. Cytotoxicity of MDA-MB-231 transfected CEA cells, measured by GFP fluorescence.

FIGS. 21A-21C. On-cell click reaction kinetics and specificity. FIG. 21A. Cell-click dbBiTE formation on activated T cells after increasing of time of incubation with M5A-azide-Alexa Fluor 488 antibody detected by flow. FIGS. 21B-21C. T cells pre-coated with hOKT-DBCO antibody (FIG. 21B) or uncoated controls (FIG. 21C) incubated with M5A-azide-Alexa Fluor 488 antibody for 2 h and washed once, twice or three times with PBS. A fluorescence for Alexa Fluor 488 remained only on cells pre-coated with hOKT-DBCO antibody.

DETAILED DESCRIPTION

I. Definitions

Figure 1A:
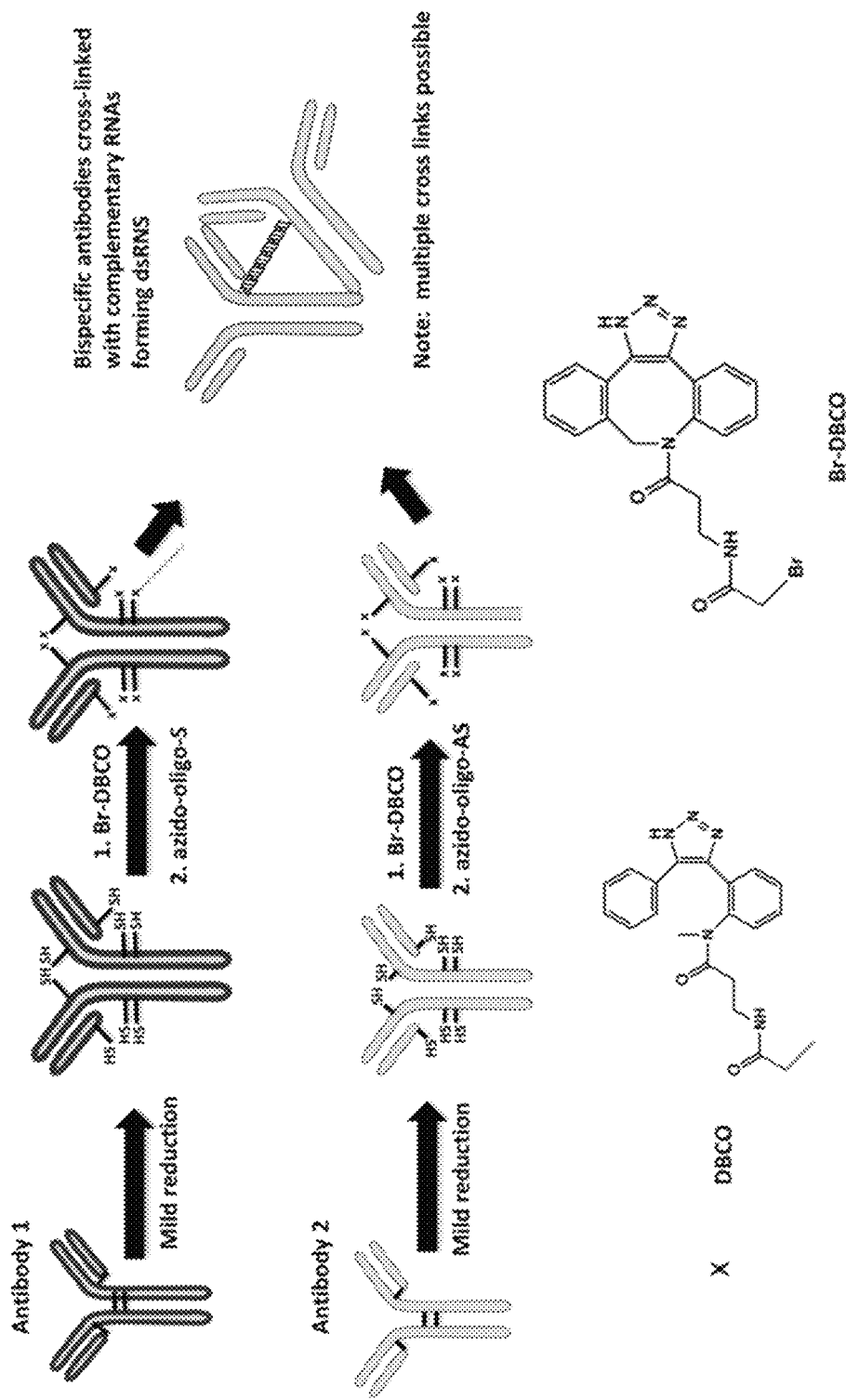
FIGS. 1A-1B. are schematics showing FIG. 1A. the production of antibodies with complementary protected RNAs and FIG. 1B. the formation of a bispecific antibody.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The symbol "$\sim\!\sim\!\sim$" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

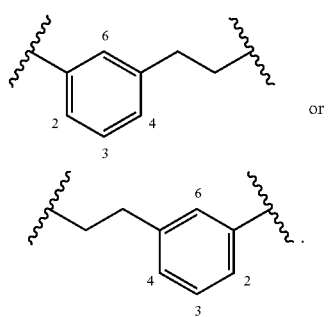

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C (O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —$N_3$, —CH (Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality of R substituents, each of the R-substituents may be differentiated herein using a prime symbol (') such as R', R", etc. For example, where a moiety is $R^{3A}$-substituted or unsubstituted alkyl, and the moiety is substituted with a plurality of $R^{3A}$ substituents, the plurality of $R^{3A}$ substituents may be differentiated as $R^{3A'}$, $R^{3A''}$, $R^{3A'''}$, etc. In some embodiments, the plurality of R substituents is 3.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:
(i) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., $C_1$-$C_5$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo,
halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHC$_{12}$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and
(b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "chemical linker," as provided herein, is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of chemical moieties is chemically different. Alternatively, the chemical linker may be a non-covalent linker. Examples of non-covalent linkers include without limitation, ionic bonds, hydrogen bonds, halogen bonds, van der Waals interactions (e.g. dipole-dipole, dipole-induced dipole, London dispersion), ring stacking (pi effects), and hydrophobic interactions. In embodiments, a chemical linker is formed using conjugate chemistry including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stdckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula —S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded RNA, and hybrid molecules having mixtures of single and double stranded DNA and RNA. Examples of nucleic acids, e.g. polynucleotides, contemplated herein include, but are not limited to, any type of RNA, e.g., mRNA, siRNA, miRNA, sgRNA, and guide RNA and any type of DNA, genomic DNA, plasmid DNA, and minicircle DNA, and any fragments thereof. In embodiments, the nucleic acid is messenger RNA. In embodiments, the messenger RNA is messenger ribonucleoprotein (RNP). The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

As may be used herein, the terms "nucleic acid," "nucleic acid molecule," "nucleic acid oligomer," "oligonucleotide,"

"nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, sgRNA, guide RNA, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235, 033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The nucleic acid compounds described herein may contain chemical modifications, e.g. as defined herein, to enhance their functional characteristics, such as nuclease resistance or binding affinity. The modifications may be present in a nucleic acid compound, a RNA/DNA sequence and/or in a nucleotide-based compound moiety or compound, e.g. a saRNA, siRNA, miRNA, mRNA.

In some cases, modifications may be made to the base, sugar ring, or phosphate group of one or more nucleotides.

In some cases, the nucleic acid compounds described herein comprise one or more modified nucleobases. For example, the nucleic acid compounds may comprise one or more ribo/deoxyribo nucleobases modified with a fluoro (F), amino ($NH_2$) or O-methyl ($OCH_3$) group. In some cases, the nucleobases are modified at the 2' position, the 3' position, the 5' position or the 6' position. In some cases, the nucleic acid compounds may comprise one or more 2'-aminopyrimidines, 2'-fluoropyrimidines, 2'-O-methyl nucleotides and/or 'locked' nucleotides (LNA) (see e.g. Lin, Y et al., *Nucleic Acids Res.* 1994 22, 5229-5234 (1994); Ruckman, J. et al., *J. Biol. Chem.* 1998 273, 20556-20567; Burmeister, P E et al., *Chem. Biol.* 2005 12, 25-33; Kuwahara, M. & Obika, S. *Artif DNA PNA XNA* 2013 4, 39-48; Veedu, R. N. & Wengel, *J. Mol. Biosyst.* 2009 5, 787-792). In some cases, the nucleic acid compounds comprise one or more L-form nucleic acids (see e.g. Maasch, C et al., *Nucleic Acids Symp. Ser. (Oxf.)* 2008 52, 61-62). Other suitable nucleic acid modifications will be apparent to those skilled in the art (see, e.g. Ni S et al., *Int. J. Mol. Sci* 2017 18, 1683, hereby incorporated by reference in its entirety).

The nucleic acid compounds described herein may comprise spacer or linker sequences between the nucleic acid portion and a compound moiety and/or tag. Suitable spacer or linker sequences will be readily apparent to one skilled in the art.

The terms "analog," "nucleobase analog" and the like, in the context of nucleic acid bases refer, in the usual and customary sense, to chemical moieties that can substitute for normal (i.e., physiological) nucleobases (i.e., A, T, G, C and U) in nucleic acids. Nucleobase analogs can be categorized as purine analogs and pyrimidine analogs. Purine analogs have a core purine ring structure which is substituted to form a purine analog. Pyrimidine analogs have a core pyrimidine ring structure which is substituted to form a pyrimidine analog. Substitution may be endocyclic (i.e., within the purine or pyrimidine ring structure) or exocyclic (i.e., attached to the purine or pyrimidine ring structure). Exemplary nucleobase analogs include, but are not limited to: 1,5-dimethyluracil, 1-methyluracil, 2-amino-6-hydroxyaminopurine, 2-aminopurine, 3-methyluracil, 5-(hydroxymethyl)cytosine, 5-bromouracil, 5-carboxycytosine, 5-fluoroorotic acid, 5-fluorouracil, 5-formylcytosine, 5-formyluracil, 6-azathymine, 6-azauracil, 8-azaadenine, 8-azaguanine, N6-carbamoylmethyladenine, N6-hydroxyadenine, allopurinol, hypoxanthine, thiouracil, locked nucleic acid (LNA), 2'-O-alkyl nucleobase, 2'-Fluoro nucleobase, and 2'-OMe nucleobase.

As used herein, locked nucleic acid (LNA) is a modified RNA nucleotide. LNAs are RNA molecules which possess an extra bridge connecting the 2' oxygen and 4' carbon of the ribose moiety. The ribose becomes locked in the 3'-endo (North) conformation. Base stacking and backbone pre-organization are enhanced by the locked ribose conformation. In embodiments, LNA modification has several advantages, including reduced toxicity, lower dosing, higher affinity and efficient targeting.

As used herein the term "nucleobases" refers to the naturally occurring compounds, which form the differentiating component of nucleotides; five bases occur in nature, three of which are common to RNA and DNA (uracil replaces thymine in RNA). Bases are divided into two groups, purines and pyrimidines, based on their chemical structure. Purines are larger, double-ring molecules comprising adenine and guanine, whereas pyrimidines have only a single-ring structure and comprise cytosine and thymine/uracil. Because of the different size of the two types of nucleobases, purines can only base pair with pyrimidines in order to preserve the DNA molecule's constant width. More specifically, the only base pairs that will fit the structure of the particular molecule are adenine-thymine and cytosine-guanine.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the oligoribonucleotide includes a detectable label, as disclosed herein and generally known in the art. In embodiments, the oligoribonucleotide is connected to a detectable label through a chemical linker.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. A nonspecific sequence may be a sequence that does not encode for a functional nucleic acid or protein. In embodiments, a nonspecific sequence is a sequence of a nucleic acid that includes nucleotides randomly attached to each other. In embodiments, a nonspecific sequence does not encode for a biological function. A nonspecific sequence may be referred to as a "scrambled" sequence (e.g., scrambled nucleic acid sequence). A scrambled sequence (e.g., scrambled nucleic acid sequence) may be created by a software tool to create the sequence scramble as negative control for a functional sequence (e.g., nucleic acid sequence). By way of example, a nonspecific sequence (e.g., nucleic acid sequence) is a sequence (e.g., nucleic acid sequence) that does not function as an inhibitory nucleic acid when contacted with a cell or organism.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions (i.e., stringent hybridization conditions).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. One of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al., supra.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 Molecular Cloning: A Laboratory Manual, 18.1-18.88.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may, In embodiments, be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. The following eight groups each contain amino acids that are conservative substitutions for one another: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

For specific proteins described herein, the named protein includes any of the protein's naturally occurring forms, or variants or homologs that maintain the protein activity (e.g., within at least 50%, 80%, 90%, 95%, 96%, 97%, 98%, 99% or 100% activity compared to the native protein). In embodiments, variants or homologs have at least 50%, 55%, 60%, 65%, 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the protein is the protein as identified by its NCBI sequence reference. In embodiments, the protein is the protein as identified by its NCBI sequence reference or functional fragment or homolog thereof.

"CD3" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex. In embodiments, the CD3 protein is substantially identical to the protein identified by the UniProt reference number P04234 or a variant or homolog having substantial identity thereto. In embodiments, the CD3 protein is substantially identical to the protein identified by the UniProt reference number P09693 or a variant or homolog having substantial identity thereto. In embodiments, the CD3 protein is substantially identical to the protein identified by the UniProt reference number P07766 or a variant or homolog having substantial identity thereto.

The term "CD19 protein" or "CD19" as used herein includes any of the recombinant or naturally-occurring forms of B-lymphocyte antigen CD19, also known as CD19 molecule (Cluster of Differentiation 19), B-Lymphocyte Surface Antigen B4, T-Cell Surface Antigen Leu-12 and CVID3, or variants or homologs thereof that maintain CD19 activity (e.g. within at least 50%, 80%, 90%, 95%, 96%, 97%, 98%, 99% or 100% activity compared to CD19). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD19 protein. In embodiments, the CD19 protein is substantially identical to the protein identified by the UniProt reference number P15391 or a variant or homolog having substantial identity thereto.

"CD20" as referred to herein includes any of the recombinant or naturally-occurring forms of CD20, also known as B-lymphocyte antigen CD20, or variants or homologs thereof that maintain CD20 activity (e.g. within at least 50%, 80%, 90%, 95%, 96%, 97%, 98%, 99% or 100% activity compared to CD20). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD20 protein. In embodiments, the CD20 protein is substantially identical to the protein identified by the NCBI reference number GI: 23110987 or a variant or homolog having substantial identity thereto. In embodiments, the CD20 protein is substantially identical to the protein identified by the NCBI reference number GI: 23110989 or a variant or homolog having substantial identity thereto. In embodiments, the CD20 protein is substantially identical to the protein identified by the NCBI reference number GI: 115968 or a variant or homolog having substantial identity thereto.

A "CEA" or "CEA protein" as referred to herein includes any of the recombinant or naturally-occurring forms of Carcinoembryonic antigen (CEA) also known as Carcinoembryonic antigen-related cell adhesion molecule, Meconium antigen 100, CD66e, or variants or homologs thereof that maintain CEA activity (e.g. within at least 50%, 80%, 90%, 95%, 96%, 97%, 98%, 99% or 100% activity compared to CEA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CEA protein. In embodiments, the CEA protein is substantially identical to the protein identified by the UniProt reference number P06731 or a variant or homolog having substantial identity thereto. In embodiments, the CEA protein is substantially identical to the protein identified by the UniProt reference number P31997 or a variant or homolog having substantial identity thereto. In embodiments, the CEA protein is substantially identical to the protein identified by the UniProt reference number P40918 or a variant or homolog having substantial identity thereto.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the NCBI sequence reference GI:83700231, homolog or functional fragment thereof.

The term "EGFR protein" or "EGFR" as used herein includes any of the recombinant or naturally-occurring forms of epidermal growth factor receptor (EGFR) also known as ErbB-1 or HER1 in humans, or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the EGFR protein is substantially identical to the protein identified by the NCBI reference number GI: 110002567 or a variant or homolog having substantial identity thereto. In embodiments, the EGFR protein is substantially identical to the protein identified by the NCBI reference number GI: 2811086 or a variant or homolog having substantial identity thereto. In embodiments, the EGFR protein is substantially identical to the protein identified by the NCBI reference number GI: 63101670 or a variant or homolog having substantial identity thereto.

The term "Her2 protein" or "Her2" as used herein includes any of the recombinant or naturally-occurring forms of Receptor tyrosine-protein kinase erbB-2, also known as CD340 (cluster of differentiation 340), proto-oncogene Neu, Erbb2 (rodent), or ERBB2 (human), or variants or homologs thereof that maintain Her2 activity (e.g. within at least 50%, 80%, 90%, 95%, 96%, 97%, 98%, 99% or 100% activity compared to Her2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Her2 protein. In embodiments, the Her2 protein is substantially identical to the protein identified by the UniProt reference number P04626 or a variant or homolog having substantial identity thereto.

A "PD-1 protein" or "PD-1" as referred to herein includes any of the recombinant or naturally-occurring forms of the Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto. In embodiments, the PD-1 protein is substantially identical to the protein identified by the UniProt reference number Q02242 or a variant or homolog having substantial identity thereto.

A "PD-L1" or "PD-L1 protein" as referred to herein includes any of the recombinant or naturally-occurring forms of programmed death ligand 1 (PD-L1) also known as cluster of differentiation 274 (CD 274) or variants or homologs thereof that maintain PD-L1 activity (e.g. within at least 50%, 80%, 90%, 95%, 96%, 97%, 98%, 99% or 100% activity compared to PD-L1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-L1 protein. In embodiments, the PD-L1 protein is substantially identical to the protein identified by the UniProt reference number Q9NZQ7 or a variant or homolog having substantial identity thereto.

The term "PSMA" or "PSMA protease" as provided herein includes any of the recombinant or naturally-occurring forms of the prostate-specific membrane antigen (PSMA), also known as glutamate carboxypeptidase II (GCPII), N-acetyl-L-aspartyl-L-glutamate peptidase I (NAALADase I) or NAAG peptidase, or variants or homologs thereof that maintain PSMA activity (e.g. within at least 50%, 80%, 90%, 95%, 96%, 97%, 98%, 99% or 100% activity compared to PSMA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PSMA polypeptide. In embodiments, PSMA is the protein as identified by the NCBI sequence reference GI:62548858, homolog or functional fragment thereof.

The term "PSCA" or "PSCA protein" as provided herein includes any of the recombinant or naturally-occurring forms of the prostate-stem cell antigen (PSCA), or variants or homologs thereof that maintain PSCA activity (e.g. within at least 50%, 80%, 90%, 95%, 96%, 97%, 98%, 99% or 100% activity compared to PSCA). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PSCA polypeptide. In embodiments, PSCA is the protein as identified by the UniProt reference number 043653 or a variant or homolog having substantial identity thereto.

"Tumor-associated glycoprotein 72" (TAG-72) as referred to herein includes any of the recombinant or naturally-occurring forms of TAG-72, or variants or homologs thereof that maintain TAG-72 activity (e.g. within at least 50%, 80%, 90%, 95%, 96%, 97%, 98%, 99% or 100% activity compared to TAG-72). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring TAG-72 protein. In embodiments, the TAG-72 protein is substantially identical to the protein in Sheer et al., Cancer Research 48, 6811-6818 (1988), Johnson et al., Cancer Res. 46(2):850-857 (1986), Ponnusamy et al., Cancer Lett. 28; 251(2):247-257 (2007), or Kostakoglu, L. Cancer Invest. 12(6):551-558 (1994).

The term "VEGFR" or "VEGFR protein" as provided herein includes any of the recombinant or naturally-occurring forms of the Vascular endothelial growth factor receptor (VEGFR), also known as Fms-like tyrosine kinase 1, Tyrosine-protein kinase FRT, Vascular permeability factor receptor, or variants or homologs thereof that maintain VEGFR activity (e.g. within at least 50%, 80%, 90%, 95%, 96%, 97%, 98%, 99% or 100% activity compared to VEGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring VEGFR polypeptide. In embodiments, VEGFR is the protein as identified by the UniProt reference number P17948 or a variant or homolog having substantial identity thereto. In embodiments, VEGFR is the protein as identified by the UniProt reference number P35968 or a variant or homolog having substantial identity thereto. In embodiments, VEGFR is the protein as identified by the UniProt reference number P35916 or a variant or homolog having substantial identity thereto.

The term "CD27" or "CD27 protein" as provided herein includes any of the recombinant or naturally-occurring forms of the CD27 antigen (CD27), also known as CD27L receptor, T-cell activation antigen CD27, Tumor necrosis factor receptor superfamily member 7, or variants or homologs thereof that maintain CD27 protein activity (e.g. within at least 50%, 80%, 90%, 95%, 96%, 97%, 98%, 99% or 100% activity compared to CD27). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD27 polypeptide. In embodiments, CD27 is the protein as identified by the UniProt reference number P26842 or a variant or homolog having substantial identity thereto.

The term "MOG" or "MOG protein" as provided herein includes any of the recombinant or naturally-occurring forms of the Myelin-oligodendrocyte glycoprotein (MOG), or variants or homologs thereof that maintain MOG protein activity (e.g. within at least 50%, 80%, 90%, 95%, 96%, 97%, 98%, 99% or 100% activity compared to MOG). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MOG polypeptide. In embodiments, MOG is the protein as identified by the UniProt reference number Q16653 or a variant or homolog having substantial identity thereto.

The term "peptidylarginine deiminase" or "peptidylarginine deiminase protein" as provided herein includes any of the recombinant or naturally-occurring forms of the peptidylarginine deiminase protein, also known as HL-60 PAD, or variants or homologs thereof that maintain peptidylarginine deiminase protein activity (e.g. within at least 50%, 80%, 90%, 95%, 96%, 97%, 98%, 99% or 100% activity compared to peptidylarginine deiminase). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring peptidylarginine deiminase polypeptide. In embodiments, peptidylarginine deiminase is the protein as identified by the UniProt reference number Q9UM07 or a variant or homolog having substantial identity thereto.

The term "GAD65" or "GAD65 protein" as provided herein includes any of the recombinant or naturally-occurring forms of the glutamic acid decarboxylase protein (GAD65), also known as 65 kDa glutamic acid decarboxylase, or variants or homologs thereof that maintain GAD65 protein activity (e.g. within at least 50%, 80%, 90%, 95%, 96%, 97%, 98%, 99% or 100% activity compared to GAD65). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring GAD65 polypeptide. In embodiments, GAD65 is the protein as identified by the UniProt reference number Q05329 or a variant or homolog having substantial identity thereto.

The term "insulin" or "insulin protein" as provided herein includes any of the recombinant or naturally-occurring forms of the insulin protein, or variants or homologs thereof that maintain insulin protein activity (e.g. within at least 50%, 80%, 90%, 95%, 96%, 97%, 98%, 99% or 100% activity compared to insulin). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring insulin polypeptide. In embodiments, insulin is the protein as identified by the UniProt reference number P01308 or a variant or homolog having substantial identity thereto.

The term "endomysium" or "endomysium protein" as provided herein includes any of the recombinant or naturally-occurring forms of the endomysium protein, also known as titin, connectin, Rhabdomyosarcoma antigen, or variants or homologs thereof that maintain endomysium protein activity (e.g. within at least 50%, 80%, 90%, 95%, 96%, 97%, 98%, 99% or 100% activity compared to endomysium). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring endomysium polypeptide. In embodiments, endomysium is the protein as identified by the UniProt reference number Q8WZ42 or a variant or homolog having substantial identity thereto.

The term "transglutaminase 2" or "transglutaminase 2 protein" as provided herein includes any of the recombinant or naturally-occurring forms of the transglutaminase 2 protein, also known as Protein-glutamine gamma-glutamyltransferase 2, Tissue transglutaminase, Transglutaminase C, or variants or homologs thereof that maintain endomysium protein activity (e.g. within at least 50%, 80%, 90%, 95%, 96%, 97%, 98%, 99% or 100% activity compared to transglutaminase 2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring transglutaminase 2 polypeptide. In embodiments, transglutaminase 2 is the protein as identified by the UniProt reference number P21980 or a variant or homolog having substantial identity thereto.

The term "IgE" or "IgE protein" as provided herein includes any of the recombinant or naturally-occurring forms of the immunoglobulin eplison (IgE) protein, or variants or homologs thereof that maintain IgE protein activity (e.g. within at least 50%, 80%, 90%, 95%, 96%, 97%, 98%, 99% or 100% activity compared to IgE). In some aspects, the variants or homologs have at least 90%, 95%, 96%, 97%, 98%, 99% or 100% amino acid sequence identity across the whole sequence or a portion of the sequence (e.g.

a 50, 100, 150 or 200 continuous amino acid portion) compared to a naturally occurring IgE polypeptide. In embodiments, IgE is the protein as identified by the UniProt reference number P01854 or a variant or homolog having substantial identity thereto. In embodiments, IgE is the protein as identified by the UniProt reference number P23083 or a variant or homolog having substantial identity thereto.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

The Fc (i.e. fragment crystallizable region) is used herein according to its plain and ordinary meaning in the art and refers to the "base" or "tail" of an immunoglobulin and is typically composed of two heavy chains that contribute two or three constant domains depending on the class of the antibody. For example, in IgG, IgA and IgD antibody isotypes, the Fc region may be composed of two identical protein fragments, derived from the second and third constant domains of the antibody's two heavy chains. IgM and IgE Fc regions may contain three heavy chain constant domains (CH domains 2-4) in each polypeptide chain. In embodiments, the Fc region ensures that each antibody generates an appropriate immune response for a given antigen by binding to specific proteins. In embodiments, the Fc region binds to various cell receptors, such as Fc receptors, and other immune molecules, such as complement proteins.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. VH refers to the variable region of the heavy chain. VL refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain (VH or VL) typically has three CDRs identified as CDR1, CDR2 and CDR3. The CDRs of VH are also referred to herein as CDR H1, CDR H2 and CDR H3, respectively, wherein CDR H1 corresponds to CDR 1 of VH, CDR H2 corresponds to CDR 2 of VH and CDR H3 corresponds to CDR 3 of VH. Likewise, the CDRs of VL are referred to herein as CDR L1, CDR L2 and CDR L3, respectively, wherein CDR L1 corresponds to CDR 1 of VL, CDR L2 corresponds to CDR 2 of VL and CDR L3 corresponds to CDR 3 of VL.

The CDRs of the variable region of the light chain are further referred to herein as LCDR1, LCDR2 and LCDR3, respectively, wherein LCDR1 corresponds to CDR 1 of VL, LCDR 2 corresponds to CDR 2 of VL and LCDR 3 corresponds to CDR 3 of VL. Likewise, the CDRs of the variable region of the heavy chain are further referred to herein as HCDR1, HCDR2 and HCDR3, respectively, wherein HCDR1 corresponds to CDR 1 of VH, HCDR 2 corresponds to CDR 2 of VH and HCDR 3 corresponds to CDR 3 of VH.

In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). The present invention is not limited to FRs and CDRs as defined by the Kabat numbering system, but includes all numbering systems, including the canonical numbering system or of Chothia and Lesk J. Mol. Biol. 196: 901-917, 1987; Chothia et al., Nature 342: 877-883, 1989; and/or Al-Lazikani et al., J. Mol. Biol. 273: 927-948, 1997; the numbering system of Honnegher and Plükthun J. Mol. Biol. 309: 657-670, 2001; or the IMGT system discussed in Giudicelli et al., Nucleic Acids Res. 25: 206-211 1997. In one example, the CDRs are defined according to the Kabat numbering system.

"Framework regions" (FRs) are those variable region residues other than the CDR residues. The FRs of VH are also referred to herein as FR H1, FR H2, FR H3 and FR H4, respectively, wherein FR H1 corresponds to FR 1 of VH, FR H2 corresponds to FR 2 of VH, FR H3 corresponds to FR 3 of VH and FR H4 corresponds to FR 4 of VH. Likewise, the FRs of the variable region of the heavy chain are further referred to herein as HFR1, HFR2, HFR3 and HFR4, respectively, wherein HFR1 corresponds to FR 1 of VH, HFR 2 corresponds to FR 2 of VH, HFR 3 corresponds to FR 3 of VH and HFR 4 corresponds to FR 4 of VH.

Likewise, the FRs of VL are referred to herein as FR L1, FR L2, FR L3 and FR L4, respectively, wherein FR L1 corresponds to FR 1 of VL, FR L2 corresponds to FR 2 of VL, FR L3 corresponds to FR 3 of VL and FR L4 corresponds to FR 4 of VL. Likewise, the FRs of the variable region of the light chain are further referred to herein as LFR1, LFR2, LFR3 and LFR4, respectively, wherein LFR1 corresponds to FR 1 of VL, LFR 2 corresponds to FR 2 of VL, LFR 3 corresponds to FR 3 of VL and LFR 4 corresponds to FR 4 of VL.

The term "antigen" as provided herein refers to molecules capable of binding to the antibody binding site, wherein the binding site is not a non-CDR peptide binding region.

The term "effector antigen" as provided herein refers to a molecule on an effector cell which is capable of binding to an effector antigen-binding antibody. For example, an effector antigen may be on a peripheral blood mononuclear cell (PBMC), a B-cell, a T-cell, a natural killer (Nk) cell, a monocyte, a neutrophil, a platelet or a red blood cell.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

The "hinge" or "hinge region" refers to a flexible amino acid stretch between the $C_H1$ and $C_H2$ heavy chains of an antibody, which typically links the two chains by disulfide bonds. The hinge may usually be rich in cysteine and proline amino acid residues. In embodiments, the disulfide bonds in the hinge may be reduced by a reducing agents, for example tris(2-carboxyethyl)phosphine (TCEP) or Dithiothreitol (DTT). In embodiments, the reduced cysteine residues in the hinge may be conjugated to a chemical moiety including a click chemistry reactive functional group. For example, the chemical moiety may be bromoacetamido-dibenzoazacyclooctyne (DBCO) or bromoacetamido-(ethylene glycol)$_n$-amido-DBCO. In embodiments, the reduced cysteine may be apart of a reactive chemical group side chain.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{2}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically. Replication-incompetent viral vectors or replication-defective viral vectors refer to viral vectors that are capable of infecting their target cells and delivering their viral payload, but then fail to continue the typical lytic pathway that leads to cell lysis and death.

The terms "transfection", "transduction", "transfecting" or "transducing" can be used interchangeably and are defined as a process of introducing a nucleic acid molecule and/or a protein to a cell. Nucleic acids may be introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include nanoparticle encapsulation of the nucleic acids that encode the fusion protein (e.g., lipid nanoparticles, gold nanoparticles, and the like), calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) Gene Therapy 8:1-4 and Prochiantz (2007) Nat. Methods 4:119-20.

"Contacting" is used in accordance with its plain ordinary meaning and refers to the process of allowing at least two distinct species to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a fusion protein as provided herein and a nucleic acid sequence (e.g., target DNA sequence).

The terms "bind" and "bound" as used herein is used in accordance with its plain and ordinary meaning and refers to the association between atoms or molecules. The association can be direct or indirect. For example, bound atoms or molecules may be bound, e.g., by covalent bond, linker (e.g. a first linker or second linker), or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a NF-κB, a Toll-like receptor protein). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As defined herein, the term "inhibition", "inhibit", "inhibiting," "repression," repressing," "silencing," "silence" and the like when used in reference to a composition as provided herein (e.g., fusion protein, complex, nucleic acid, vector) refer to negatively affecting (e.g., decreasing) the activity (e.g., transcription) of a nucleic acid sequence (e.g., decreasing transcription of a gene) relative to the activity of the nuclei acid sequence (e.g., transcription of a gene) in the absence of the composition (e.g., fusion protein, complex, nucleic acid, vector). In embodiments, inhibition refers to reduction of a disease or symptoms of disease (e.g., cancer). Thus, inhibition includes, at least in part, partially or totally blocking activation (e.g., transcription), or decreasing, preventing, or delaying activation (e.g., transcription) of the nucleic acid sequence. The inhibited activity (e.g., transcription) may be 90%, 80%, 70%, 60%, 50%, 40%, 30%, 20%, 10%, or less than that in a control. In embodiments, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma (Mantel cell lymphoma), head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (e.g., Mantel cell lymphoma, follicular lymphoma, diffuse large B-cell lymphoma, marginal zona lymphoma, Burkitt's lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia (e.g., lymphoblastic leukemia, chronic lymphocytic leukemia, hairy cell leukemia), acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, the term "tumor marker" refers to molecules present in higher levels in biological samples (i.e. blood, tissue, etc.) from subjects with cancer compared to subjects without cancer. A tumor marker may be a molecule on a cancer cell, which is produced in larger amounts by the cancer cell than a non-cancer cell. For example, a tumor marker may allow for diagnosis of cancer. A tumor marker may allow for identification or isolation of a cancer cell. A tumor marker may allow targeting of a tumor cell, for example by an antibody specific for said tumor marker.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The term "viral infection" or "viral disease" refers to a disease or condition that is caused by a virus. Non-limiting examples of viral infections include human immunodeficiency virus infection (HIV)/acquired immunodeficiency syndrome (AIDS) (e.g. human immunodeficiency virus), hepatic viral diseases (e.g., hepatitis A, B, C, D, E), herpes virus infection (e.g., HSV-1, HSV-2, herpes zoster), flavivirus infection, Zika virus infection, cytomegalovirus infection, a respiratory viral infetion (e.g., adenovirus infection, influenza, severe acute respiratory syndrome, coronavirus infection (e.g., SARS-CoV-1, SARS-CoV-2, MERS-CoV, COVID-19, MERS)), a gastrointestinal viral infection (e.g., norovirus infection, rotavirus infection, astrovirus infection), an exanthematous viral infection (e.g., measles, shingles, smallpox, rubella), viral hemorrhagic disease (e.g., Ebola, Lassa fever, dengue fever, yellow fever), a neurologic viral infection (e.g., West Nile viral infection, polio, viral meningitis, viral encephalitis, Japanese enchephalitis, rabies), and human papilloma viral infection.

The term "associated" or "associated with" in the context of a substance or substance activity or function associated with a disease (e.g., cancer (e.g. leukemia, lymphoma, B cell lymphoma, or multiple myeloma)) means that the disease (e.g. cancer, (e.g. leukemia, lymphoma, B cell lymphoma, or multiple myeloma)) is caused by (in whole or in part), or a symptom of the disease is caused by (in whole or in part) the substance or substance activity or function.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia lymphoblastic leukemia, chronic lymphocytic leukemia, hairy cell leukemia cancer cell), lymphoma (e.g., mantle cell lymphoma (MCL), follicular lymphoma, diffuse large B-cell lymphoma, marginal zone lymphoma, Burkitt's lymphoma), head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and may depend on the route of administration. For example, a dosage form can be in a liquid form for nebulization, e.g., for inhalants, in a tablet or liquid, e.g., for oral delivery, or a saline solution, e.g., for injection.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and Remington: *The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Formulations suitable for oral administration can consist of (a) liquid solutions, such as an effective amount of the antibodies provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administration contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like, that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present invention can also be delivered as nanoparticles.

II. Kits

Provided herein are, inter alia, compositions and methods of use of bi- or multispecific antibody complexes for therapeutic or diagnostic purposes, for example, treatment of cancer and autoimmune diseases. The bi- or multispecific antibody complexes include antibodies bound to each other through complementary oligoribonucleotides. Surprisingly, the complexes may be formed in vivo in a subject due to the unexpected stability of the single-stranded oligoribonucleotide attached to the antibody. For example, a first antibody bound to a first oligoribonucleotide through a first chemical linker may be bound to a cell surface antigen in vivo. Upon administration of a second antibody bound to a second oligoribonucleotide through a second chemical linker, complementary base-pairing between the first and the second oligoribonucleotide occurs in vivo and the first and second antibody are bound to each other to form a bispecific complex in vivo. Similarly, a first antibody attached to a first oligoribonucleotide through a first chemical linker may bind an antigen on a cell in vitro, thereby forming an antibody-cell complex. That antibody-cell complex may be administered to a subject in need thereof and bind a second antibody bound to a second oligoribonucleotide through a second chemical linker in vivo through complementary base-pairing between the first and the second oligoribonucleotide. The compositions and methods provided herein may be used to bind, inter alia, a T-cell antigen (e.g., CD3) using a first antibody attached to a first oligoribonucleotide through a first chemical linker. The complex formed by the T cell (e.g., Nk cell) and the first antibody may be formed in vivo and through administration of a second antibody specific for a cancer antigen (e.g., CEA) which is attached to a second oligoribonucleotide through a second chemical linker, the first and the second oligoribonucleotide hybridize and the T cell is targeted to a CEA-positive cancer cell. The antigens bound by the compositions provided herein may be cancer antigens, autoimmune disease antigens or viral antigens.

In an aspect is provided a pharmaceutical kit including: (i) a first dosage form including a first antibody covalently attached to a first oligoribonucleotide through a first chemical linker and a pharmaceutically acceptable excipient; and (ii) a second dosage form including a second antibody covalently attached to a second oligoribonucleotide through a second chemical linker and a pharmaceutically acceptable excipient. A "first dosage form" as provided herein refers to a discrete composition of a first antibody and is separate from other dosage forms (e.g., the second dosage form of the second antibody). In embodiments, the first dosage form does not include any other active agents. In embodiments, the first dosage form does not include any other therapeutic agent. In embodiments, the first dosage form does not include any other antibody. Likewise, a "second dosage form" as provided herein refers to a discrete composition of the second antibody and is separate from other dosage forms (e.g., the first dosage form of the first antibody). In embodiments, the second dosage form does not include any other active agents. In embodiments, the second dosage form does not include any other therapeutic agent. In embodiments, the second dosage form does not include any other antibody.

In embodiments, the first antibody is an effector antigen-binding antibody. In embodiments, the effector antigen is an autologous antigen. An autologous antigen as provided herein refers to a polypeptide that is expressed by a cell of an organism, wherein the polypeptide originates from that same organism and not from another organism. In embodiments, an autologous antigen is an antigen expressed by an autologous immune cell. An effector antigen as provided herein refers to an antigen expressed by an effector cell. An effector cell as provided herein is a cell capable of directly (e.g., through binding) or indirectly (through expression of soluble proteins such as growth factors or cytokines) modify growth or activity of another cell. In embodiments, the effector antigen is a peripheral blood mononuclear cell (PBMC) antigen, a B-cell antigen, a T-cell antigen, a natural killer (Nk) cell antigen, a monocyte antigen, a neutrophil antigen, a platelet antigen or a red blood cell antigen. In embodiments, the effector antigen is a PBMC antigen. In embodiments, the effector antigen is a B-cell antigen. In embodiments, the effector antigen is a T-cell antigen. In embodiments, the effector antigen is a Nk cell antigen. In embodiments, the effector antigen is a monocyte antigen. In embodiments, the effector antigen is a neutrophil antigen. In embodiments, the effector antigen is a neutrophil antigen. In embodiments, the effector antigen is a platelet antigen. In embodiments, the effector antigen is a red blood cell antigen.

In embodiments, the effector antigen is CD45, CD3, CD25, CD4, CD8, CD69, PD1, CTLA4, Tim3, LAG3, CEACAM1, CD122, CD132, CD56, CD16, NKG2D, CD94, CD158, CD19, CD20, CD40, CD38, IgM, TLR4, CD14, CD11b, CD44, CD55, CD48, CD31, CD63, CD42b, CD36, CD47, or CD71. In embodiments, the effector antigen is CD45. In embodiments, the effector antigen is CD3. In embodiments, the effector antigen is CD25. In embodiments, the effector antigen is CD4. In embodiments, the effector antigen is CD8. In embodiments, the effector antigen is CD69. In embodiments, the effector antigen is PD1. In embodiments, the effector antigen is CTLA4. In embodiments, the effector antigen is Tim3. In embodiments, the effector antigen is LAG3. In embodiments, the effector antigen is CEACAM1. In embodiments, the effector antigen is CD122. In embodiments, the effector antigen is CD132. In embodiments, the effector antigen is CD56. In embodiments, the effector antigen is CD16. In embodiments, the effector antigen is NKG2D. In embodiments, the effector antigen is CD94. In embodiments, the effector antigen is CD158. In embodiments, the effector antigen is CD19. In embodiments, the effector antigen is CD20. In embodiments, the effector antigen is CD40. In embodiments, the effector antigen is CD38. In embodiments, the effector antigen is IgM. In embodiments, the effector antigen is TLR4. In embodiments, the effector antigen is CD14. In embodiments, the effector antigen is CD11b. In embodiments, the effector antigen is CD44. In embodiments, the effector antigen is CD55. In embodiments, the effector antigen is CD48. In embodiments, the effector antigen is CD31. In embodiments, the effector antigen is CD63. In embodiments, the effector antigen is CD42b. In embodiments, the effector antigen is CD36. In embodiments, the effector antigen is CD47. In embodiments, the effector antigen is CD71. In embodiments, the effector antigen is a human effector antigen.

In embodiments, the second antibody is a target antigen-binding antibody. In embodiments, the target antigen is a cancer antigen, a viral antigen or an autoimmune disease antigen. In embodiments, the target antigen is a cancer antigen. In embodiments, the target antigen is a viral antigen. In embodiments, the target antigen is an autoimmune disease antigen.

In embodiments, the target antigen is carcinoembryonic antigen (CEA), TAG72, Her2, EGFR, PSMA, PSCA, PD-L1, or VEGFR. In embodiments, the target antigen is CEA. In embodiments, the target antigen is TAG-72. In embodiments, the target antigen is Her2. In embodiments, the target antigen is EGFR. In embodiments, the target antigen is PSMA. In embodiments, the target antigen is PSCA. In embodiments, the target antigen is PD-L1. In embodiments, the target antigen is VEGFR. In embodiments, the target antigen is a tumor marker.

The compositions and methods provided herein may, inter alia, be used for the treatment of autoimmune disease. Thus, in embodiments, the target antigen is a multiple sclerosis antigen, a rheumatoid arthritis antigen, or a type I diabetes antigen. In embodiments, the target antigen is a multiple sclerosis antigen. In embodiments, the target antigen is a rheumatoid arthritis antigen. In embodiments, the target antigen is a type I diabetes antigen.

In embodiments, the target antigen is CD27, IgE, myelin oligodendrocyte glycoprotein (MOG), peptidylarginine deiminase, glutamic acid decarboxylase (GAD65), insulin, endomysium or transglutaminase 2. In embodiments, the target antigen is CD27. In embodiments, the target antigen is IgE. In embodiments, the target antigen is MOG. In embodiments, the target antigen is peptidylarginine deiminase. In embodiments, the target antigen is GAD65. In embodiments, the target antigen is insulin. In embodiments, the target antigen is endomysium. In embodiments, the target antigen is transglutaminase 2.

In embodiments, the first or second dosage form includes more than one antibody, wherein each of the more than one antibodies is different. In embodiments, each of the more than one antibodies binds a different antigen or a different epitope. In embodiments, the first or second dosage form includes more than one antibody and the antibodies are different (binding different antigens or epitopes). Thus, the first or second dosage form may include multiple types of antibodies. A type of antibody binds a specific antigen or a specific epitope of an antigen. Thus, antibodies of one type bind the same antigen or the same epitope of an antigen. In embodiments, the first or second dosage form includes a single antibody type. Where the first or second dosage form includes a single antibody type there is no other antibody type present in the first or second dosage form. In embodiments, the first or second dosage form includes more than one (e.g., 2, 3, 4, 5, 6, etc.) antibody type. Where the first or second dosage form includes more than one antibody type there are at least two antibody types present in the first or second dosage form.

In embodiments, the first or second dosage form includes a first antibody type, a second antibody type and/or a third antibody type. The first, second and third antibody type may be independently different (i.e., bind a different antigen or epitope). Thus, the first or second dosage form may include a first antibody, a second antibody and/or a third antibody, wherein the first antibody is different (binds a different antigen or epitope) from the second and the third antibody, and the second antibody is different from the third antibody. Therefore, a person having ordinary skill in the art will immediately recognize that the terms "antibody" and "antibody type(s)" have the same meaning and can be used interchangeably. In embodiments, the first or second dosage form includes more than one antibody type and each antibody type is present in a specific amount (specific effective amount, specific therapeutic amount). Thus, the first or second dosage form may include a first amount of a first antibody type, a second amount of a second antibody type and a third amount of a third antibody type and the first, second and third amount may be different or the same. In embodiments, the first, second and third amount are a combined therapeutically effective amount. In embodiments, the first, second and third amount are a combined therapeutically effective amount. In embodiments, the first, second and third amount are a combined synergistic amount.

In embodiments, the first dosage form includes more than one antibody type and the antibodies of the first dosage form are not bound to each other. In embodiments, the first dosage form includes a single antibody type and the antibodies of the single antibody type are not bound to each other. In embodiments, the second dosage form includes more than one antibody type and the antibodies of the second dosage form are not bound to each other. In embodiments, the second dosage form includes a single antibody type and the antibodies of the single antibody type are not bound to each other.

In embodiments, the first dosage form includes more than one antibody, wherein each of the more than one antibodies are the same. In embodiments, the antibodies are the same and bind the same antigen. In embodiments, the antibodies are the same and bind the same epitope of an antigen. In embodiments, each of the more than one antibodies binds the same antigen.

In embodiments, the first dosage form includes more than one antibody, wherein each of the more than one antibodies are different. In embodiments, each of the more than one antibodies bind a different antigen.

In embodiments, the first oligoribonucleotide and the second oligoribonucleotide have a sequence complementarity of at least 85% over at least 20 continuous nucleotides. In embodiments, the first oligoribonucleotide and the second oligoribonucleotide have a sequence complementarity of at least 85%, 86%, 87%, 88%, 89%, 90%, 91%, 92%, 93%, 94%, 95%, 96%, 97%, 98%, or 99% over at least 20 (e.g., 21, 22, 23, 24, 25, 26, 27, 28 29, 30, 31, 32, 33, 34, 35, 36, 37, 38, or 40) continuous nucleotides.

In embodiments, the first oligoribonucleotide and the second oligoribonucleotide independently include one or more nucleobase analogs. In embodiments, the nucleobase analog is a Locked Nucleic Acid (LNA), 2'-O-alkyl nucleobase, 2'-Fluoro nucleobase, or 2'-OMe nucleobase. In embodiments, the nucleobase analog is a LNA. In embodiments, the nucleobase analog is 2'-O-alkyl nucleobase. In embodiments, the nucleobase analog is 2'-Fluoro nucleobase. In embodiments, the nucleobase analog is 2'-OMe nucleobase.

In embodiments, the first oligoribonucleotide and the second oligoribonucleotide are independently single-stranded oligoribonucleotides. In embodiments, the first oligoribonucleotide and the second oligoribonucleotide independently do not include a nucleic acid having internucleotide linkages wherein the linkage is a phosphorothioate. In embodiments, the first oligoribonucleotide and the second oligoribonucleotide independently do not include internucleotide linkages wherein the linkage is a phosphorothioate. In embodiments, the first oligoribonucleotide and the second oligoribonucleotide independently do not include a phosphorothioate linkage.

In embodiments, the first oligoribonucleotide and the second oligoribonucleotide independently include a nucleic acid analog (e.g. LNA, 2'-O-alkyl, 2'-Fluoro, or 2' O-Methyl (2'-OMe)) at 1, 2, 3, 4, 5, 6, 7, 8, 9, or 10 nucleobases. In embodiments, the nucleobase analog is at the 5'-end or the 3'-end of the first or second oligoribonucleotide. In embodiments, the nucleobase analog (e.g., LNA, 2'-O-alkyl, 2'-Fluoro, or 2' O-Methyl (2'-OMe)) is at the 5'-end or the 3'-end of the first or second oligoribonucleotide. In embodiments, the nucleobase analog (e.g., LNA, 2'-O-alkyl, 2'-Fluoro, or 2'-OMe) is at the 5'-end and the 3'-end of the first or second oligoribonucleotide.

In embodiments, the first oligoribonucleotide and the second oligoribonucleotide independently include three, four or five nucleobase analogs (e.g., LNA, 2'-O-alkyl, 2'-Fluoro, or 2' O-Methyl (2'-OMe)) at the 5'-end or the 3'-end of the nucleic acid sequence. In embodiments, the first oligoribonucleotide and the second oligoribonucleotide independently include three, four or five nucleobase analogs (e.g., LNA, 2'-O-alkyl, 2'-Fluoro, or 2' O-Methyl (2'-OMe)) at the 5'-end and the 3'-end of the nucleic acid sequence. In embodiments, the first oligoribonucleotide and the second oligoribonucleotide independently include three nucleobase analogs (e.g., LNA, 2'-O-alkyl, 2'-Fluoro, or 2' O-Methyl (2'-OMe)) at the 5'-end or the 3'-end of the nucleic acid sequence. In embodiments, the first oligoribonucleotide and the second oligoribonucleotide independently include three nucleobase analogs (e.g., LNA, 2'-O-alkyl, 2'-Fluoro, or 2' O-Methyl (2'-OMe)) at the 5'-end and the 3'-end of the nucleic acid sequence.

In embodiments, the first oligoribonucleotide and the second oligoribonucleotide independently have a length of 30-40 nucleotides. In embodiments, the first oligoribonucleotide and the second oligoribonucleotide independently have a length of 31-40 nucleotides. In embodiments, the first oligoribonucleotide and the second oligoribonucleotide independently have a length of 32-40 nucleotides. In embodiments, the first oligoribonucleotide and the second oligoribonucleotide independently have a length of 33-40 nucleotides. In embodiments, the first oligoribonucleotide and the second oligoribonucleotide independently have a length of 34-40 nucleotides. In embodiments, the first oligoribonucleotide and the second oligoribonucleotide independently have a length of 35-40 nucleotides. In embodiments, the first oligoribonucleotide and the second oligoribonucleotide independently have a length of 36-40 nucleotides. In embodiments, the first oligoribonucleotide and the second oligoribonucleotide independently have a length of 37-40 nucleotides. In embodiments, the first oligoribonucleotide and the second oligoribonucleotide independently have a length of 38-40 nucleotides.

In embodiments, the first oligoribonucleotide and the second oligoribonucleotide independently have a length of 30-39 nucleotides. In embodiments, the first oligoribonucleotide and the second oligoribonucleotide independently have a length of 30-38 nucleotides. In embodiments, the first oligoribonucleotide and the second oligoribonucleotide independently have a length of 30-37 nucleotides. In embodiments, the first oligoribonucleotide and the second oligoribonucleotide independently have a length of 30-36 nucleotides. In embodiments, the first oligoribonucleotide and the second oligoribonucleotide independently have a length of 30-35 nucleotides. In embodiments, the first oligoribonucleotide and the second oligoribonucleotide independently have a length of 30-34 nucleotides. In embodiments, the first oligoribonucleotide and the second oligoribonucleotide independently have a length of 30-33 nucleotides. In embodiments, the first oligoribonucleotide and the second oligoribonucleotide independently have a length of 30-32 nucleotides. In embodiments, the first oligoribonucleotide and the second oligoribonucleotide independently have a length of 30, 31, 32, 33, 34, 35, 36, 37, 38, 39 or 40 nucleotides.

In embodiments, the first oligoribonucleotide and said second oligoribonucleotide independently have a length of 8-10 nm. The term "length" as provided herein refers to the length of the longest dimension of an oligoribonucleotide from the 5' to the 3' end. For example, a double-stranded oligoribonucleotide as provided herein may include 32 base pairs and have a length of 10.9 nm, wherein each base pair has a length of 0.34 nm. In embodiments, the first oligoribonucleotide and said second oligoribonucleotide independently have a length of 8.2-10 nm. In embodiments, the first oligoribonucleotide and said second oligoribonucleotide independently have a length of 8.4-10 nm. In embodiments, the first oligoribonucleotide and said second oligoribonucleotide independently have a length of 8.6-10 nm. In embodiments, the first oligoribonucleotide and said second oligoribonucleotide independently have a length of 8.8-10 nm. In embodiments, the first oligoribonucleotide and said second oligoribonucleotide independently have a length of 9-10 nm. In embodiments, the first oligoribonucleotide and said second oligoribonucleotide independently have a length of 9.2-10 nm. In embodiments, the first oligoribonucleotide and said second oligoribonucleotide independently have a length of 9.4-10 nm. In embodiments, the first oligoribonucleotide and said second oligoribonucleotide independently have a length of 9.6-10 nm.

In embodiments, the first oligoribonucleotide and said second oligoribonucleotide independently have a length of 8-9.8 nm. In embodiments, the first oligoribonucleotide and said second oligoribonucleotide independently have a length of 8-9.6 nm. In embodiments, the first oligoribonucleotide and said second oligoribonucleotide independently have a length of 8-9.4 nm. In embodiments, the first oligoribonucleotide and said second oligoribonucleotide independently have a length of 8-9.2 nm. In embodiments, the first oligoribonucleotide and said second oligoribonucleotide independently have a length of 8-9 nm. In embodiments, the first oligoribonucleotide and said second oligoribonucleotide independently have a length of 8-8.8 nm. In embodiments, the first oligoribonucleotide and said second oligoribonucleotide independently have a length of 8-8.6 nm. In embodiments, the first oligoribonucleotide and said second oligoribonucleotide independently have a length of 8-8.4 nm.

In embodiments, the first oligoribonucleotide includes the sequence of SEQ ID NO:1. In embodiments, the second oligoribonucleotide includes the sequence of SEQ ID NO:2. In embodiments, the first oligoribonucleotide has the sequence of SEQ ID NO: 1. In embodiments, the second oligoribonucleotide has the sequence of SEQ ID NO:2.

In embodiments, the first oligoribonucleotide includes the sequence of SEQ ID NO:3. In embodiments, the second oligoribonucleotide includes the sequence of SEQ ID NO:4. In embodiments, the first oligoribonucleotide has the sequence of SEQ ID NO:3. In embodiments, the second oligoribonucleotide has the sequence of SEQ ID NO:4.

In embodiments, the first oligoribonucleotide or the second oligoribonucleotide independently do not include a phosphorothioate moiety.

In embodiments, the first chemical linker and the second chemical linker are independently formed through conjugate chemistry. In embodiments, the first chemical linker is attached to the hinge region of the first antibody. In embodiments, the second chemical linker is attached to the hinge region of the second antibody.

In embodiments, the first linker has the formula -$L^1$-$L^2$-$L^3$-$L^4$-$L^5$-wherein, $L^1$, $L^2$, $L^3$, $L^4$, and $L^5$ are independently a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^1$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^1$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^1$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^1$ is substituted with a plurality of substituent groups, each substituent group may optionally be different. In embodiments, when $L^1$ is substituted, it is substituted with at least one substituent group. In embodiments, when $L^1$ is substituted, it is substituted with at least one size-limited substituent group. In embodiments, when $L^1$ is substituted, it is substituted with at least one lower substituent group.

In embodiments, $L^2$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^2$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^2$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^2$ is substituted with a plurality of substituent groups, each substituent group may optionally be different. In embodiments, when $L^2$ is substituted, it is substituted with at least one substituent group. In embodiments, when $L^2$ is substituted, it is substituted with at least one size-limited substituent group. In embodiments, when $L^2$ is substituted, it is substituted with at least one lower substituent group.

In embodiments, $L^3$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^3$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^3$ is substituted with a plurality of substituent groups, each substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

In embodiments, $L^4$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene In embodiments, $L^4$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^4$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^4$ is substituted with a plurality of substituent groups, each substituent group may optionally be different. In embodiments, when $L^4$ is substituted, it is substituted with at least one substituent group. In embodiments, when $L^4$ is substituted, it is substituted with at least one size-limited substituent group. In embodiments, when $L^4$ is substituted, it is substituted with at least one lower substituent group.

In embodiments, $L^5$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^5$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_5$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^5$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^5$ is substituted with a plurality of substituent groups, each substituent group may optionally be different. In embodiments, when $L^5$ is substituted, it is substituted with at least one substituent group. In embodiments, when $L^5$ is substituted, it is substituted with at least one size-limited substituent group. In embodiments, when $L^5$ is substituted, it is substituted with at least one lower substituent group.

In embodiments, $L^1$ and $L^5$ are —CH$_2$—S—. In embodiments, $L^1$ includes —CH$_2$—S—. In embodiments, $L^1$ is —CH$_2$—S—. In embodiments, $L^5$ includes —CH$_2$—S—. In embodiments, $L^5$ is —CH$_2$—S—. In embodiments, $L^3$ includes azocinylene. In embodiments, $L^3$ is azocinylene. In embodiments, $L^3$ is 3a,8,9,13b-tetrahydro-1H-dibenzo[b,f][1,2,3]triazolo[4,5-d]azocine.

In embodiments, the second linker has the formula -$L^6$-$L^7$-$L^8$-$L^9$-$L^{10}$- wherein, $L^6$, $L^7$, $L^8$, $L^9$, and $L^{10}$ are independently a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^6$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^6$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^6$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^6$ is substituted with a plurality of substituent groups, each substituent group may optionally be different. In embodiments, when $L^6$ is substituted, it is substituted with at least one substituent group. In embodiments, when $L^6$ is substituted, it is substituted with at least one size-limited substituent group. In embodiments, when $L^6$ is substituted, it is substituted with at least one lower substituent group.

In embodiments, $L^7$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^7$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^7$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^7$ is substituted with a plurality of substituent groups, each substituent group may optionally be different. In embodiments, when $L^7$ is substituted, it is substituted with at least one substituent group. In embodiments, when $L^7$ is substituted, it is substituted with at least one size-limited substituent group. In embodiments, when $L^7$ is substituted, it is substituted with at least one lower substituent group.

In embodiments, $L^8$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^8$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^8$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^8$ is substituted with a plurality of substituent groups, each substituent group may optionally be different. In embodiments, when $L^8$ is substituted, it is substituted with at least one substituent group. In embodiments, when $L^8$ is substituted, it is substituted with at least one size-limited substituent group. In embodiments, when $L^8$ is substituted, it is substituted with at least one lower substituent group.

In embodiments, $L^9$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene In embodiments, $L^9$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_5$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^9$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^9$ is substituted with a plurality of substituent groups, each substituent group may optionally be different. In embodiments, when $L^9$ is substituted, it is substituted with at least one substituent group. In embodiments, when $L^9$ is substituted, it is substituted with at least one size-limited substituent group. In embodiments, when $L^9$ is substituted, it is substituted with at least one lower substituent group.

In embodiments, $L^{10}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In embodiments, $L^{10}$ is independently a bond, —O—, —S—, —NH—, —C(O)—, —C(O)O—, —C(O)NH—, —OC(O)—, —NHC(O)—, —NH—C(O)—NH—, —OC(O)NH—, —NHC(O)O—, substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{12}$, $C_6$-$C_{10}$, or phenylene), or substituted or unsubstituted heteroarylene (e.g., 5 to 12 membered, 5 to 10 membered, 5 to 9 membered, or 5 to 6 membered).

In embodiments, a substituted $L^{10}$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group. In embodiments, where the substituted $L^{10}$ is substituted with a plurality of substituent groups, each substituent group may optionally be different. In embodiments, when $L^{10}$ is substituted, it is substituted with at least one substituent group. In embodiments, when $L^{10}$ is substituted, it is substituted with at least one size-limited substituent group. In embodiments, when $L^{10}$ is substituted, it is substituted with at least one lower substituent group.

In embodiments, $L^6$ and $L^{10}$ are —CH$_2$—S—. In embodiments, $L^6$ includes —CH$_2$—S—. In embodiments, $L^6$ is —CH$_2$—S—. In embodiments, $L^{10}$ includes —CH$_2$—S—. In embodiments, $L^{10}$ is —CH$_2$—S—. In embodiments, $L^8$ includes azocinylene. In embodiments, $L^8$ is azocinylene. In embodiments, $L^8$ is 3a,8,9,13b-tetrahydro-1H-dibenzo[b,f][1,2,3]triazolo[4,5-d]azocine.

In embodiments, the first dosage form and the second dosage are in separate containers. In embodiments, the kit further includes instructions for treatment of cancer or an autoimmune disease. In embodiments, the kit further includes instructions for treatment of cancer. In embodiments, the kit further includes instructions for treatment of an autoimmune disease. In embodiments, the first dosage form includes a cell bound to a first antibody and a pharmaceutically acceptable excipient. In further embodiments, the first dosage form does not include an antibody of a different type compared to the first antibody. In other further embodiments, the first dosage form includes an antibody of a different type compared to the first antibody. In other further embodiments, the antibody of a different type is not bound to the first antibody.

In embodiments, the cell is an effector cell. In embodiments, the cell is a target cell. In embodiments, the cell is an autologous cell. In embodiments, the cell is an autologous immune cell. The term "autologous immune cell" as used herein refers to immune cells derived from an individual that is typically both donor and recipient of the immune cells. An autologous immune cell is derived from the same individual and hence is genetically identical to the host with the exception of any ex-vivo changes made to the autologous immune cell. In embodiments, autologous immune cells are removed from a subject's body, cultured, activated, coated with antibodies provided herein, and administered to the subject.

In an aspect a cell composition is provided. The cell composition includes a cell bound to a first antibody covalently attached to a first oligoribonucleotide through a first chemical linker. In embodiments, the cell composition is in a subject in vivo. In embodiments, the cell compositions is in an in vitro container and the first antibody is not bound to any other antibody directly, indirectly or otherwise.

III. Pharmaceutical Compositions

In an aspect is provided a pharmaceutical composition including a therapeutically effective amount of a cell composition including a cell bound to a first antibody covalently attached to a first oligoribonucleotide through a first chemical linker and a pharmaceutically acceptable excipient. In embodiments, the pharmaceutical composition including a therapeutically effective amount of the cell composition does not include a second antibody bound to the first antibody. In embodiments, the pharmaceutical composition does not include an antibody of a different type compared to the first antibody. In embodiments, the pharmaceutical composition includes an antibody of a different type compared to the first antibody. In further embodiments, the antibody of a different type is not bound to the first antibody. In further embodiments, the antibody of a different type is bound to the cell and is not bound to the first antibody.

In embodiments, the cell is an effector cell. In embodiments, the cell is a target cell. In embodiments, the antibody is an effector antigen-binding antibody. In embodiments, the second antibody is a target antigen-binding antibody.

IV. Methods of Use

For the methods provided herein including embodiments thereof any of the compositions provided herein may be used. For example, the first and second antibody may be a an target antigen-binding antibody or an effector antigen-binding antibody and the cells may be effector cells or target cells. The therapeutically effective amount of a first or second antibody may be the therapeutically effective amount of one antibody type or more than one antibody types. Thus, in an aspect is provided a method of treating a disease in a subject in need thereof, the method including administering to the subject a therapeutically effective amount of (i) a first antibody covalently attached to a first oligoribonucleotide through a first chemical linker; and (ii) a second antibody covalently attached to a second oligoribonucleotide through a second chemical linker. In embodiments, the first antibody and the second antibody are not bound to each other prior to administration. In embodiments, the first antibody and the second antibody are administered in separate dosage forms. In embodiments, the first antibody is an effector antigen-binding antibody. In embodiments, the second antibody is a target antigen-binding antibody. In embodiments, the first oligoribonucleotide and the second oligoribonucleotide have a sequence complementarity of at least 85% over at least 20 continuous nucleotides.

In embodiments, the first oligoribonucleotide and the second oligoribonucleotide hybridize in vivo in the subject, thereby binding said first antibody and said second antibody together. In embodiments, the effector antigen-binding antibody and the target antigen-binding antibody are administered simultaneously or sequentially. In embodiments, the effector antigen-binding antibody and the target antigen-binding antibody are administered simultaneously. In embodiments, the effector antigen-binding antibody and the target antigen-binding antibody are administered sequentially.

In an aspect is provided a method of treating a disease in a subject in need thereof, the method comprising: (i) isolating a cell from the subject, thereby forming an isolated cell; (ii) contacting the isolated cell ex vivo with a first antibody covalently attached to a first oligoribonucleotide through a first chemical linker, thereby forming an antibody cell conjugate; (iii) administering a therapeutically effective amount of said antibody cell conjugate to the subject. In embodiments, the administering further includes administering a second antibody covalently attached to a second oligoribonucleotide through a second chemical linker to the subject. In embodiments, the antibody cell conjugate and the second antibody are not bound to each other prior to administration of the antibody cell conjugate or the second antibody. In embodiments, the antibody cell conjugate and the second antibody are administered in separate dosage forms.

In embodiments, the first antibody is an effector antigen-binding antibody or a target antigen-binding antibody. In embodiments, the first antibody is an effector antigen-binding antibody. In embodiments, the first antibody is a target antigen-binding antibody.

In embodiments, the second antibody is an effector antigen-binding antibody or a target antigen-binding antibody. In embodiments, the second antibody is an effector antigen-binding antibody. In embodiments, the second antibody is a target antigen-binding antibody.

In embodiments, the first antibody is an effector antigen-binding antibody and the second antibody is a target antigen-binding antibody. In embodiments, the antibody cell conjugate and the second antibody are administered simultaneously or sequentially. In embodiments, the antibody cell conjugate and the second antibody are administered simultaneously. In embodiments, the antibody cell conjugate and the second antibody are administered sequentially.

In an aspect is provided a method of treating a disease in a subject in need thereof, the method including: (i) isolating a cell from the subject, thereby forming an isolated cell; (ii) contacting the isolated cell ex vivo with a first antigen-binding antibody covalently attached to a first oligoribonucleotide through a first chemical linker, thereby forming an antibody cell conjugate; (iii) contacting the antibody cell conjugate ex vivo with a second antibody covalently attached to a second oligoribonucleotide through a second chemical linker, wherein the first oligoribonucleotide and the second oligoribonucleotide hybridize, thereby forming a bispecific antibody cell conjugate; and (iv) administering a therapeutically effective amount of the bispecific antibody cell conjugate to the subject.

In embodiments, the first antibody is an effector antigen-binding antibody or a target antigen-binding antibody. In embodiments, the first antibody is an effector antigen-binding antibody. In embodiments, the first antibody is a target antigen-binding antibody.

In embodiments, the second antibody is an effector antigen-binding antibody or a target antigen-binding antibody. In embodiments, the second antibody is an effector antigen-binding antibody. In embodiments, the second antibody is a target antigen-binding antibody.

In embodiments, the first antibody is an effector antigen-binding antibody and the second antibody is a target antigen-binding antibody. For the methods provided herein, in embodiments, the disease is cancer, an infectious disease or an autoimmune disease. In embodiments, the disease is cancer, an infectious disease or an autoimmune disease. In embodiments, the disease is cancer. In embodiments, the disease is an infectious disease. In embodiments, the disease is an autoimmune disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Introduction to Exemplary Experiments

Applicants attached DBCO to two different antibodies and reacted one of the antibodies by Click Chemistry to a sense 5'-azido-2'OMe RNA and the other antibody to the antisense (complimentary) 5'-azido-2'OMe RNA. Each was purified and mixed together to form a BiTER. The BiTER was used to demonstrate the bispecific function. First, a T cell was incubated with anti-CD3-RNA-S(S=sense), excess was washed away, then incubated with anti-CEA-RNA-AS (AS=anti-sense), excess was washed away, then incubated with CEA+ target cells and cytotoxicity demonstrated. Alternatively, T-cells coated with anti-CD3-S were incubated with target cells incubated with anti-CEA-AS and cytotoxicity demonstrated. The advantage of this approach is that the anti-CEA-RNA-AS antibody can be administered to tumor bearing animals or patients followed by anti-CD3-RNA-S, i.e. a pretargeted cell based approach. Both approaches can be multiplexed for multiple T-cell surface markers and multiple Target cell surface markers. Another aspect of the invention is the formation of homodimers or mutimers of the same antibody using 5-azido-2'OMe-dsRNA. Homodimers can be used to neutralize viruses such as HIV and Covid-19.

Example 1: BiTER Production and Characterization

Applicants attached complementary, protected RNA oligomers to the reduced hinge region of antibodies allowing for their self-hybridization/oligomerization either in solution or at the cell surface. This enhancement resulted in more efficient production of oligomeric bispecific antibodies with lower background than previous bispecific antibodies produced using click chemistry methods, whether in solution or at the cell surface. This method allows for the efficient production of multispecific antibodies, including mixing of reagents to create various cocktails of bispecific antibodies.

Figure 1B:
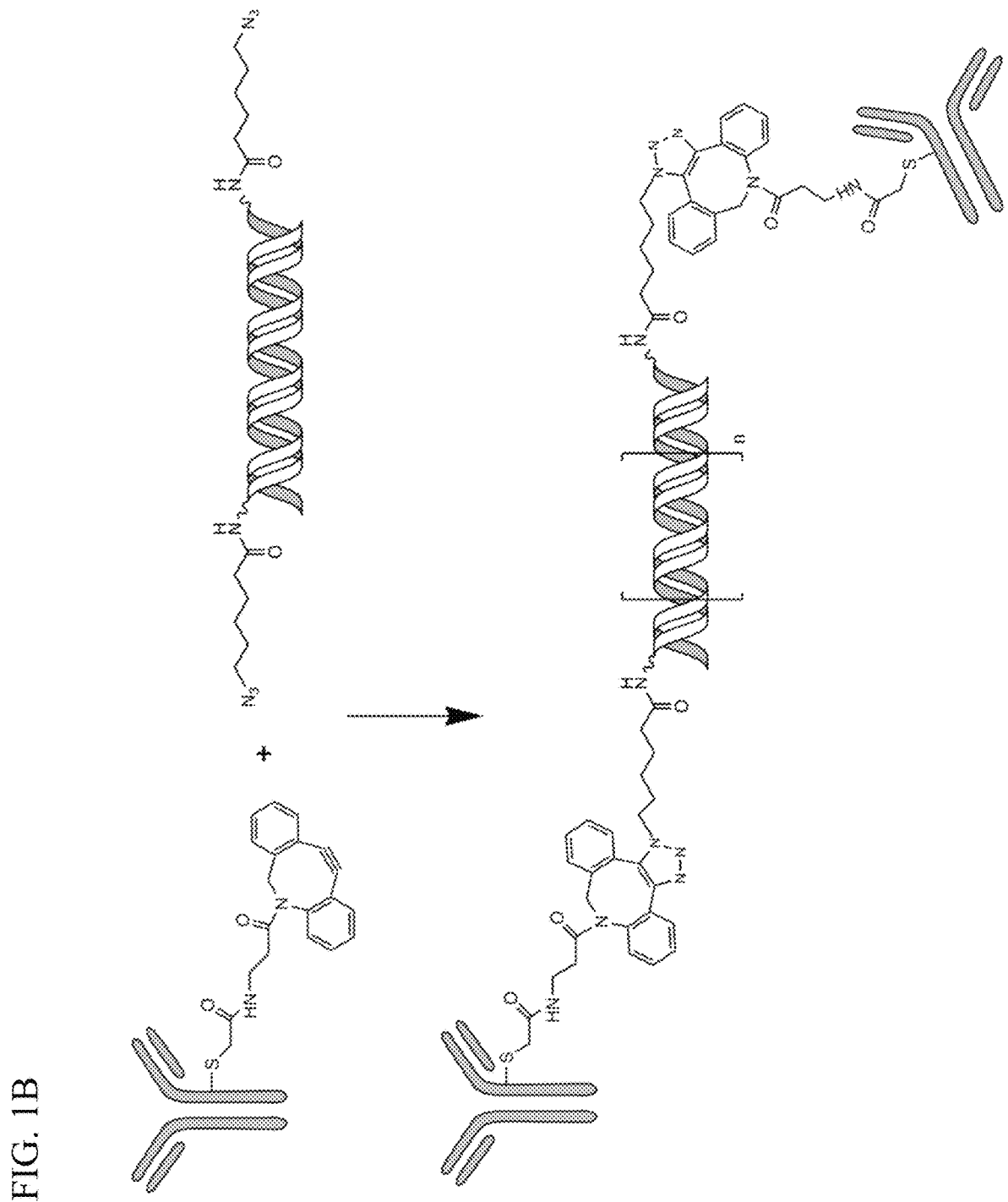
Figure 2A:
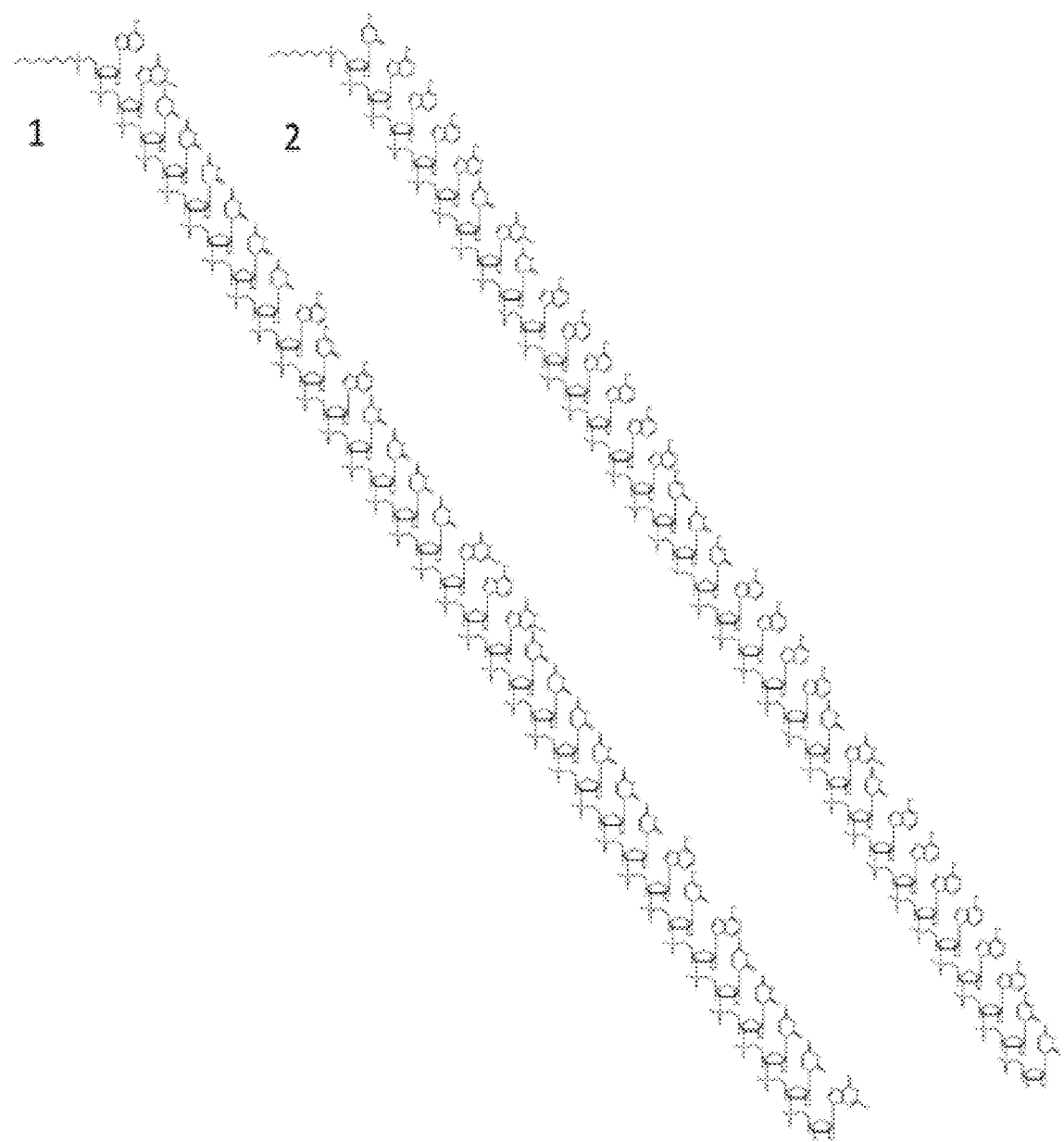
FIGS. 2A-2C. shows structures of example oligoribonucleotides used for the invention.
Figure 2B:
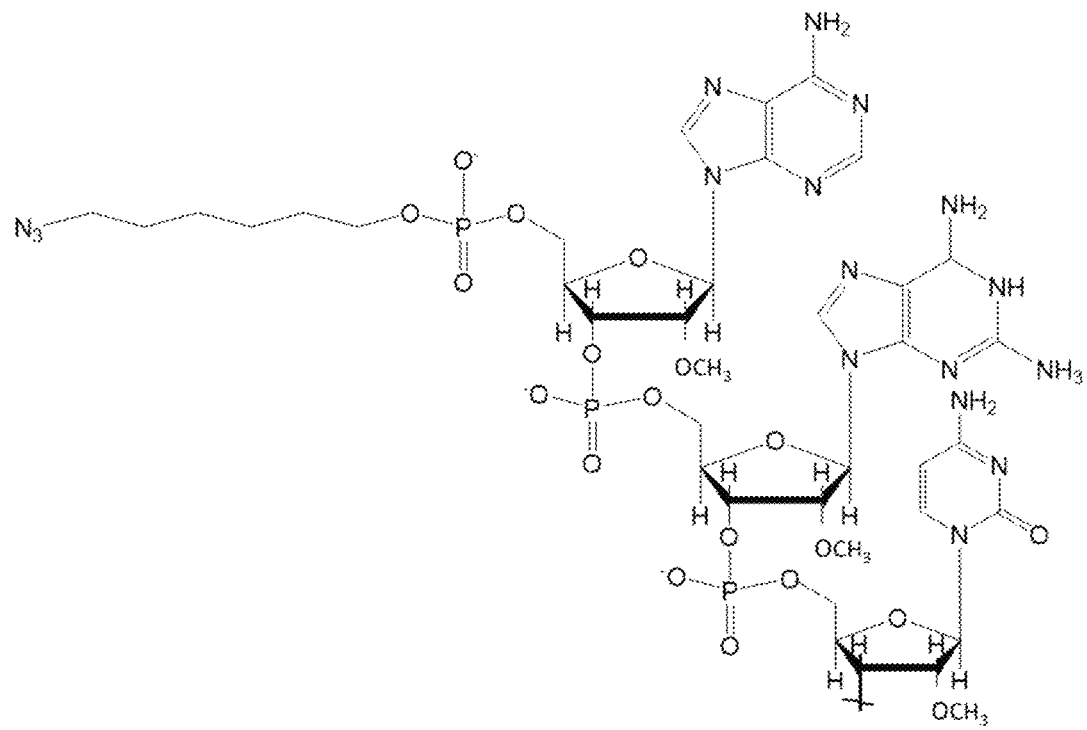
Figure 2C:
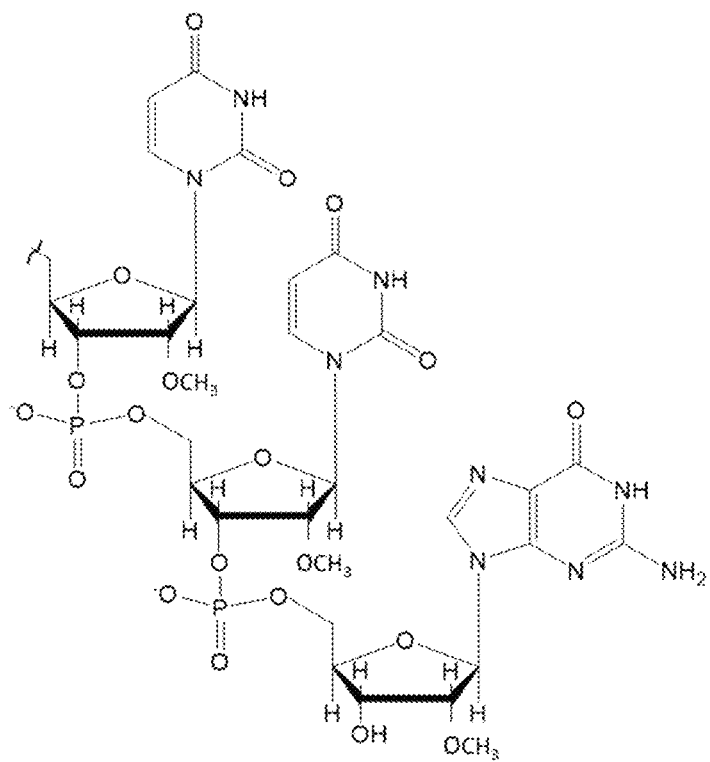

To produce the antibody conjugate, two antibodies were mildly reduced and derivatized with Br-DBCO. For example, antibody 1 was reacted by click chemistry with a first azido-oligo, while antibody 2 was reacted with a second azido-oligo that is complementary to the first oligo (FIG. 1A). After purification, the two antibodies were mixed and formed a tight cross-linked complex due to the formation of an RNA duplex (FIG. 1B). The duplex formed even at 4° C. in minutes and was shown to be indefinitely stable even at 37° C. This is due to the unique properties of the 2'OMe RNA oligos (FIG. 2) selected to attach the antibodies.

Figure 3A:
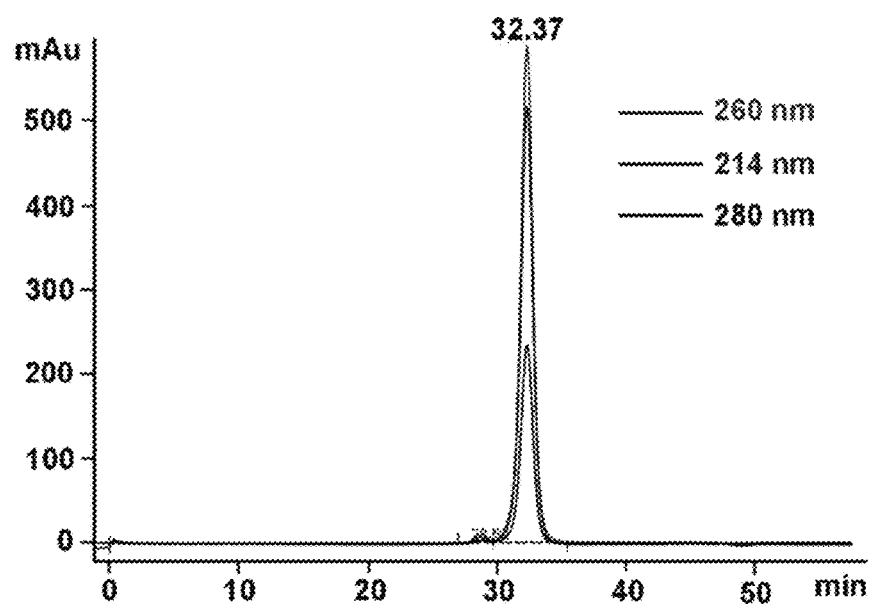
FIGS. 3A-3C. illustrates characterization of 5'azido-2'OMe RNA oligos by size exclusion HPLC.
Figure 3B:
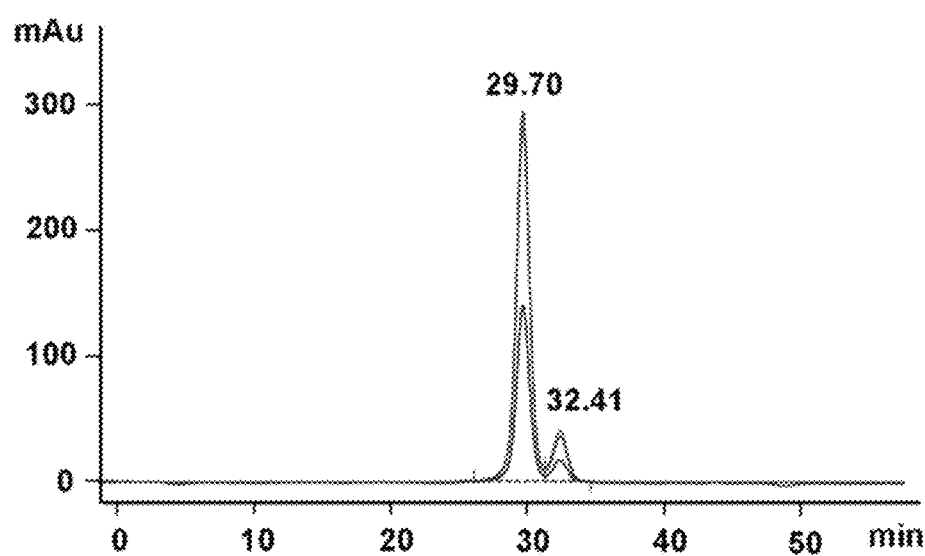
Figure 3C:
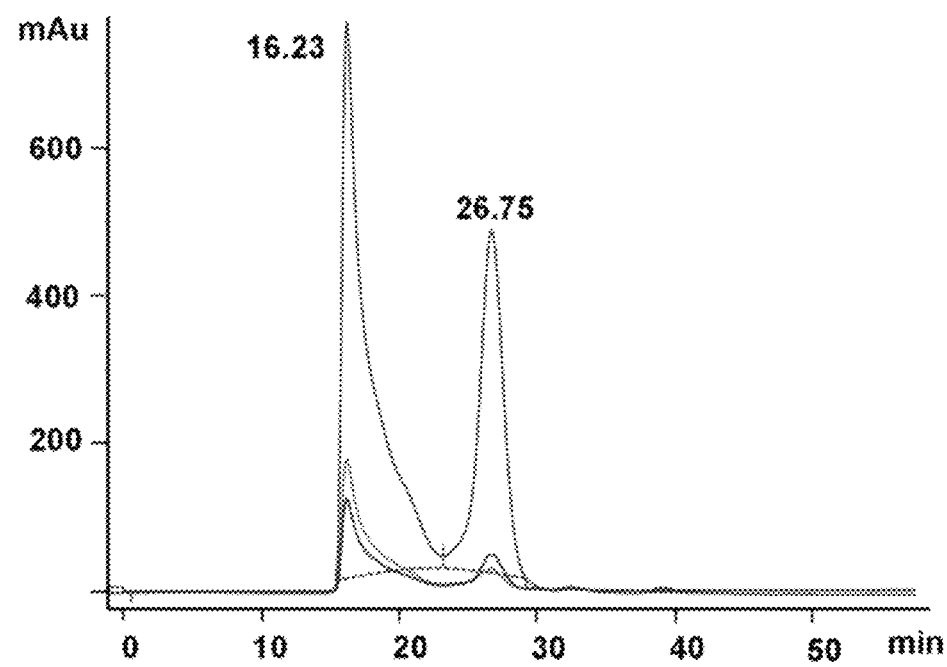

Applicants characterized the 5'azido-2'OMe RNA oligos by size exclusion HPLC, and showed that ds(double-stranded)RNA was formed after mixing the first and second complementary oligos (FIGS. 3A and 3B). DBCO derivatized antibody was then mixed with dsRNA, and SEC analysis showed that two identical antibodies were successfully cross-linked by the dsRNA (FIG. 3C).

Figure 4:
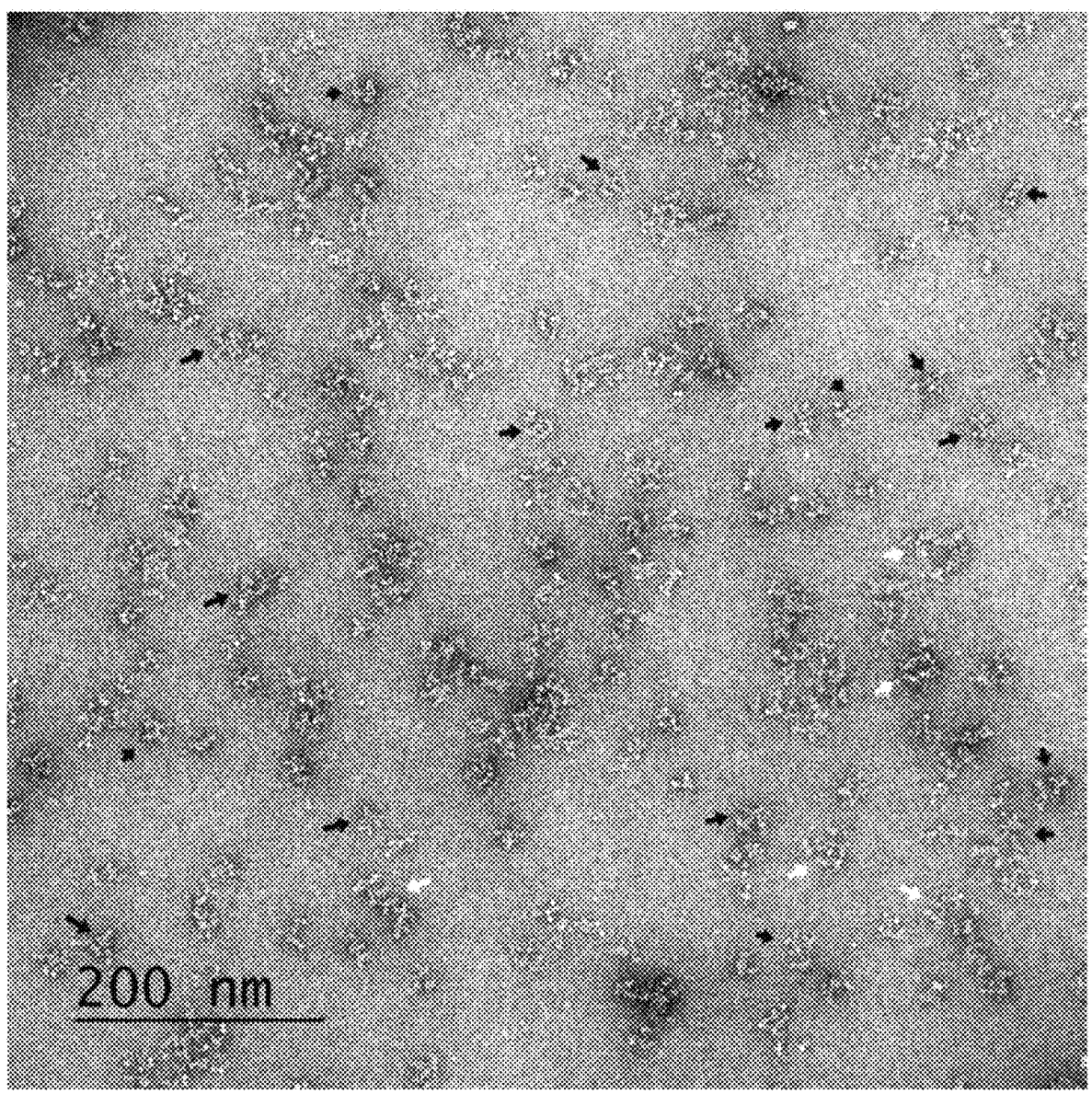
FIG. 4 shows TEM analysis of dsRNA crosslinked antibody OKT3. Black arrows show predominance of two linked antibodies with a random orientation on the grid. White arrows show presence of 3 antibodies linked in a circular pattern.

The anti-CD3 antibody OKT3 was reduced and reacted with bromoacetamido-DBCO in the hinge region and then incubated with a molar equivalent of 5'-azido-2'OMe-dsRNA. The product was purified by SEC (FIG. 3C) and analyzed by transmission electron microscopy to detect linked antibodies (FIG. 4). Two linked antibodies and three linked antibodies linked in a circular pattern were visualized. These results indicate that dsRNA crosslinking allows more flexibility (more orientations) than previous approaches where antibodies were linked by click chemistry methods.

Figure 5A:
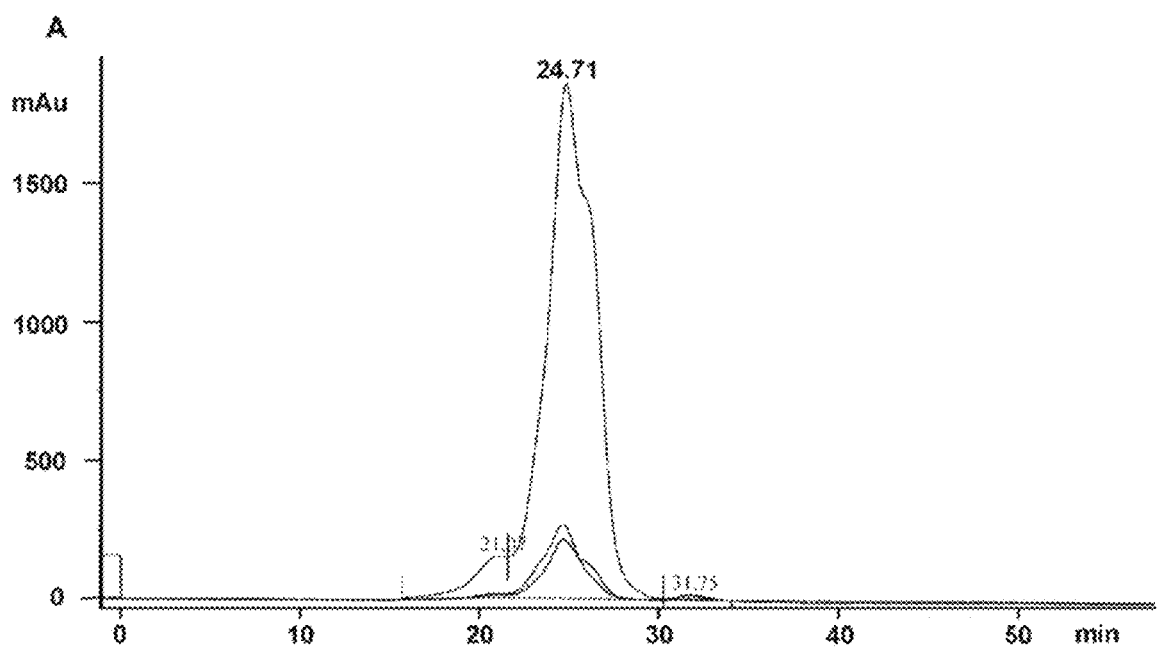
FIGS. 5A-5C. Production and purification of a dbBiTER in solution.
Figure 5B:
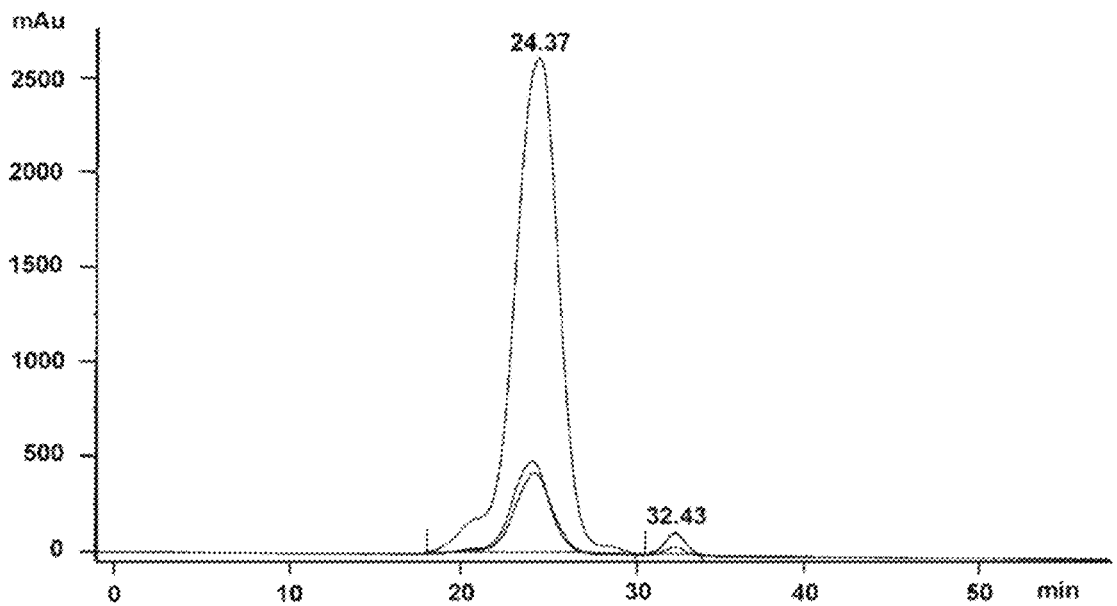
Figure 5C:
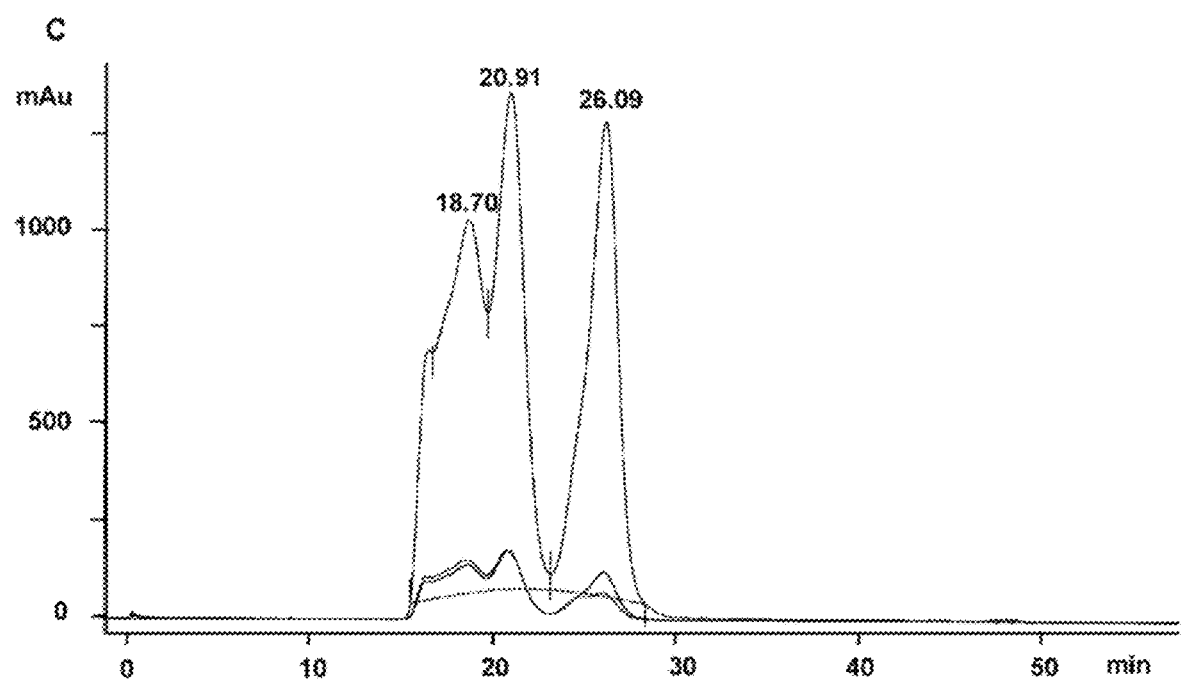
Figure 6A:
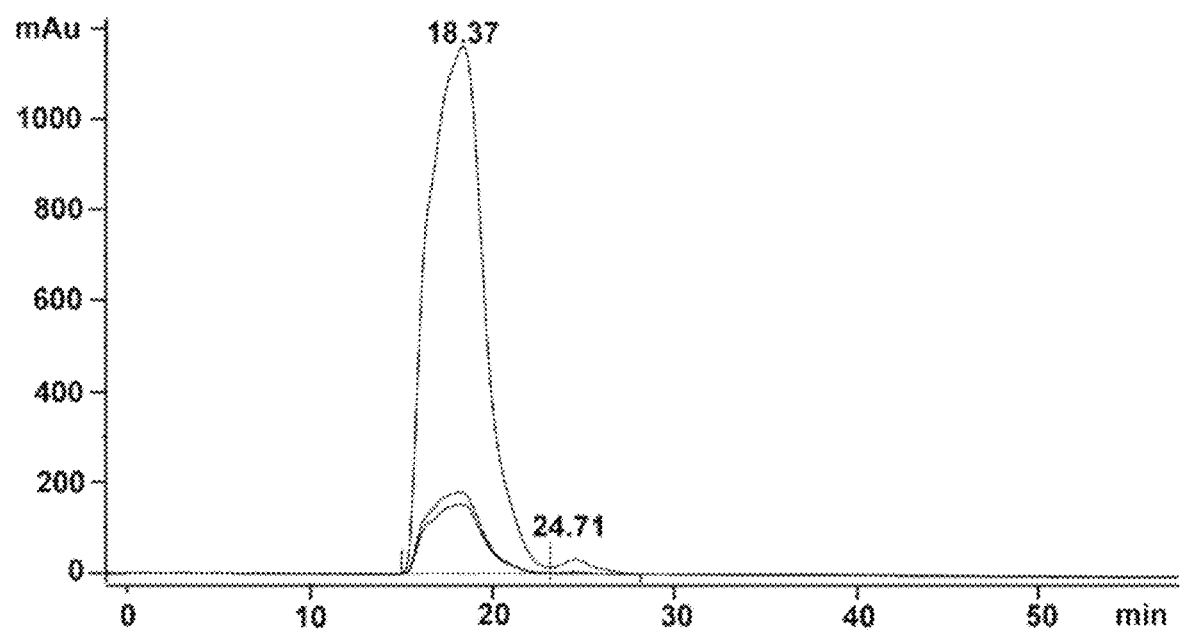
FIGS. 6A-6B. SEC chromatograms showing repurification of RNA cross-linked bispecific antibodies.
Figure 6B:
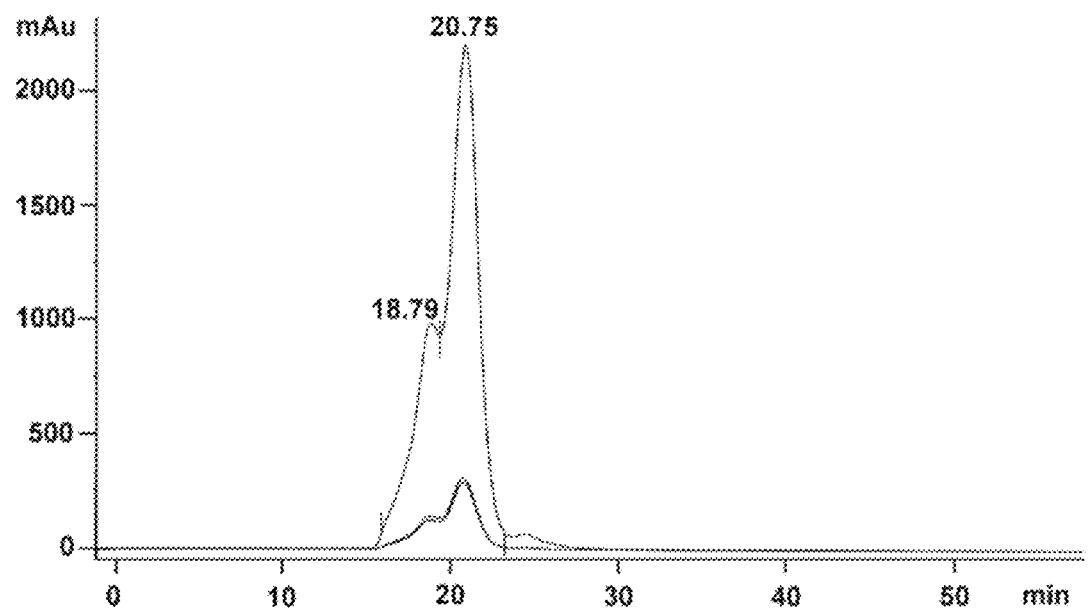

Next, the anti-CEA antibody M5A was reduced, reacted with Br-DBCO and 5'azido-2'OMe-oligo and purified by SEC (FIG. 5A). The anti-CD3 antibody OKT3 was then reacted with Br-DBCO and 5'azido-2'OMe-oligo complementary to the first oligo, and purified by SEC (FIG. 5B). Subsequently, the two RNA derivatized antibodies were mixed, and the resulting RNA cross-linked bispecific antibody conjugate was purified by SEC (FIG. 5C). The conjugate was then further purified by SEC (FIGS. 6A and 6B).

Figure 7:
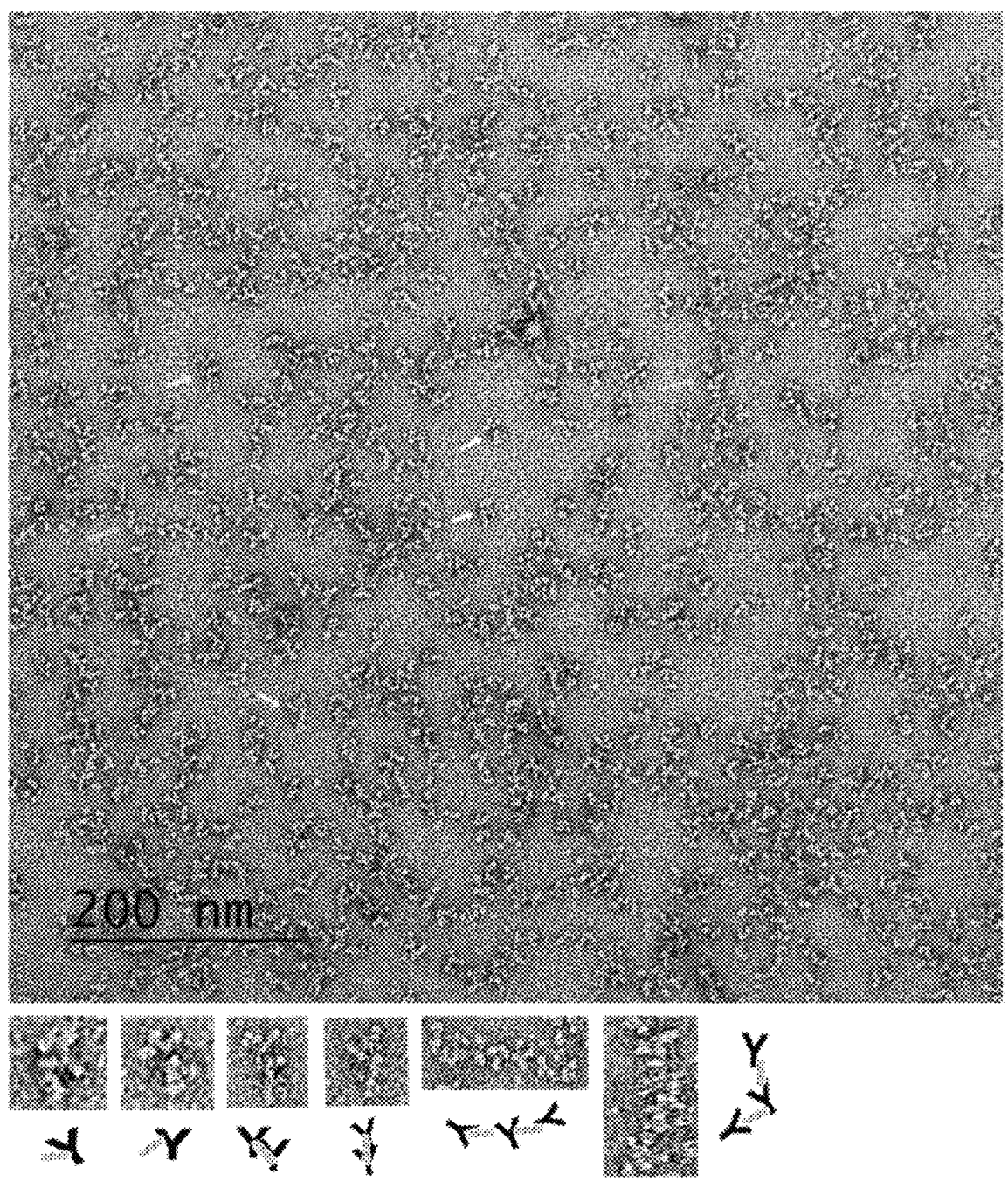
FIG. 7. Transmission electron microscopy analysis of dbBiTERs formed in solution. dbBiTERs formed in solution were imaged by TEM and selected regions shown by arrows indicate possible antibody orientations (including oligo density).

The SEC purified dbBiTER M5A-OKT3 were analyzed by transmission electron microscopy (FIG. 7). The results show a predominance of two cross-linked antibodies in random orientations on the grid. This indicates that this method of crosslinking antibodies results in more flexible orientations than with the dbBiTE method.

Figure 8A:
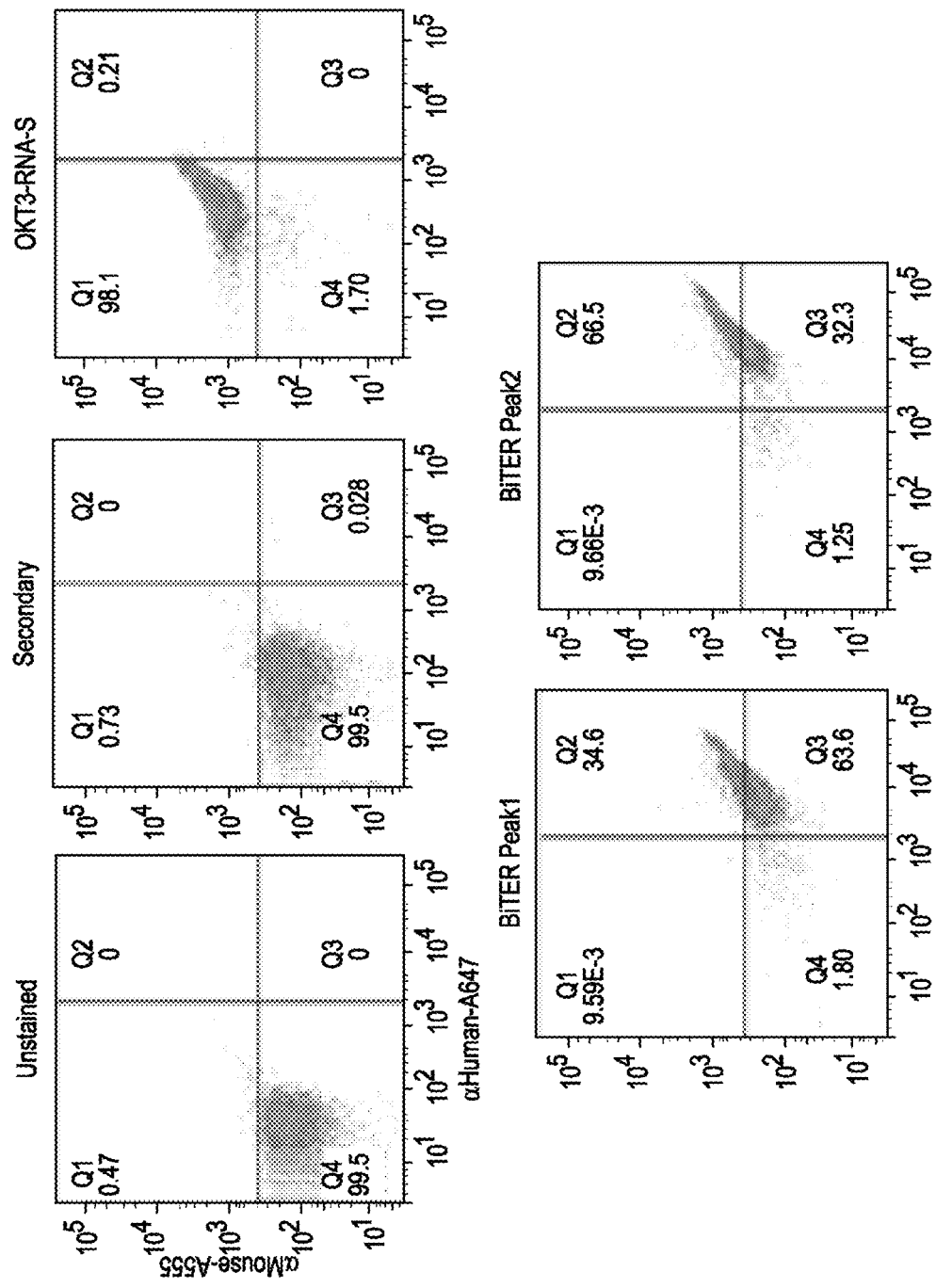
FIGS. 8A-8D. dbBiTER binding and antigen specific cytotoxicity.
Figure 8B:
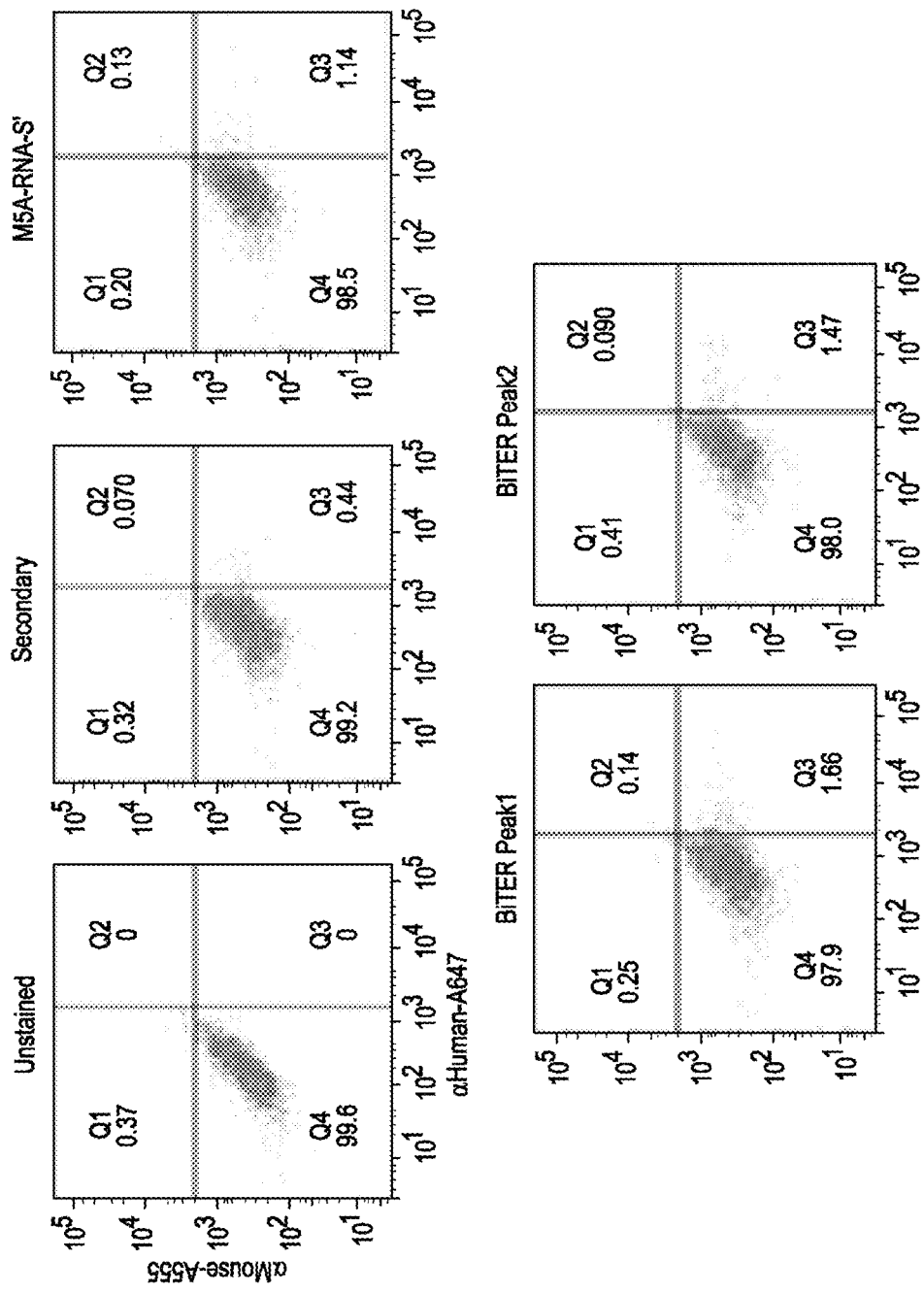
Figure 8C:
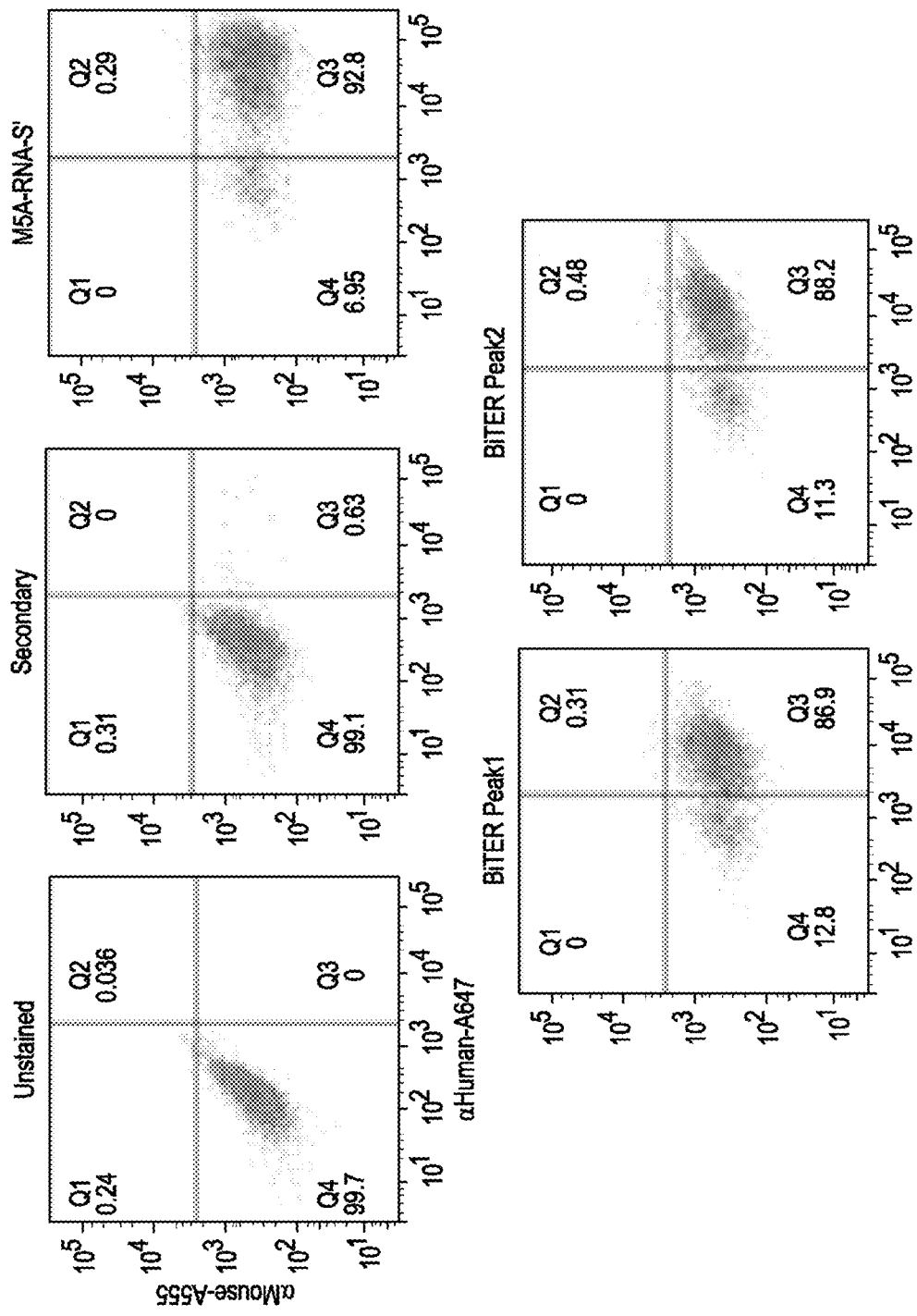

OKT3 conjugated to RNA or BiTER were incubated with CD3 expressing human T cells. The cells were analyzed by blow cytometry (FIG. 8A). Next, M5A conjugated to an RNA complementary to the first RNA or BiTER were incubated with CEA positive MDA-MB-231. The cells were analyzed by flow cytometry (FIG. 8B). Subsequently, activated human T-cells coated with OKT3 were conjugated to RNA. Two versions of BiTER were then incubated with target cell lines that express CEA, including breast MB231CEA, pancreas BxPC3, and colon LS174T. The three cells lines all expressed GFP. The OKT3 coated T-cells were mixed with the cell lines at various E:T ratios. Cytotoxicity was then measured by GFP fluorescence (FIG. 8C). Results show that the BiTER localized the T-cells to the target cell lines, resulting in cytotoxicity.

Figure 9A:
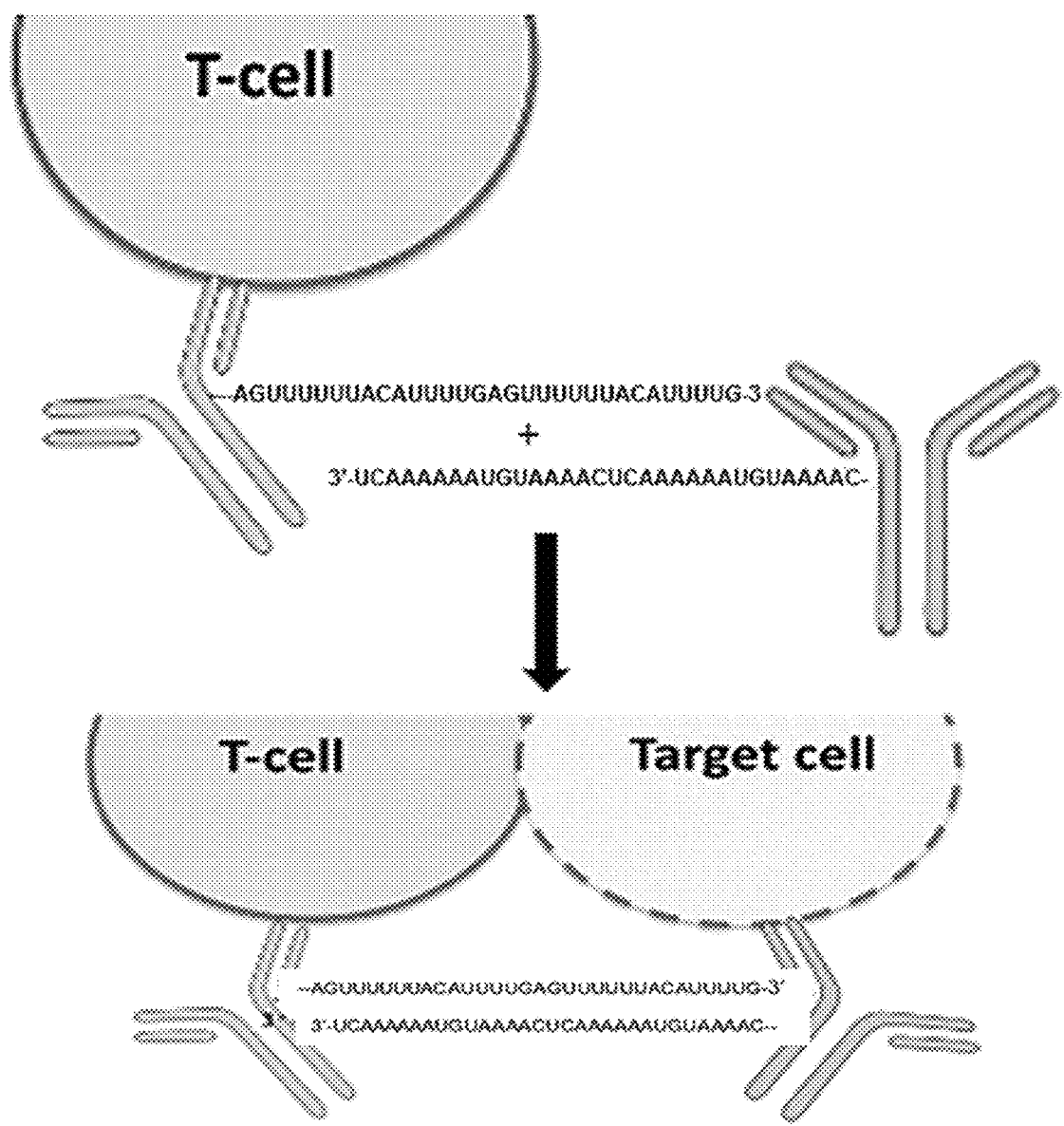
FIGS. 9A-9D. Schematic of cell-click dbBiTER formation on T cells, T cell binding and target cell lysis.
Figure 9B:
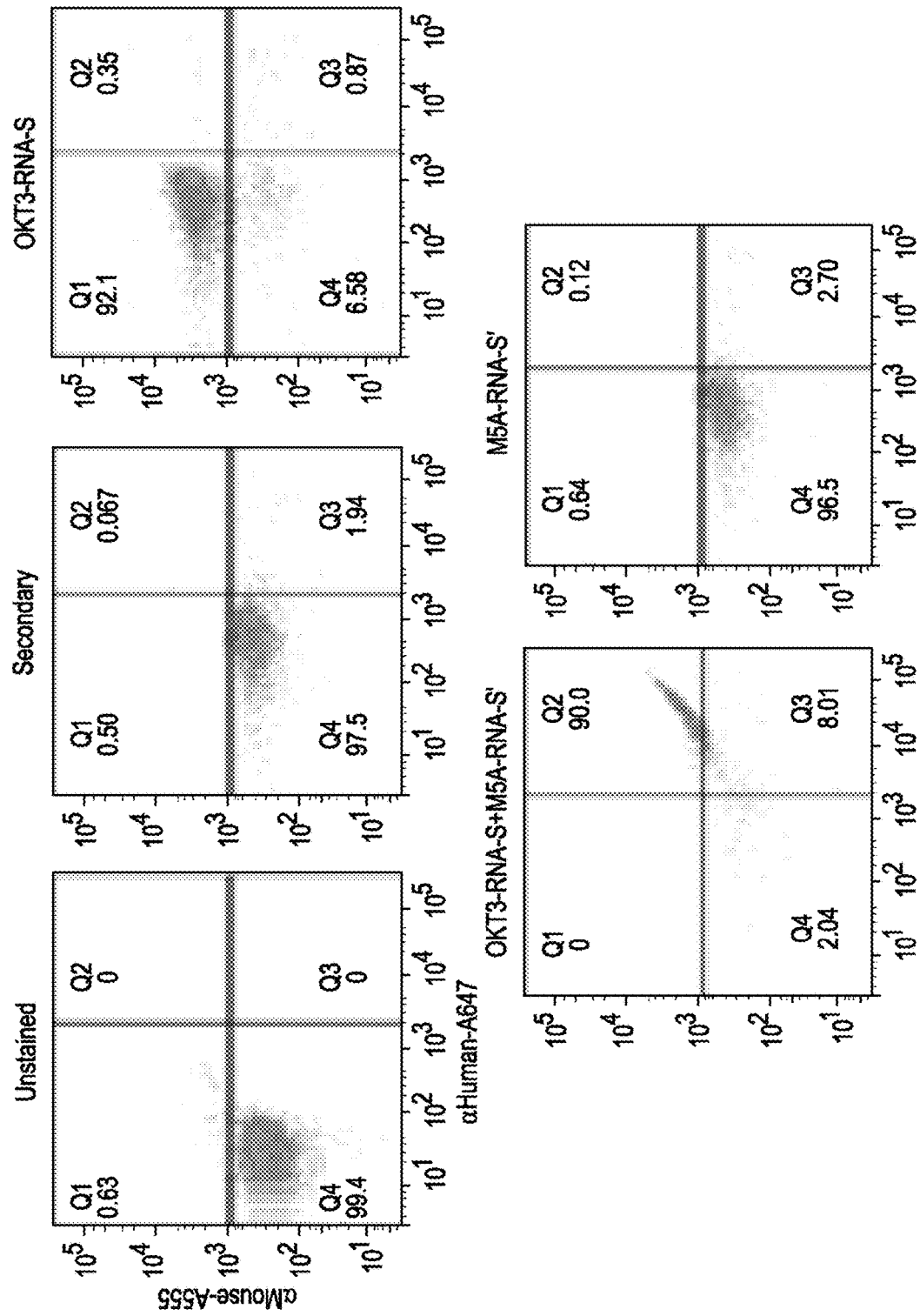

To further assess formation and functionality of BiTERs formed on cell surfaces, human T-cells were first coated with anti-CD3 antibody OKT3 conjugated to RNA. The coated T cells were then incubated with of anti-CEA M5A antibody conjugated to a complementary strand of RNA (1 h on ice, 20 µg/mL per ten million cells). The BiTER was then detected by flow cytometry (FIG. 9A). Formation of BiTER on human T-cells using different concentrations of anti-CEA M5A antibody conjugated to anti-sense RNA ranging from 2.5 to 20 µg/mL was analyzed by flow cytometry (FIG. 9B).

Figure 9C:
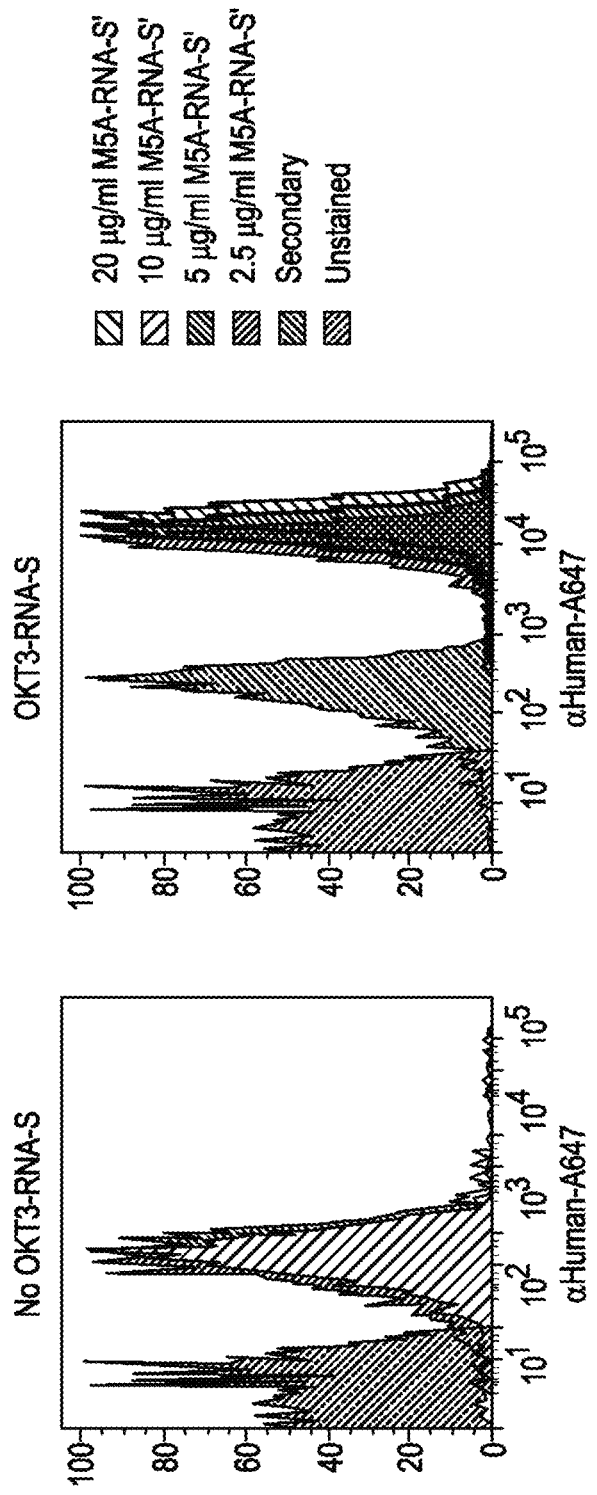

Subsequently, the activated human T-cells coated with OKT3 conjugated to RNA were incubated with two concentrations of anti-CEA M5A antibody conjugated to a complementary strand of RNA. The coated T-cells were incubated with target cell lines that either expressed CEA (MB231CEA) or did not express CEA (MB231). Various E:T ratios were tested, and cytotoxicity was measured by EGF fluorescence (FIG. 9C). The results indicate that the BiTER induces cytotoxicity specifically in CEA antigen expressing cells.

Figure 9D:
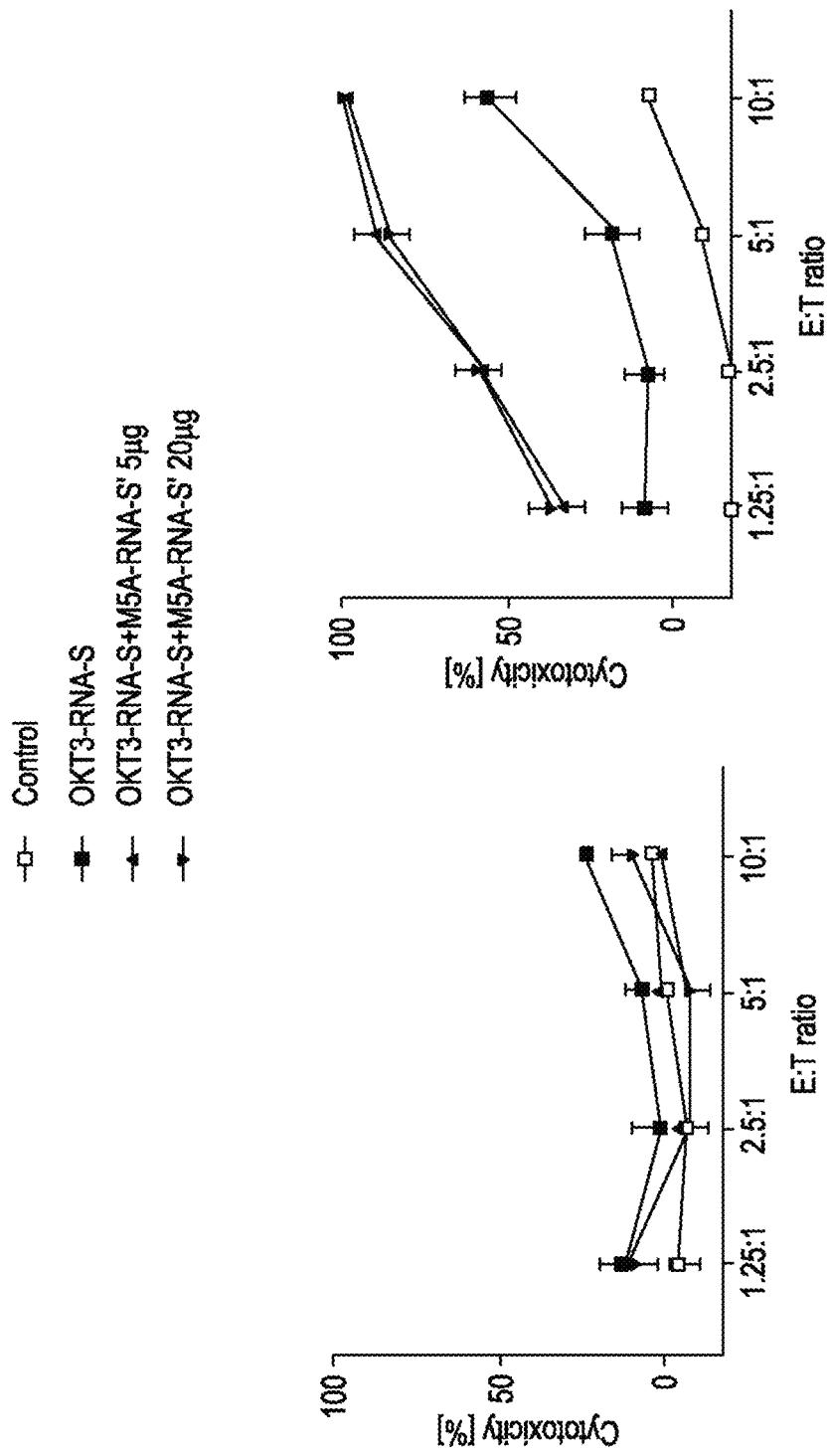

Further, activated human T-cells coated with OKT3 conjugated to RNA were incubated with target cell line MB231CEA coated with anti-CEA M5A antibody conjugated to anti-sense RNA at various E:T ratios. Cytotoxicity measured by GFP fluorescence (FIG. 9D).

Collectively, the results indicate that BiTERs formed on the surface of target or effector cells function to induce target cell death.

Example 2: BiTER Antigen Crosslinking

Figure 10:
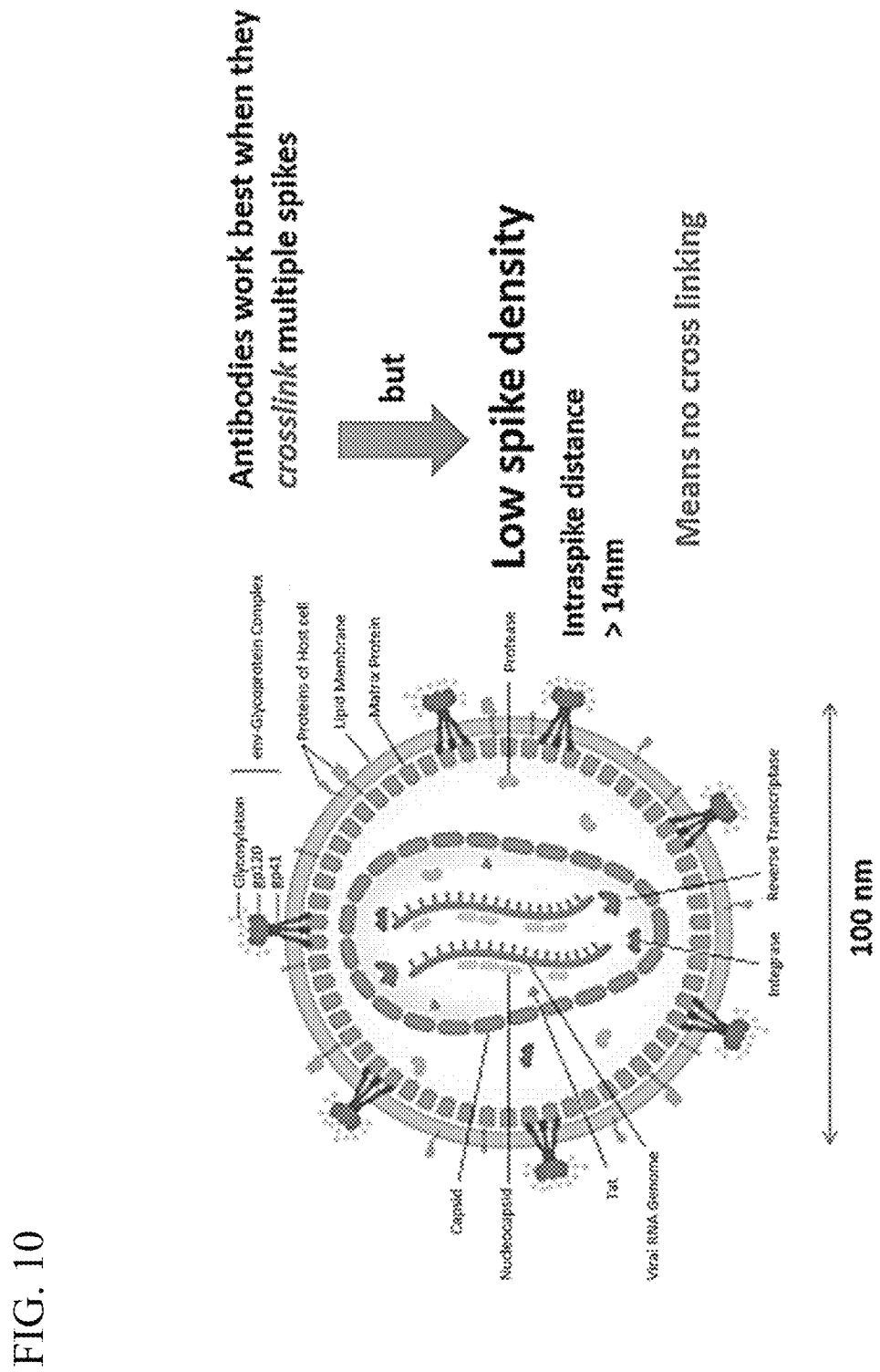
FIG. 10. A cartoon showing the distance between low-density glycoproteins on a human immunodeficiency virus (HIV).

Applicants showed that BiTERs may be used to neutralize HIV. Although antibodies targeting glycoproteins may neutralize the virus, the antibodies function more effectively when they crosslink multiple glycoproteins. However, low spike density means that a single antibody cannot cross-link glycoproteins (FIG. 10). Thus, Applicants proceeded to generate an antibody conjugate including two identical antibodies that bind HIV surface glycoproteins attached with complementary 2'OMe RNA oligonucleotides (FIGS. 11 and 12).

Figure 13:
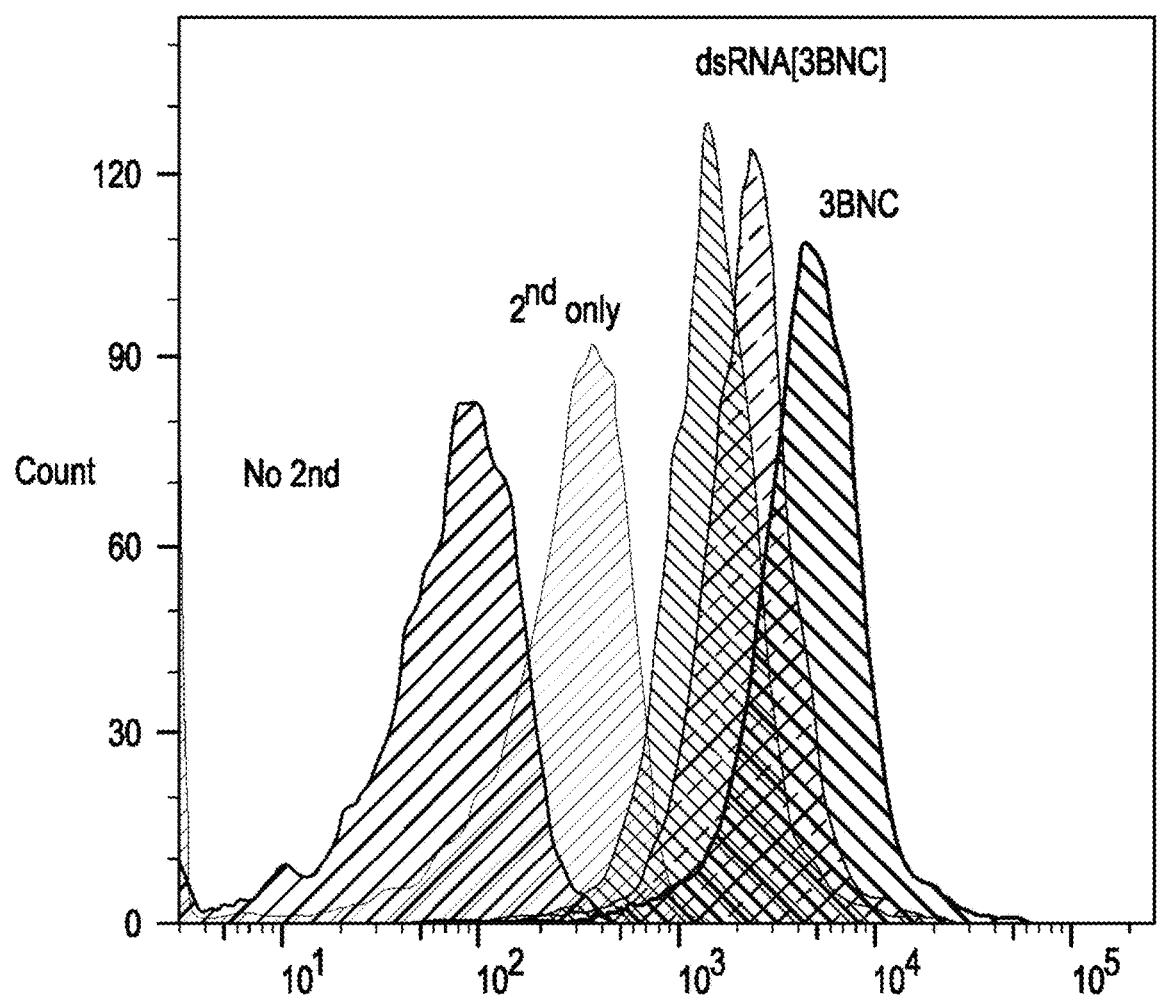
FIG. 13. Flow cytometry analysis illustrating binding of ds-RNA linked 3BNC117 antibodies to the HIV glycoprotein gp120.

The anti-gp120 antibody 3BNC was crosslinked to another 3BNC antibody using a dsRNA linker. The BiTER was shown to bind to cells expressing gp120, as analyzed by flow cytometry (FIG. 13). These results indicate that the dsRNA linked 3BNC antibodies may be used to crosslink multiple glycoproteins on the viral membrane, thereby effectively neutralizing the virus.

Example 3: Materials and Methods

The oligonucleotides were synthesized from the 3'-end to 5'-end, on 17.0 µmol scale, using standard phosphoramidite chemistry. Automated DNA/RNA Synthesizer OligoPilot10 plus from GE was used for the synthesis. The following phosphoramidites: 2'-OMe-Bz-A Phosphoramidite, 2'-OMe-C Phosphoramidite, 2'-OMe-G Phosphoramidite, 2'-OMe-U Phosphoramidite, were purchased from Thermo Fisher. Phthalamido Amino C6 lcaa CPG 1000 Å Support was purchased from Prime Synthesis.

Synthesis was performed using 3.5 eq of 2'-OMe phosphoramidite, and 8.5 min coupling time. The first added base was double coupled. Synthesis was completed in the DMT-ON mode. After that the coupling of 5'-Bromohexyl Phosphoramidite (Glen Research) was performed resulting in the attachment of Bromohexyl to the 5'-terminus of the oligo. Bromohexyl Phosphoramidite was double coupled with 2×3 eq for 2×5 min. Next step was the conversion of the bromide derivative into the azido derivative. We followed the protocol provided by Glen Research.

Conversion of the Bromide Derivative into the Azido Derivative

After the synthesis was completed the support in the reactor was washed with acetonitrile and dried with the stream of argon. The dry support was transferred into 15 mL plastic tube. For the conversion of 17 umoles scale synthesis, we dissolved 221 mg sodium azide and 510 mg of sodium iodide in 25 mL of DMF. Use heat 65° C. and sonication to facilitate dissolving of the azide and iodide in the DMA. Sodium azide/iodide solution was added to the support, tube was sealed, and contents were agitated by shaking and placed in the sonicator. Reaction mixture was sonicated at 65° C. for 65 min. Support was them washed with DMF (3×10 mL) and ACN (3×10 mL), in turn.

Deprotection

AMA was used for cleavage and deprotection. To minimize the displacement of azide with ammonia, Applicants deprotected at room temperature for 5 hrs. After the deprotection was completed the reaction mixture was filtered, filter cake washed with water-ethanol, v/v, and filtrate combined with the washed was evaporated in speedvac to the dry residue.

Purification

Crude product was purified on AKTA Purifier on Source30Q resin from GE, in 50 mM phosphate buffer pH12. Collected fractions were analyzed analytical PAGE. Fractions containing FLP were analyzed by HPLC. Fractions containing 85% plus of FLP were desalted by Ion-Paired chromatography on the PRP-1 resin from Hamilton, using 5 mM TBAA buffers pH7.1. Fractions containing the product were pooled, concentrated in speedvac and aliquoted/precipitated into IPA in presence of sodium chloride in order to remove the TBAA.

Figure 15A:
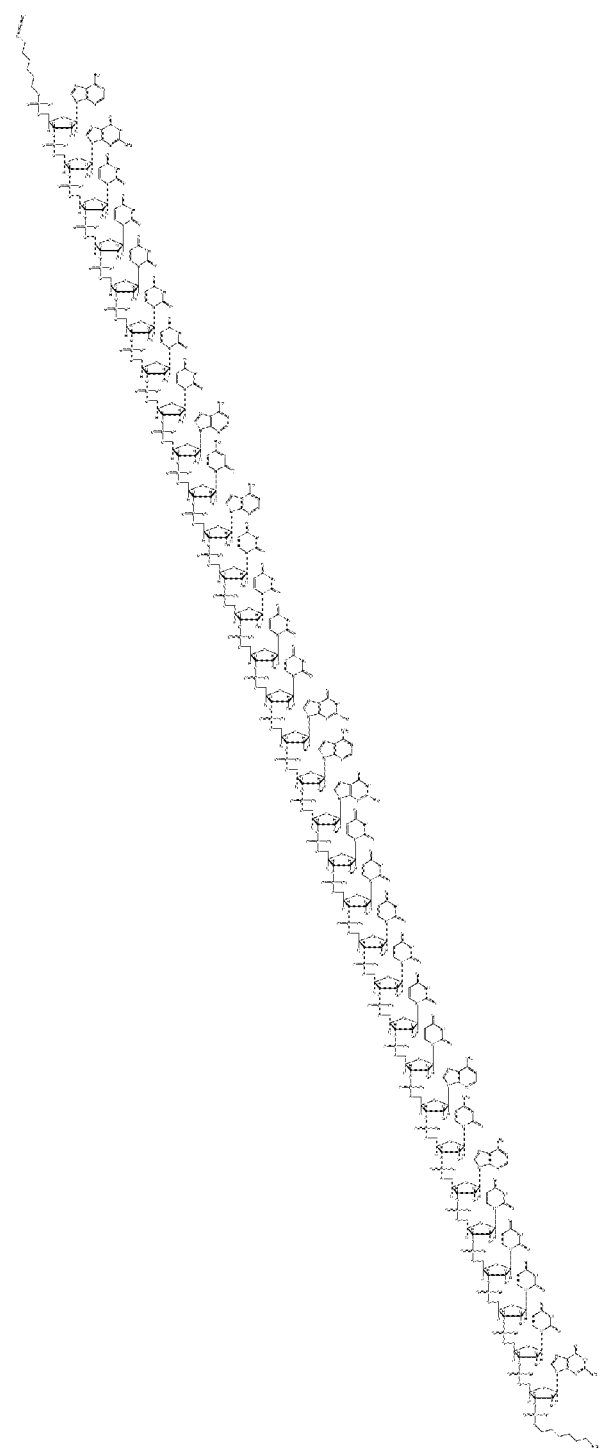
FIGS. 15A-15C. The structure of an example RNA sequence used for the invention.
Figure 15B:
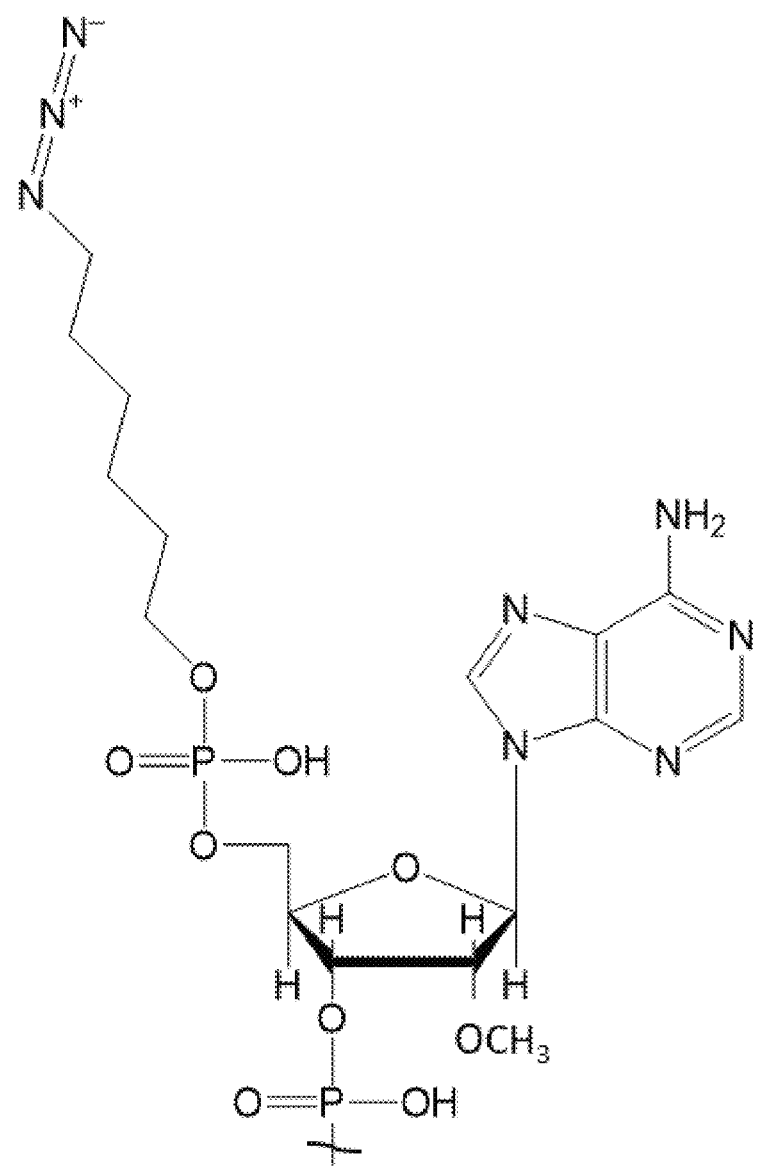
Figure 15C:
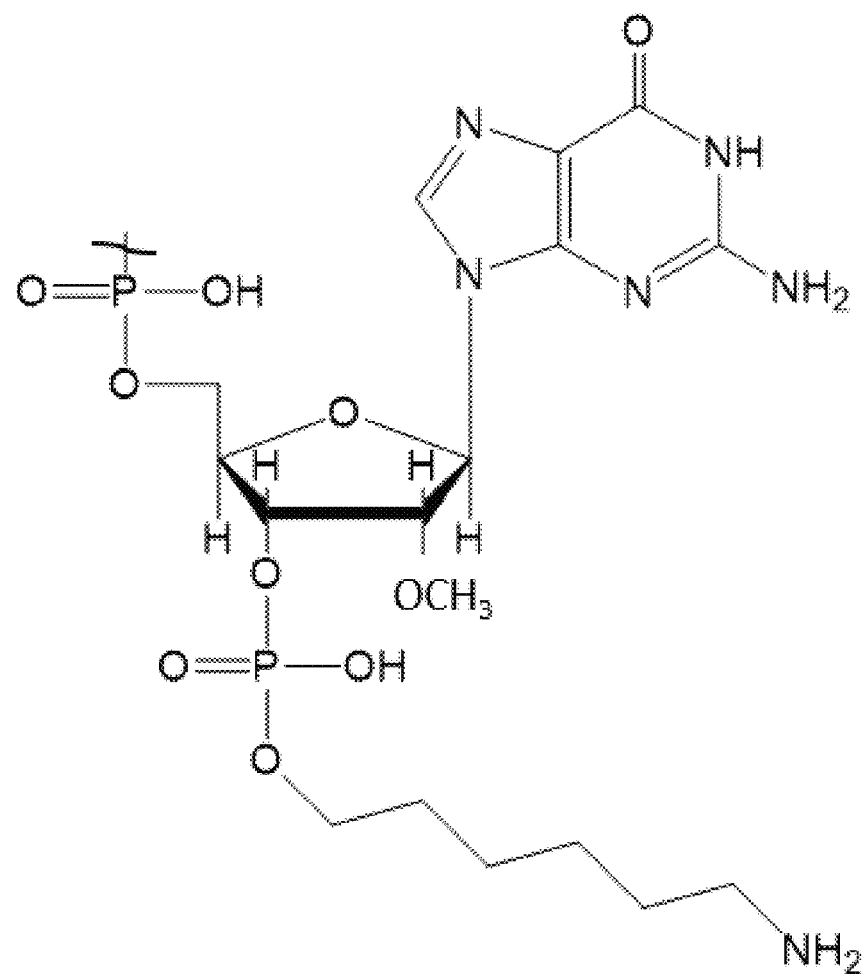
Figure 16:
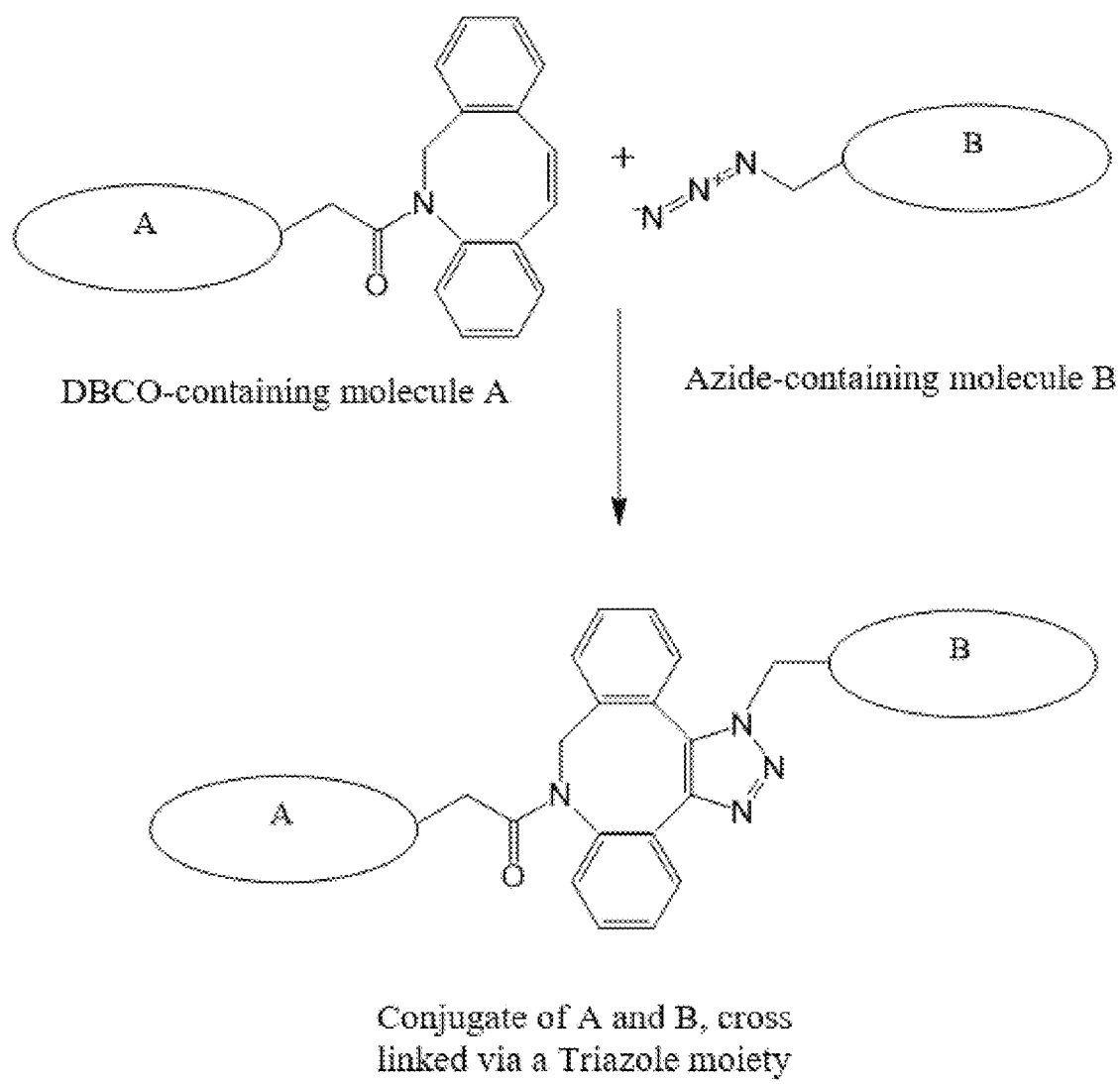
FIG. 16. A schematic showing a 5'-azido oligonucleotide conjugated to a DBCO-modified antibody by means of click-chemistry. Molecule A represents an antibody and molecule B represents an oligonucleotide.

```
JSMK-8721 32-mer (SEQ ID NO: 1; shown in
FIG. 15)
5'-/5AzideC6/mAmGmU mUmUmU mUmUmA mCmAmU mUmUmU mGmAmG mUmUmU mAmCmA mUmUmU mUmG/3AmMC6/-3'

JSMK-8735
                                           (SEQ ID NO: 2)
5'-/5AzideC6/mCmAmA mAmAmU mGmUmA mAmAmA mAmAmC mUmCmA mAmAmA mUmGmU mAmAmA mAmAmA mCmU/

3AmMC6/-3'

Primary Sequence
                                           (SEQ ID NO: 3)
5'-CAAAAUGUAAAAAACUCAAAAUGUAAAAAACU-3'

Secondary Sequence
                                           (SEQ ID NO: 4)
5'-AGUUUUUUACAUUUUGAGUUUUUUACAUUUUG-3'
```

Maximum delta G for binding of the 32-base pair complementary primary and secondary sequence is −53.94 kcal/mole (FIG. 14A). The delta G for binding of 16 complementary base pairs for the 5' end of the primary sequence is −26.18 kcal/mol (FIG. 14B), and the delta G for binding of 16 complementary base pairs for the 3' end of the primary sequence is −26.18 kcal/mol (FIG. 14C).

1. Reduction of Hinge Cystines in a OKT-3 Antibody:

OKT-3 (10 mg, 66.67 nmol) in 1.72 ml of PBS was reduced with a 30 molar excess of tris (2-carboxyethyl) phosphine (TCEP) at 37° C. for 2 h under Argon. The TCEP was removed by using a desalting spin column (Zeba, 7 KDa MW cutoff, Thermo Scientific).

2. Alkylation of a Reduced Antibody (Ab1) with Br-DBCO:

The reduced OKT-3 was reacted with 20 fold molar excess Bromoacetamido-DBCO at RT overnight under Argon. The excess Br-DBCO was removed by dialyzing in PBS (2 L×5). The conjugation was confirmed by Agilent 6520 QTOF mass spectrometry. The light chain had one DBCO and heavy chain had 4 DBCO.

3. Click Chemistry Conditions for Reaction of DBCO-Ab1 with Azido-RNA-S:

5 mg (33.33 nmol, 1116 µl) OKT-3-DBCO was reacted with azido-RNA1 (33.33 nmol) at RT for 24 h. Then the mixture was purified by a size exclusion column (Superdex 200, 10×300 GL, GE Healthcare) at a flow rate of 0.5 ml/min in PBS using GE AKTA Purifier. The main peak was collected, pooled and concentrated to the idea concentration.

4. Reduction of Hinge Cystines in a M5A Antibody:

M5A (10.9 mg, 72.66 nmol) in 2 ml of PBS was reduced with a 30 molar excess of tris (2-carboxyethyl) phosphine (TCEP) at 37° C. for 2 h under Argon. The TCEP was removed by using a desalting spin column (Zeba, 7 KDa MW cutoff, Thermo Scientific).

5. Alkylation of a Reduced Antibody (Ab2) with Br-DBCO:

The reduced M5A was reacted with 20 fold molar excess Bromoacetamido-DBCO at RT overnight under Argon. The excess Br-DBCO was removed by dialyzing in PBS (2 L×5). The conjugation was confirmed by Agilent 6520 QTOF mass spectrometry. The light chain had one DBCO and heavy chain had 3 DBCO.

6. Click Chemistry Conditions for Reaction of DBCO-Ab2 with Azido-RNA-AS:

5 mg (33.33 nmol, 1182 µl) M5A-DBCO was reacted with azido-RNA2 (33.33 nmol) at RT for 24 h. Then the mixture was purified by a size exclusion column (Superdex 200, 10×300 GL, GE Healthcare) at a flow rate of 0.5 ml/min in PBS using GE AKTAPurifier. The main peak was collected, pooled and concentrated to the idea concentration.

7. BiTER:

Mixed above 3 and 6. After reacted at RT for 2 h, the mixture was purified by a size exclusion column (Superdex 200, 10×300 GL, GE Healthcare) at a flow rate of 0.5 ml/min in PBS using GE AKTAPurifier. The three peaks were collected, pooled and concentrated to the idea concentration. Then they were re-purified one more time by using the same method.

Transmission Electron Microscopy:

TEM experiments were performed as previously described (Kujawski et al. BMC Cancer (2019) 19:882).

Example 4: Kits

A kit provided herein including embodiments, may include antibody A conjugated to a 2'-OMe modified oligoribonucleotide, Strand A. Using click chemistry methods, strand A is conjugated to the reduced hinge region of antibody A, wherein antibody A is directed to either an antigen specific to a given effector or target cell.

The antibody A-2'OMe-RNA-A reagent is either (1) injected to localize to effector or target cells in vivo, (2) incubated ex vivo with effector cells collected from the patient and then injected into the patient, or (3) incubated ex vivo with both A-2'OMe-RNA-A and antibodies B, C, D, etc.-(2'OMe-RNA-B) and injected into the patient. Strand B is a 2'-OMe modified oligoribonucleotide fully complementary to the Strand A.

In case (1), time is allowed for antibody A to localize to either target or effector cells, depending on antigen specificity of antibody A. Strand B is then conjugated to the reduced hinge region of antibodies B, C, D, etc. by Click chemistry methods. The antibody B-2'OMe-RNA-B reagent is then injected into the patient. If antibody A is bound to effector cells, antibodies B, C, D, etc. bind target cells, and thus specifically direct the target cells to the effector cells by virtue of strand A hybridizing to complementary strand B. If antibody A is directed at target cells, antibody B would be directed at effector cells, and thus, antibody B would direct the effector cells to antibody A bound target cells. Either option is possible, and depends upon which option is most effective. Further, if multiple copies of antibody A-2'OMe-RNA-A are bound to the effector cells, they are capable of hybridizing to either single or multiplexed antibodies B, C, D, etc. (-2'OMe-RNA-B), thus increasing the number of potential target antigens.

In case (2), after injection of the ex vivo produced effector cells bound to antibody A-2'OMe-RNA-A, antibodies B, C, D, etc. conjugated to 2'OMe-RNA-B are injected. The timing of the second injections in both case (1) and (2) are based on how long antibody A-2'OMe-RNA-A can be detected on the cell surface of effector cells, and time of clearance in vivo.

In case (3), the effector cells are preloaded for targeting appropriate antigens.

The kit provided herein is used for generating autologous cells bound to antibody reagents. Effector cells isolated from a patient are incubated ex vivo with either antibody A-2'OMe-RNA-A or sequentially with antibodies A-2'OMe-RNA-A and antibody B-2'OMe-RNA-AS, or additional antibodies C, D, etc. 2'OMe-RNA-B. Autologous cells include cells isolated from peripheral blood, including B-cells, T-cells, NK-cells, monocytes, neutrophils, platelets, and red blood cells.

The autologous cells (i.e. B-cells, T-cells, NK-cells, etc.) may need to be expanded ex vivo to generate a therapeutic dose. However, certain autologous cells (i.e. monocytes, neutrophils, platelets, or red blood cells) may be isolated in sufficient quantities directly from blood.

The 2'OMe RNA hybrids display superior stability compared to other types of oligonucleotides, for example phosphorothioate oligonucleotides and DNA. The minimum length of oligonucleotides provided in the kits described herein is about 8 nm to about 10 nm. This oligonucleotide length allows accessibility to its partner in the context of an antibody of width 12-15 nm, and further fulfilled the requirement of including enough base pairs to form a stable complex. For example, a duplex including 32-base pairs is predicted to be 10.9 nm long, based on the length of about 0.34 nm per base pair. This length does not include the linker, which allows for flexibility and added length. Further, the sequences of the oligonucleotides should allow for formation of secondary structures.

Example 5: Treatment of Autoimmune Diseases and Cancer

Autoimmune disease may be due to autoreactive-antibodies, autoreactive T-cells, or a combination thereof. In the case of lupus or chronic urticarial, a major mediator is IgE. Thus, treatment with anti-IgE antibodies is considered for treatment of these diseases. However, the B-cells that produce IgE may persist, making this therapy only temporarily effective. Use of anti-IgE dbBiTeR targeting effector cells allows for elimination of both IgE producing B-cells (since IgE is bound the surface of these B-cells) and the mast cells that bind the IgE. This approach may be also used to treat and prevent life threatening allergies that are mediated by IgE. Certain autoimmune diseases, such as multiple sclerosis (MS) and rheumatoid arthritis (RA), are triggered by memory B-cell responses that may be ameliorated by anti-B cell therapy or a complete bone marrow transplant. A more directed, less drastic approach is directing dbBiTeR coated effector cells to target memory B-cells (i.e. CD27 positive B-cells). In the case of T-cell mediated autoimmunities, including MS, RA, type 1 diabetes and celiac disease, expansion of regulatory T-cells (Tregs) has been effective. Thus, using the BiTeR technology described herein, an antibody that binds to the target autoantigen is cross-linked to an agonist antibody that binds CD25, an antigen highly expressed on Tregs. This results in in vivo re-targeting of antigen specific Tregs to the inflamed tissue. Localizing CD25 to the inflamed tissue selectively stimulates Tregs, thereby inhibiting inflammation.

Autoantigens include myelin oligodendrocyte glycoprotein (MOG) in MS and peptidylarginine deiminase in RA. For type 1 diabetes, autoantigens include insulin and glutamic acid decarboxylase (GAD65), and for celiac disease autoantigens include endomysium and transglutaminase 2.

Example 6: T Cell Surface Generation of Dual Bivalent, Bispecific T-Cell Engaging, RNA Duplex Cross-Linked Antibodies (dbBiTERs) for Re-Directed Tumor Cell Lysis Dual specific bivalent Bispecific T-cell engaging antibodies (dbBiTEs) can be generated directly on T-cell surfaces from parent antibodies using a click chemistry approach. We now show the generation of dbBiTEs on the surface of T cells along with the introduction of complementary single stranded 2'-OMe stabilized 32-mer RNA oligonucleotides allowing duplex formation between antibodies, designated as dbBiTERs. dbBiTERs generated in solution from anti-CEA M5A and anti-CD3 OKT3 retained specific binding to CEA positive vs CEA negative targets and to CD3 positive T-cells comparable to dbBiTEs. When T-cells were pre-coated with dbBiTEs or dbBiTERs and mixed with CEA positive vs CEA negative target cells, similar dose dependent and specific cytotoxicity were observed in a redirected cell lysis assay. On-cell generated dbBiTERs exerted potent cytotoxic responses against CEA positive targets and were localized at the cell surface by immuno-gold EM. In addition, we demonstrate that target and T-cells, each coated separately with complementary 2'OMe-RNA-linked antibodies can be cross-linked by RNA duplex formation in vitro to generate redirected cell lysis. The facile generation of dbBiTERs with specific cytolytic activity from intact antibodies and their generation on-cell offers a new avenue for antigen specific T-cell therapy.

Introduction

Redirected T-cell lysis of various malignancies using scFv based BiTEs has enjoyed considerable success in the clinic [1-2] because of their ease of production. However, the approach requires re-engineering of the parent antibodies, usually a tumor antigen specific antibody such as anti-CD19 [3] and others,[4] and an anti-effector cell antigen such as CD3. In addition, in the usual format where two scFv antibodies are joined by a linker, the resulting product is below the kidney threshold requiring constant infusion of the product. Approaches such as joining two half antibodies or two Fabs[5] together are potential solutions to the kidney threshold problem, but still require re-engineering of the parent antibodies.

Chemical cross-linking of antibodies is an attractive alternative in that clinically available antibodies can be used directly, but require that the two have orthogonal chemical groups available, otherwise resulting in a mixture of homo- and hetero-cross linked antibodies. While many cross-linking chemical approaches have been attempted, they usually result in complex mixtures with poor retention of antibody activity.[6] The advent of highly efficient click chemistry reagents has allowed us to re-investigate this approach by placing one of the reagents (eg., DBCO) in the hinge region of one antibody, and the other reagent (eg., azido) in the hinge region of the other antibody. Since the hinge regions are distant from the antigen combining regions, this approach preserves antibody activity. When the two antibodies are clicked together they form distinct 300 kDa particles we have dubbed dbBiTEs[7] for their retention of dual valency, a key feature of each original bivalent antibody designated as avidity.[8] Since the two antibodies are intimately connected at their hinge regions, they were visualized as six-lobed particles by EM analysis,[7] affirming the idea that two antibodies can fit together at their hinges without steric hindrance. Additionally, they retain their ability to bind to their specific targets and cause re-directed cell lysis similar to genetically engineered BiTEs.

Although BiTEs are usually systemically administered, Lum and coworkers demonstrated that chemically cross-linked antibodies can be used to coat T-cells ex vivo, then administered in vivo to redirect T-cell lysis.[9-13] This approach can potentially compete with CAR T cell therapy, [14] since there is no need to genetically engineer the patient's T-cells before administration. A further advantage is the use of low quantities, in the range of micrograms per mL, of cross-linked antibodies to coat the T-cells.[15-16] This is a major advantage compared to the use of hundreds of milligrams for systemically administered BiTEs. In spite of these advantages, the chemical approach described by Lum and coworkers produces a poorly characterized mixture of cross-linked antibodies. We show that dbBiTEs can be formed in situ by sequentially incubating T-cells with a click reagent modified anti-CD3 antibody and then with a second click agent modified anti-tumor antigen antibody. This approach addresses one of the disadvantages of current dbBiTE approach that requires purification of the cross-linked product in about a 30% yield before addition to T-cells.

In a further improvement, we have used click chemistry to derivatize the hinge regions of the two antibodies with 2'-OMe stabilized 32-mer complementary RNA oligos that form quantitative cross-linked duplexes at 4° C. in minutes. We show that these dbBiTERs have similar if not superior properties to dbBITEs in terms of coating T-cells for redirected lysis and can even re-direct T-cells coated with one of the 2'-OMe-RNA oligo pairs to lyse target cells coated with antibodies bearing a complementary 2'-OMe-RNA oligo.

Materials and Methods

Materials. Dibenzocyclootyne (DBCO) amine and bromoacetamido-PEGs-azide were purchased from Broadpharm. Bromoacetamido-DBCO (Br-DBCO) was synthesized as previously described.[7] NHS-Alexa-488 was purchased from Thermo Fisher, DBCO-Alexa 488 from Click Chemistry Tools, murine anti-human CD3 antibody (OKT3) from BioXcell (Lebanon, NH). Humanized anti-human CD3 antibody (hOKT3) and humanized anti-CEA antibody M5A was produced in house as previously described.[17]

Reduction of antibody hinge cystines. Anti-CD3 antibody OKT-3 (10 mg, 66.6 nmol) in 1.72 ml of PBS was reduced with a 30-molar excess of tris (2-carboxyethyl) phosphine (TCEP) at 37° C. for 2 h under Argon. TCEP was removed using a desalting spin column (Zeba, 7 KDa MW cutoff, Thermo Scientific). Similar conditions were used for hinge reduction of anti-CEA antibody M5A (10.9 mg, 72.6 nmol in 2 ml of PBS).

Alkylation of a reduced antibody (Ab1) with Br-DBCO. Reduced OKT-3 was reacted with a 20-fold molar excess Br-DBCO at RT overnight under Argon. The excess Br-DBCO was removed by dialysis vs PBS (2 L×5). Alkylation was confirmed by mass spectrometry on an Agilent 6520 QTOF mass spectrometer as previously described[7]. Similar conditions were used to alkylate hinge reduced M5A with either Br-DBCO (dbBiTER experiments) or bromoacetamido-PEGs-azide (on cell dbBiTE experiments). An aliquot (1 mg) of azido-M5A was further derivatized with NHS-Alexa-488 (molar ratio) for the on-cell dbBiTE experiments.

Synthesis of 5-azido-2'-OMe stabilized 32-mers and their Alexa 488 derivatives. The oligonucleotides were synthesized from the 3'-end to 5'-end, at 17.0 µmol scale, using standard phosphoramidite chemistry. The automated DNA/RNA Synthesizer OligoPilot10 plus from GE was used for the synthesis. The following phosphoramidites: 2'-OMe-Bz-A Phosphoramidite, 2'-OMe-C Phosphoramidite, 2'-OMe-G Phosphoramidite, 2'-OMe-U Phosphoramidite, were purchased from Thermo Fisher and the solid support, Phthalamido Amino C6 lcaa CPG 1000 Å from Prime Synthesis.

Synthesis was performed using 3.5 eq of 2'-OMe phosphoramidite, and 8.5 min coupling time. The first added base was double coupled. Synthesis was completed in the DMT-ON mode. After that the coupling of 5'-Bromohexyl Phosphoramidite (Glen Research) was performed resulting in the attachment of Bromohexyl to the 5'-terminus of the oligo. Bromohexyl Phosphoramidite was double coupled with 2×3 eq for 2×5 min. The conversion of the bromide derivative into the azido derivative protocol provided by Glen Research. After the synthesis was completed the support in the reactor was washed with acetonitrile and dried with the stream of argon. The dry support was transferred into 15 mL plastic tube. For the conversion of 17 µmole scale synthesis, we dissolved 221 mg sodium azide and 510 mg of sodium iodide in 25 mL of DMF, heated at 65° C. with sonication to facilitate dissolving of the azide and iodide in the DMF. The sodium azide/iodide solution was added to the support, the tube was sealed, and contents were agitated by shaking and sonicated at 65° C. for 65 min. The support was them washed with DMF (3×10 mL) and ACN (3×10 mL).

AMA was used for cleavage and deprotection. To minimize the displacement of azide with ammonia, we deprotected at room temperature for 5 hrs. After the deprotection was completed the reaction mixture was filtered, the filter cake washed with water-ethanol, v/v 1:1, the filtrate combined with the washes and evaporated in a Speedvac to the dry residue.

The crude product was purified on an AKTA Purifier on Source30Q resin from GE, in 50 mM phosphate buffer pH12. Collected fractions were analyzed analytical PAGE. Fractions containing FLP were analyzed by HPLC. Fractions containing 85% plus of FLP were desalted by Ion-Paired chromatography on PRP-1 resin from Hamilton, using 5 mM TBAA buffers pH7.1. Fractions containing the product were pooled, concentrated in a Speedvac and aliquoted/precipitated into IPA in presence of sodium chloride in order to remove the TBAA.

Azido-RNA-S reaction with DBCO-Alexa Fluor 488. DBCO-Alexa 488 (100 nmol in 8.62 µl of $H_2O$) was reacted with azido-RNA-S (100 nmol in 100 µl of $H_2O$) at RT for 24 h. The reaction mixture was purified by SE HPLC (Superdex 200, 10×300 GL, GE Healthcare) at a flow rate of 0.5 ml/min in PBS on a GE AKTA Purifier. The main peak at 32.74 min was collected, pooled and concentrated to about 1 mL.

Alexa 488-RNA-S binding with M5A-RNA-S'. M5A-RNA-S' (0.625 mg, 4.17 nmol in 111 µl of PBS) was reacted with Alexa Fluor 488-RNA-S (66.72 nmol in 894 µl of PBS) at RT for 3 h and purified by SE HPLC as above. The main peak at 23.97 min was collected, pooled and concentrated to about 280 µl. A similar procedure was used to react with OKT-3-RNA-S.

Click reaction of DBCO-antibodies with azido-RNA-S or azido-RNA-S'. DBCO-OKT3 (5 mg, 33.3 nmol in 1.1 mL of PBS) was reacted with azido-RNA-S (33.3 nmol in 0.5 mL of PBS) at RT for 24 h. The mixture was purified by SE HPLC as above. The main peak at 24.37 min was collected, pooled and concentrated to about 1 mL. A similar procedure was used to react DBCO-M5A (5 mg, 33.3 nmol in 1.2 mL of PBS) with azido-RNA-S' (33.33 nmol).

Cell Lines and Culture Conditions. Human breast carcinoma MDA-MB-231 cell line was transfected with CEA as previously described.[7] For in vitro cytotoxic assays MDA-MB-231±CEA, colon carcinoma LS174T and pancreatic carcinoma BxPC3 cell lines (both naturally expressing CEA) were transduced with GFP expressing lentivirus (MISSION pLK0.1-puro eGFP shRNA Control Transduction Particles, Sigma), selected with puromycin [1 µg/mL] and sorted on a FACS Aria Fusion cell sorter (BD Biosciences). All cell lines were grown in DMEM media containing 10% FBS.

T cells activation and culture. Human PBMCs were isolated by centrifugation of whole blood on Ficol-Paque (GE Healthcare) gradient for 30 minutes (500×g) and were plated on 6 well plates pre-coated with OKTs antibody (2 µg/mL for 2 h at 37° C., washed once with PBS) at concentration $2\times10^6$/mL in RPMI1640 containing 10% FBS and 100 U/mL of recombinant human IL-2 (BioLegend, San Diego, CA). After 72 h, cultures of activated cells were expanded by plating $5\times10^5$/ml in RPMI1640 containing 10% FBS and 100 U/mL of recombinant human IL-2. Cells were cultured for up to 7 days and used for functional experiments.

On cell click chemistry (dbBiTEs). T cells were coated with DBCO-hOKT3 at a concentration of 1 µg/mL per 10ẽcells/mL for 30 minutes on ice and washed once with PBS. DBCO-hOKT3 coated cells were then incubated with azido-M5A-Alexa Fluor 488 at concentration range from 5-20 µg/mL per 10ẽcells/mL for 0.5-4 hours on ice. Cells were washed 1 to 3 times with PBS. The presence of dbBiTE on the surface was checked on a LSRFortessa (BD) and analyzed by FlowJo software (v10).

dbBiTER binding studies. T cells or breast carcinoma MDA-MB-231±CEA cells were coated with 1 µg/mL per 10ẽcells/mL for 30 minutes on ice and washed once with PBS. dbBiTER binding was detected using secondary antibodies anti-mouse-Alexa Fluor 555 and anti-human-Alexa Fluor 647, both at 2 µg/mL and detected by flow cytometry.

On-T-cell generation of dbBiTERs. T cells were coated with OKT3-RNA-S at a concentration of 1 µg/mL per $10^7$ cells/mL for 30 minutes on ice and washed once with PBS. Coated cells were incubated with M5A-RNA-S' at concentration range from 2.5-20 µg/mL per $10^7$ cells/mL for 1-3 hours on ice. Cells were washed once with PBS. The presence of dbBiTER on the surface was detected using secondary antibodies anti-mouse-Alexa Fluor 555 and anti-human-Alexa Fluor 647, both at 2 µg/mL and detected by flow cytometry.

In vitro cytotoxicity assays. GFP expressing target cells were plated on 96-well plates at concentration $10\times10^3$ cells per well in 100 µL of FluoroBrite DMEM medium (Gibco) containing 10% FBS and L-Glutamine. After 3 hours 100 µL of activated T cells coated with solution formed dbBiTERs or on-cell generated dbBiTEs or dbBiTERs were added to target cells in concentrations corresponding to final effector to target ratios of 10:1, 5:1, 2.5:1 and 1.25:1. Controls with uncoated or anti-CD3 coated T cells were used at the same ratios. Cells were co-incubated for 18 hours at 37° C. followed by analysis of GFP positive cells on a CLARO star plate reader after replacement of culture media with fresh FluoroBrite DMEM medium. Cytotoxicity was calculated using formula:

$$\% \text{ cell cytotoxicity} = \left(1 - \frac{value_{exp} - value_{min}}{value_{max} - value_{min}}\right) \times 100\%$$

Where $value_{exp}$ corresponded to fluorescence for each well co-cultured effector and target cells, $value_{max}$ was fluorescence readings of target cells cultured without any T cells and $value_{min}$ was for medium background. For T cells coated with OKT3-RNA-S and then co-incubated with target tumor cells coated with M5A-RNA-S', the same effector to target ratios were used as described above. In some experiments, the concentration of IFNγ in the media collected from cytotoxic assay E:T ratios 5:1 and 10:1 were measured using ELISA (ELISA MAX™ Deluxe Set Human IFN-γ, Biolegend).

Transmission electron microscopy. Specimens were absorbed to glow-discharged, carbon-coated 200 mesh EM grids, stained with 1% (w/v) uranyl acetate and images taken on an FEI Tecnai 12 transmission electron microscope equipped with a Gatan OneView CMOS camera. For immunogold staining, cells were fixed in 0.3% glutaraldehyde in PBS overnight, washed 3×5 min in 0.01M PBS, followed by incubation in 50 mM glycine in PBS for 15 min, and stained with Nanogold® anti-mouse IgG (Nanoprobes) diluted 1:100 in PBS for 3 hours at room temperature. The cells were then washed 3×5 min in PBS and 3×5 min in distilled water. HQ Silver enhancement kit (Nanoprobes) for 6 min. The cells were then washed 3×5 min in distilled water, and fixed in 1% glutaraldehyde and post-fixed with 0.5% $OsO_4$ for 20 min and processed through steps of serial dehydration. The cells were embedded and polymerized in Eponate resin. Ultra-thin sections (~70 nm thick) were cut using a Leica Ultra cut UCT ultramicrotome with a diamond knife, picked up on 200 mesh Formvar/carbon coated copper EM grids. Ultra-thin sectoins were stained 1% uranyl acetate and Reynold's lead citrate before imaging on an FEI Tecnai 12 transmission electron microscope equipped with a Gatan Ultrascan 2K CCD camera.

Results

Figure 17A:
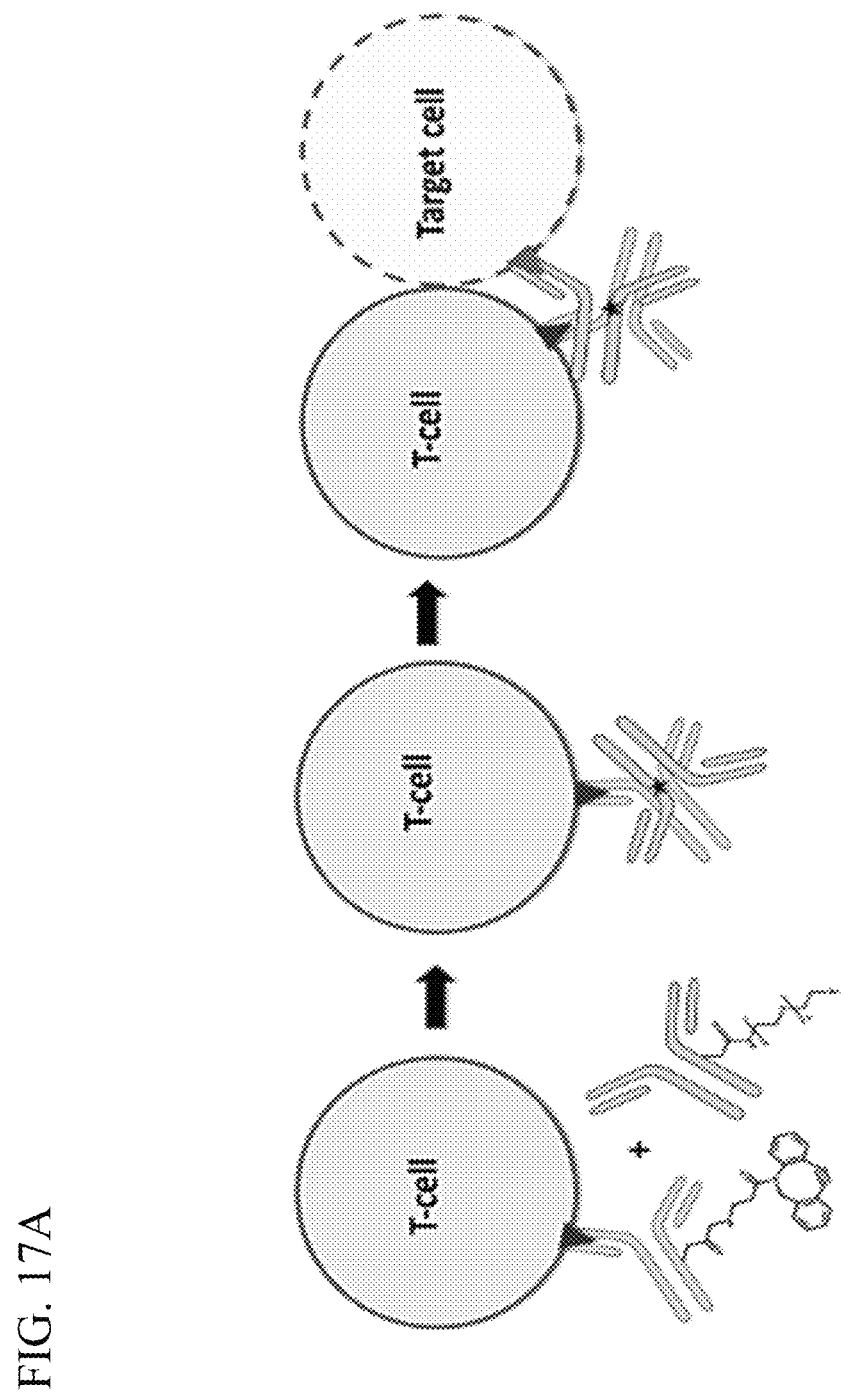
FIGS. 17A-17D. Schematic of cell-click dbBiTE formation on T cells, T cell binding and target cell lysis.
Figure 21A:
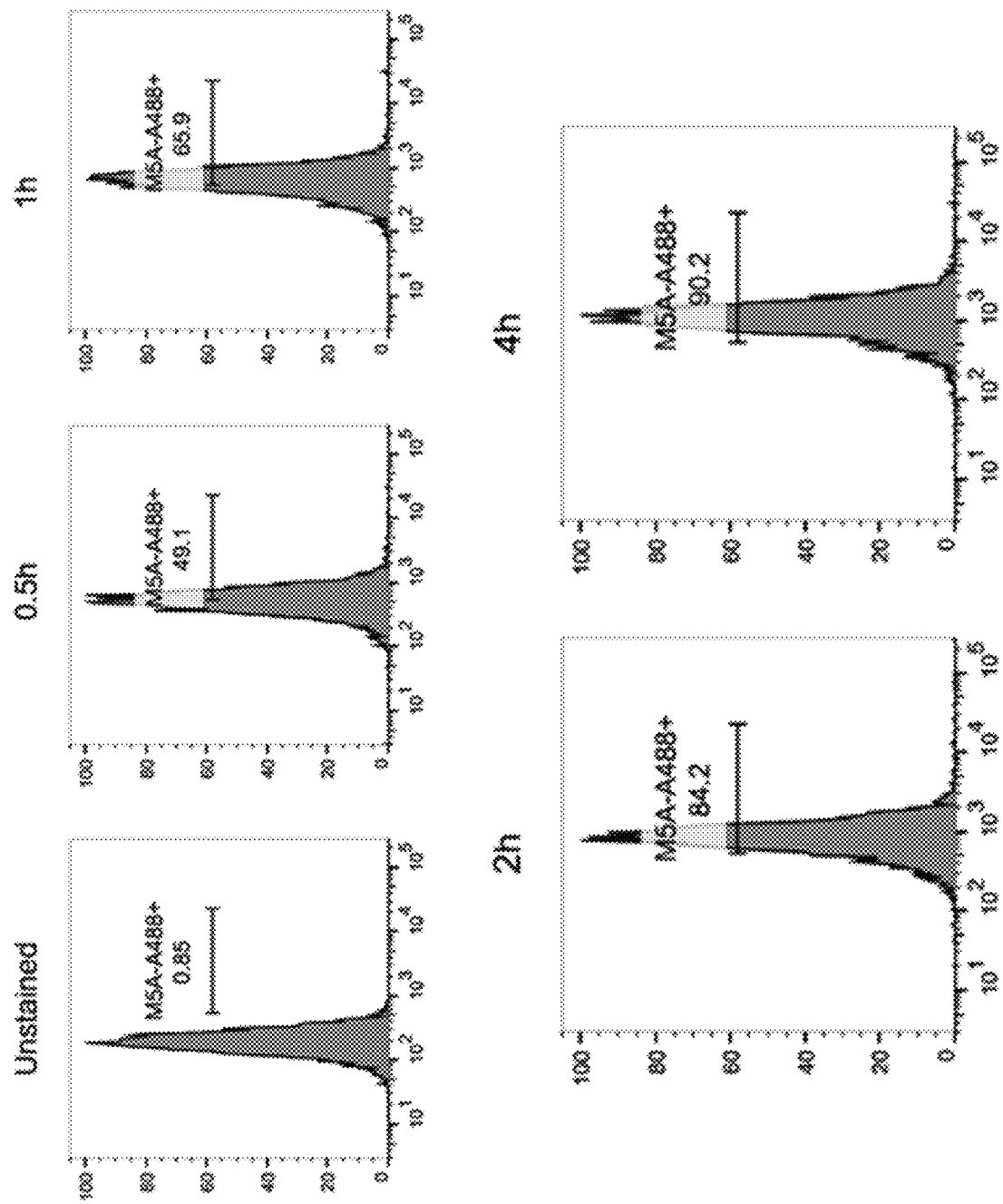
Figure 21B:
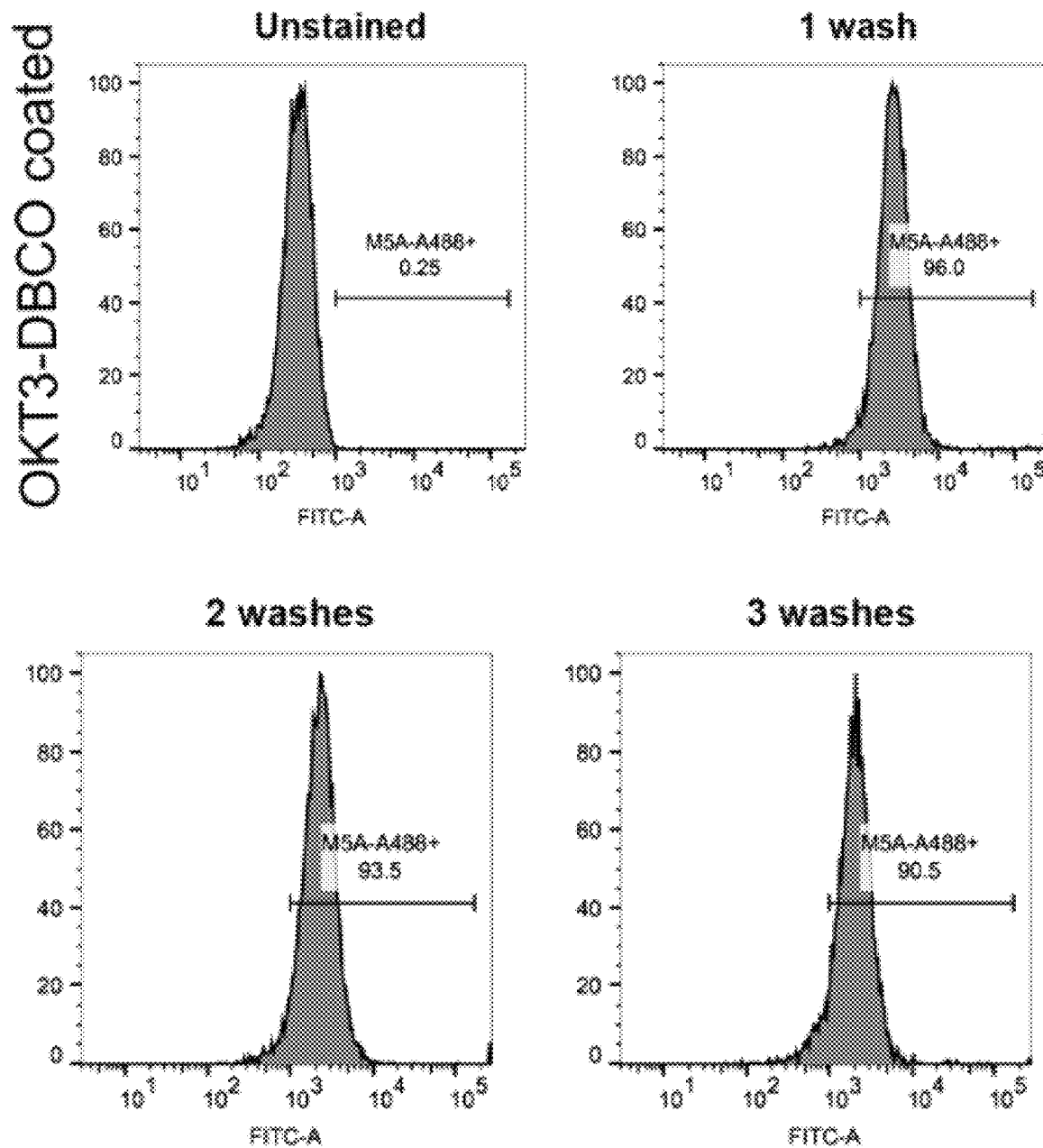
Figure 22A:
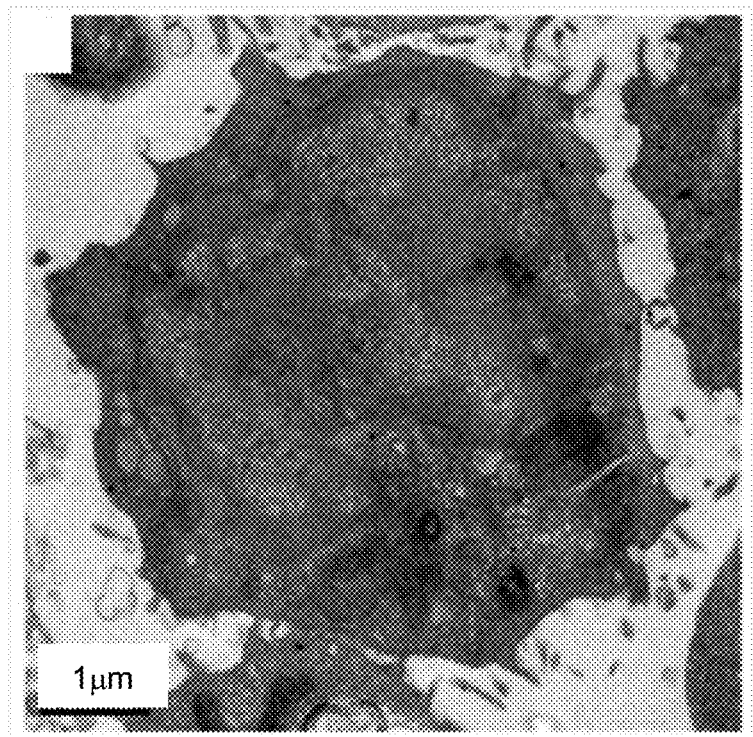
FIGS. 22A-22B. Detection of on-cell generated dbBiTER by immunogold EM. Immunogold-EM analysis of FIG. 22A. control un-coated T cells and FIG. 22B. T cells with on-cell generated dbBiTER. Immunolabeling with Nanogold® anti-mouse IgG and HQ Silver enhancement. 3200× magnification shown.
Figure 22B:
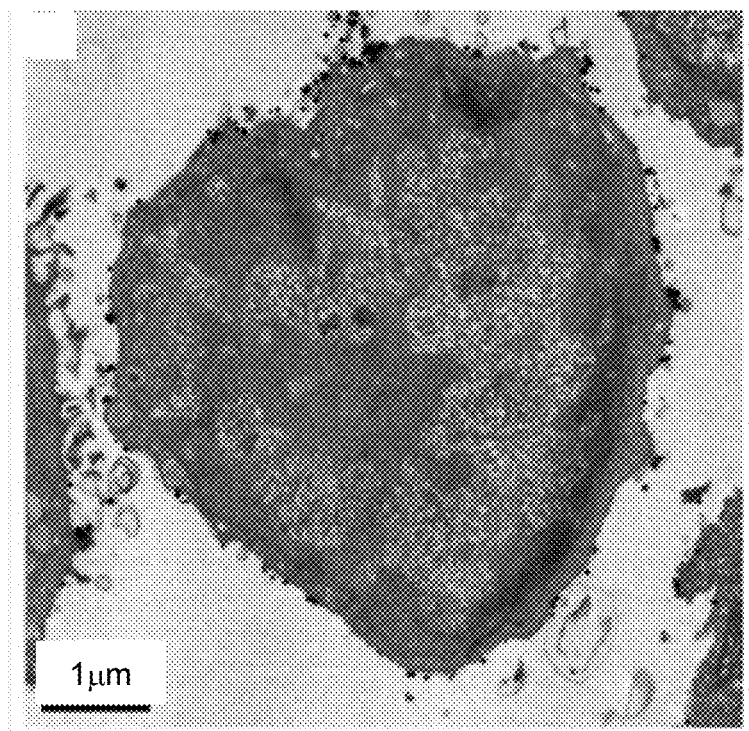

Generation of dbBiTEs on T-cells and re-directed cell lysis. The introduction of the click reagents into the hinge region of the antibodies has been previously described[7]. In that study the dbBiTEs were first generated in solution then incubated with T cells. We now describe the generation of dbBiTEs by sequential incubation of T cells with two Click enabled antibodies, one against hOKT3 (humanized anti-human CD3) conjugated to DBCO, and the second against a target cell (FIG. 17A). The humanized anti-CEA antibody M5A conjugated to a $PEG_4$-azide was chosen to target CEA positive or negative control cells. Azide conjugated M5A was also labeled with Alexa Fluor 488 dye to allow direct detection by flow cytometry since anti-human IgG secondary antibody was used to detect hOKT3 binding prior to the addition of azide-M5A-Alexa Fluor 488. Since there was no background binding of azide-M5A-Alexa 488 to the T-cells before coating with DBCO-OKT3 (uncoated, FIG. 17B) the concentration dependence of the sequential binding of the azide-M5A-Alexa Fluor 488 to precoated T-cells was also followed by flow analysis. The binding of DBCO-hOKT3 was followed with goat anti-human IgG labeled with Alexa Fluor 647. The results demonstrate that the on-cell formation of dbBiTEs at the T-cell surface reached a maximum of 80% at 20 μg/mL per $10^7$ cells/mL at 4° C. for 60 min. All T-cell incubations were performed at 4° C. to minimize internalization of the cell surface bound antibody, since raising the temperature to 37° C. caused binding of azide-M5A-Alexa Fluor 488 by cells not coated with DBCO-OKT3 (data not shown). Concentrations >20 μg/mL did not substantially increase the percentage of positive cells (data not shown). Incubation times >1 h led to maximum binding at 2 h (FIG. 21A). The requirement of sufficient washes with PBS to ensure the specificity of the in situ click reaction on T cells is shown in FIG. 21B.

Figure 17B:
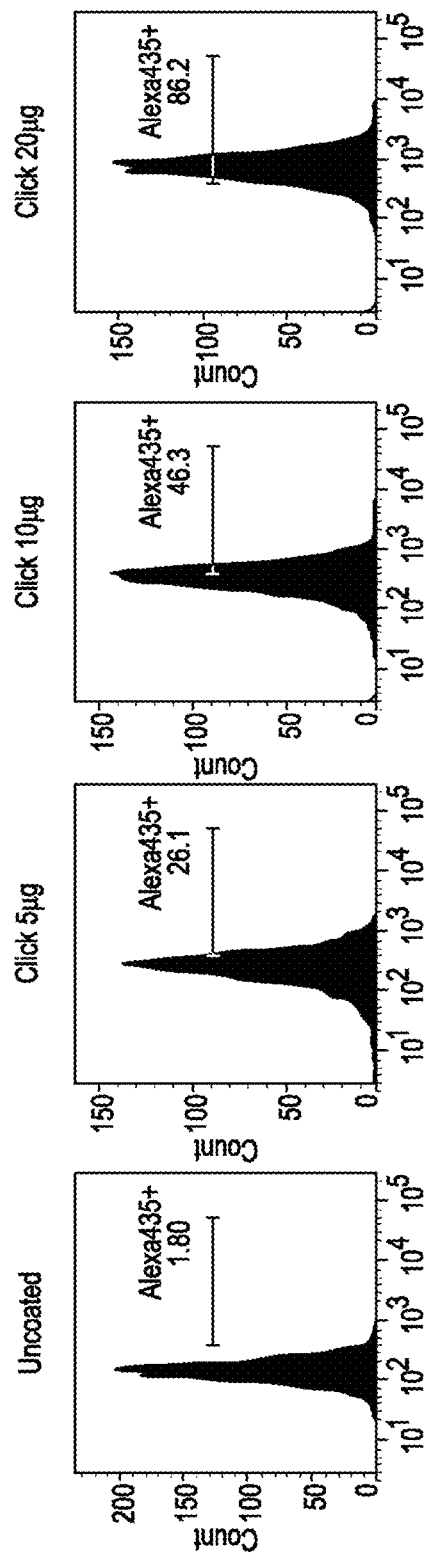
Figure 17C:
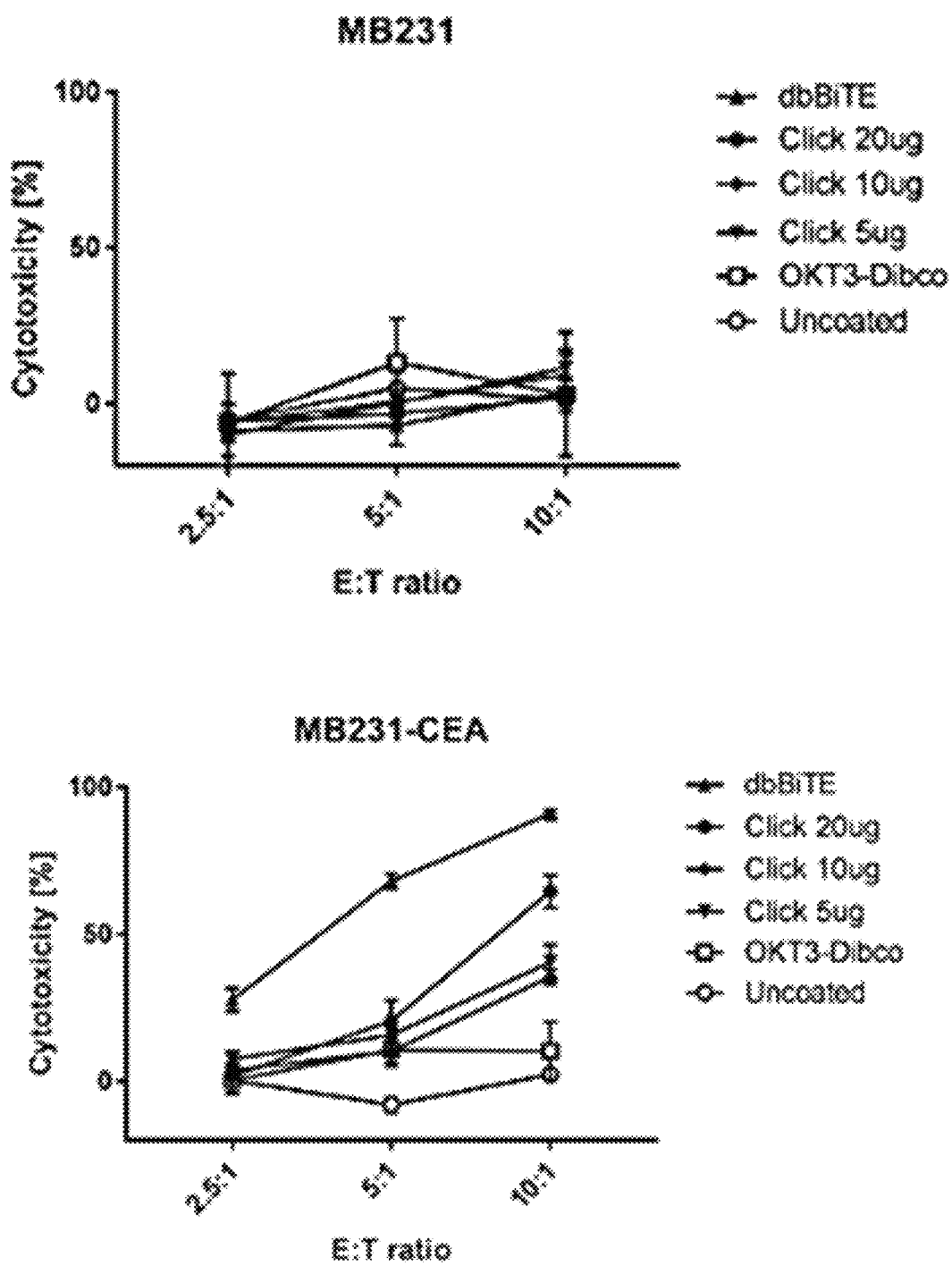
Figure 17D:
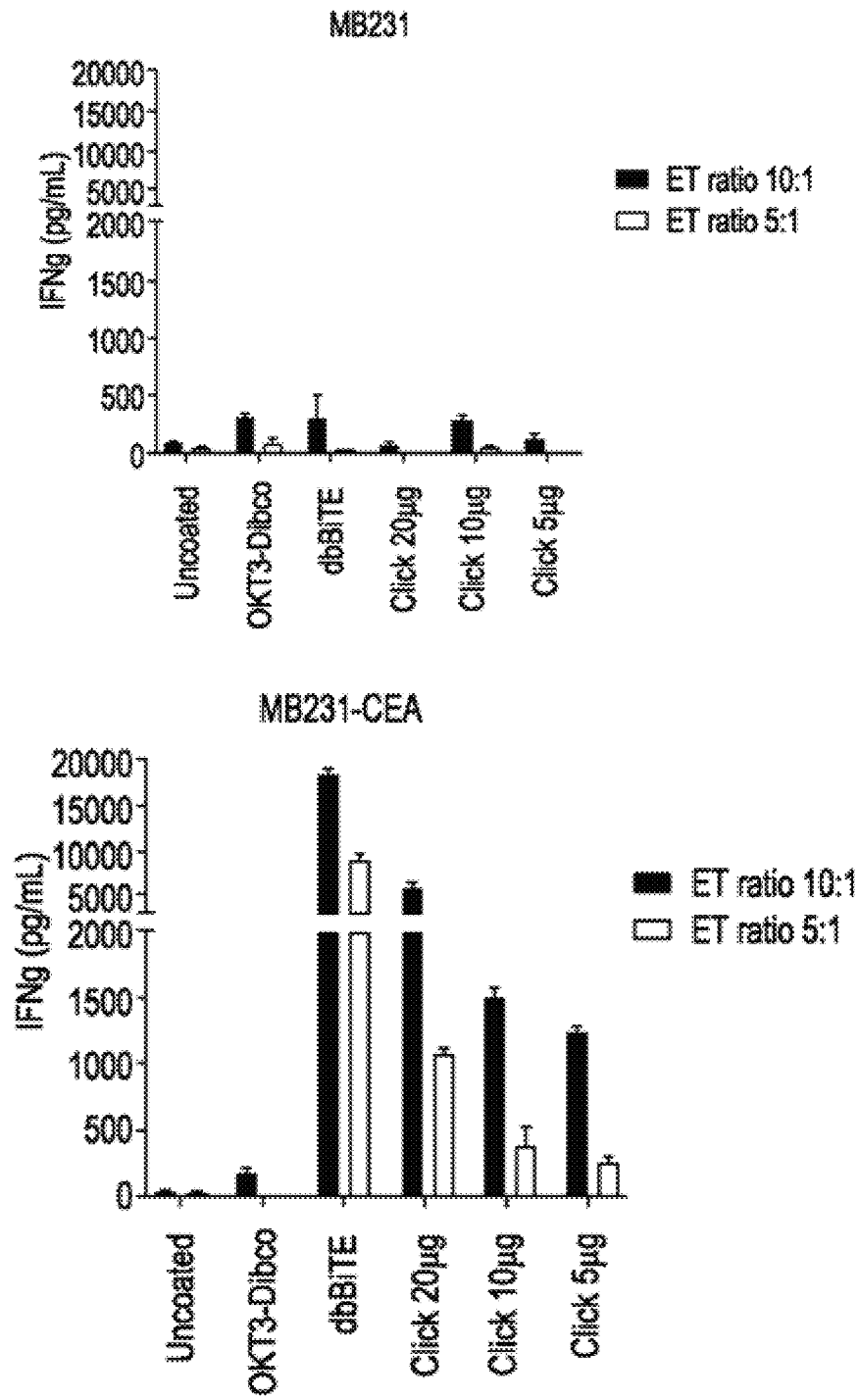

When on-cell generated dbBiTE coated T-cells were compared to T-cells coated with preformed dbBiTEs, both preparations gave specific redirected cell lysis using the CEA negative breast cancer cell line MB231 vs CEA transfected MB231 cells (FIG. 17C). While a dose dependent increase in cytotoxicity was observed for the in situ generated dbBiTE preparation, a maximum of only 60% cell lysis was observed at an E:T of 10:1 compared to 90% for T-cells coated with preformed dbBiTEs at the same E:T. Similarly, the release of IFNγ into the media was higher for T-cells coated with preformed dbBiTEs vs in situ generated dbBiTEs (FIG. 17D).

Figure 18A:
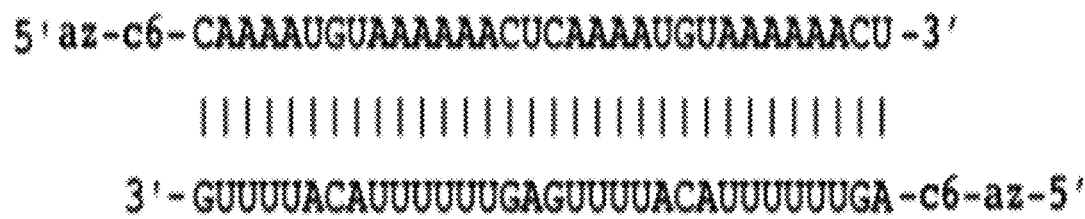
FIGS. 18A-18C. Generation of RNA oligo antibodies by Click chemistry and duplex formation.
Figure 18B:
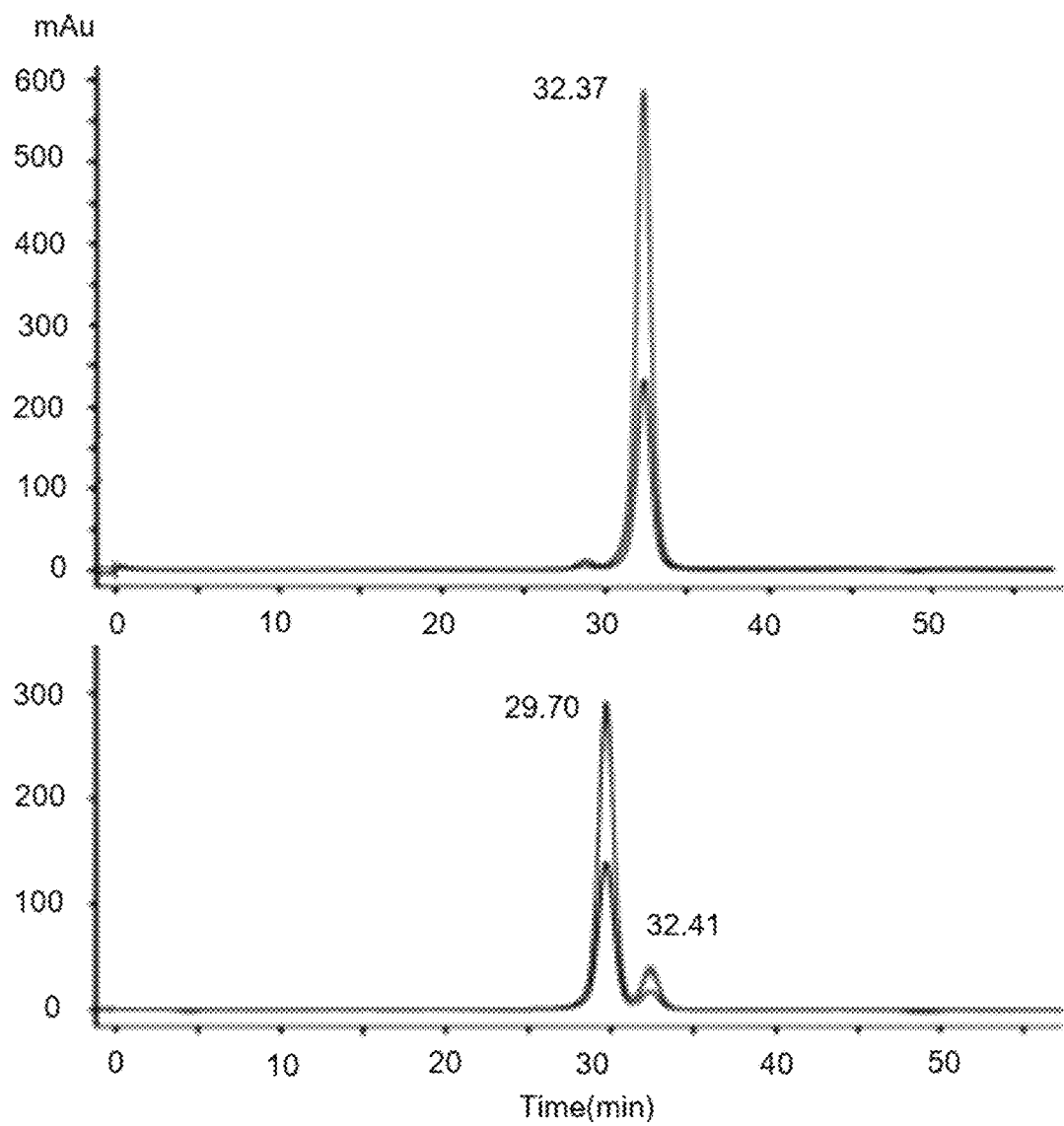
Figure 18C:
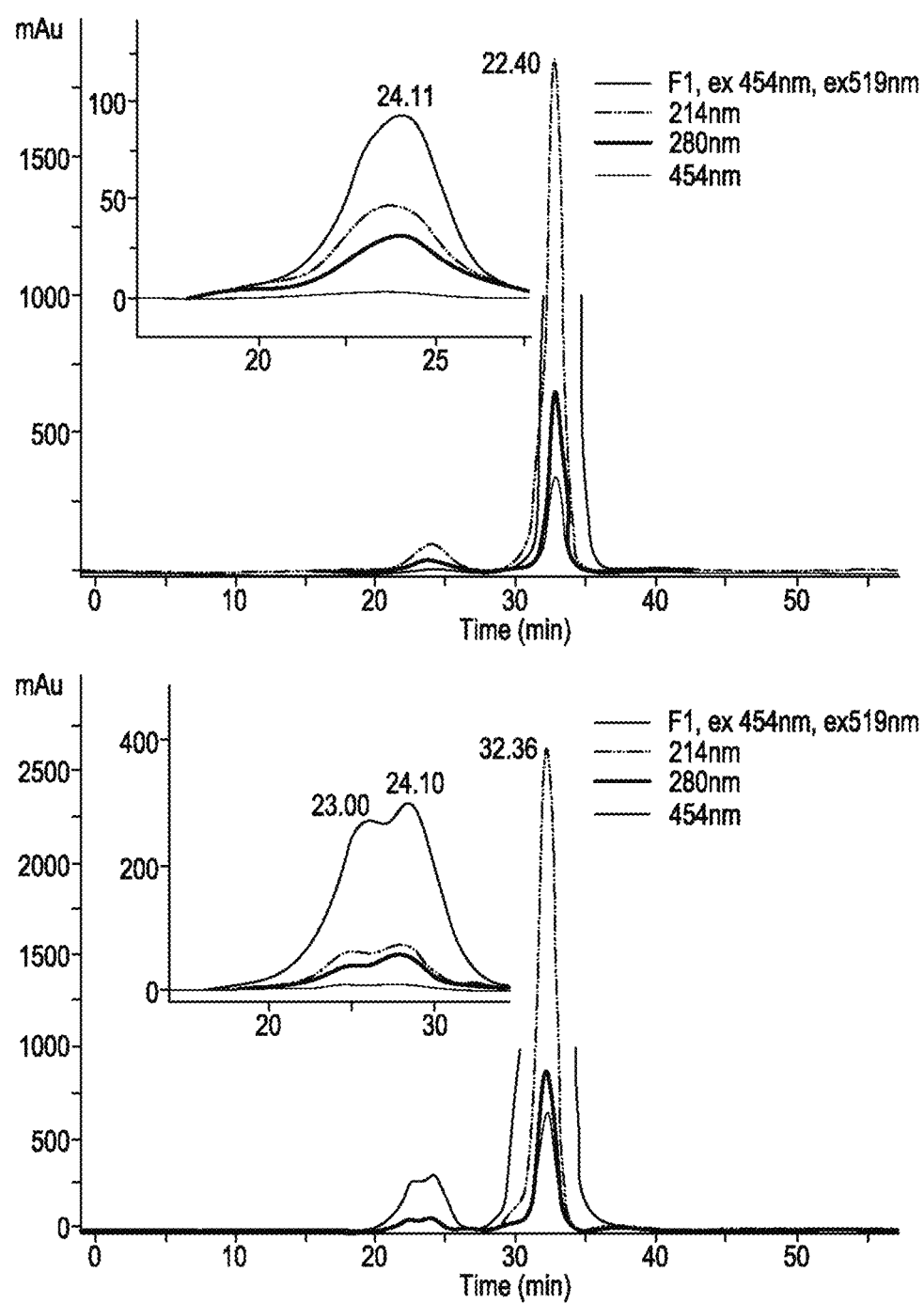

Generation and activity of dbBiTERs. Although the on-cell generation of dbBiTEs on T-cells produced significant re-directed cell lysis, we were interested in further improving the approach by extending the intermolecular reach of the antibody cross-linking agents. Since complementary 2'-OMe-RNA oligonucleotides of varying length can rapidly hybridize at a range of temperatures, we reasoned that conjugation of 2'-OMe-RNA-oligos to the hinge regions of OKTs and M5A would extend both the intermolecular reach and reaction kinetics. In order to optimize the approach, we chose 2'-OMe RNA-oligos for their in vivo stability to nucleases and formation of tighter duplexes than their corresponding DNA duplexes.[18] In terms of length, we chose 32-mers that would have a predicted duplex length of 15 nm, similar to the diameter of an antibody.[19] In addition, the sequence was chosen to minimize hairpin structures that would otherwise compete with duplex formation. As a model system, the 2'-OMe-RNA-oligos were synthesized with 5'-azido linkers so that they could be clicked to antibodies derivatized with DBCO in their hinge regions (FIG. 18A). The ability of two complementary 2'-OMe-RNA-oligos (designated RNA-S and RNA-S') to rapidly form duplexes at 4° C. was demonstrated by size exclusion chromatography (SEC) (FIG. 18B). Once formed, the duplexes were stable at 37° C. for >6 months (data not shown). In order to determine the average number of molecular species generated, two sets of Alexa Fluor 488 labeled oligos were generated using DBCO-Alexa Fluor 488. When an excess of complementary Alexa Fluor 488 labeled 2'-OMe-RNA-oligo was incubated with either OKT3-RNA-S or M5A-RNA-S' and the products separated by SE-HPLC, it was possible to calculate the amount of bound fluorescent probe (FIG. 18C). The results gave a single peak with an average of 2.0 2'-OMe-RNA-oligos per OKT3 and a doublet peak with an average of 2.5 2'-OMe-RNA-oligos per M5A.

Figure 8D:
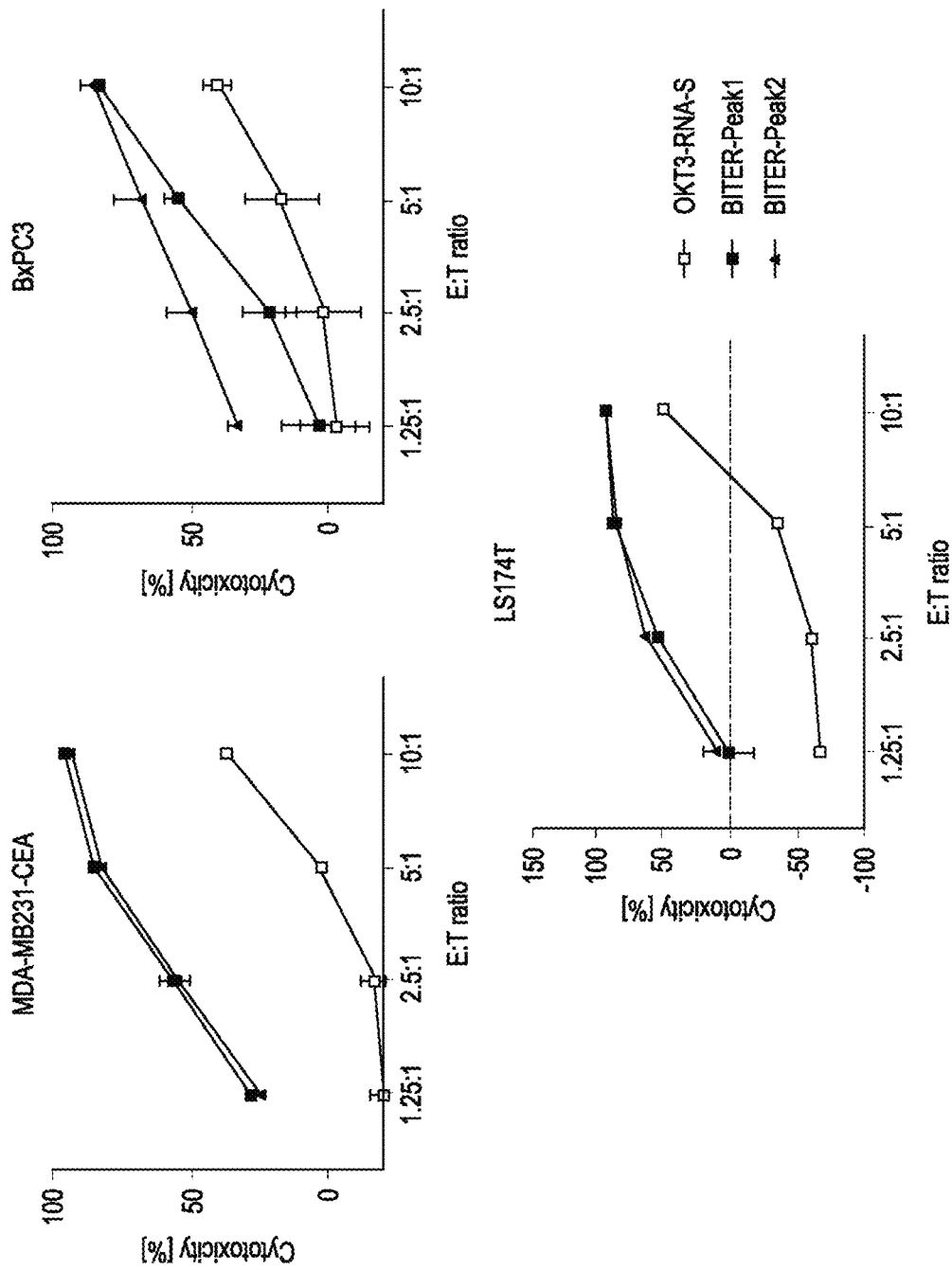

Although the intention of this study was to form dbBiT-ERs on-cell, we also generated dbBiTERs in solution to determine their degree of oligomerization. Since the 2'-OMe-RNA-oligo conjugated antibodies form dbBiTEs by virtue of RNA duplex formation, we named them dbBiT-ERs. When OKT3-RNA-S and M5A-RNA-S' were co-incubated, their crosslinking by duplex formation and purification are shown in FIGS. 5A-5C, 6A-6B. It was clear from the SEC analysis, a method sensitive to Stokes radius or molecular shape, that multiple species of cross-linked products were obtained. Since the number of 2'-OMe-RNA-oligos conjugated to the hinge region can theoretically vary from 0-8 (with an average of 2-4 expected) for an IgG1, the location and number of duplexes is also variable. Thus, it was expected that an ensemble of cross-linked antibodies would form given the variable number of S-oligos incorporated into each antibody hinge region. In order to determine their molecular shapes of the dbBiTERs, transmission electron microscopy (TEM) analysis was performed (FIG. 7). This analysis reveals mostly dimeric species with a variety of antibody-antibody orientations plus evidence for some trimeric and a few more complex species. The molecular shapes are more diverse than those obtained for dbBiTEs[7] in keeping with the more flexible nature of the 2'-OMe-RNA crosslinks. The binding of in solution generated and purified dbBiTERs to cells was followed by flow cytometry using anti-murine IgG to detect OKT3 anti-human IgG to detect M5A, both on T-cells and CEA positive or negative breast cancer cells (FIGS. 8A-8D). Since we purified two peaks of solution generated dbBiTERs by SEC, both were tested revealing that both had specific binding activities (FIGS. 8A-8C). Re-directed cell lysis on three CEA positive cell lines revealed high activity for both peaks of dbBiTERs approaching 100% at an E:T of 10:1 (FIG. 8D).

3.2 On-cell generation of dbBiTERs on T-cells and re-directed cell lysis. In order to determine if the on-cell formation of dbBiTERs was more efficient that on-cell formation of dbBiTEs, we evaluated their formation under similar conditions, namely incubation with OKT3-RNA-S at 1 µg/mL per $10^7$ cells/mL at 4° C. for 30 min followed by M5A-RNA-S' at 20 µg/ml per $10^7$ cells/ml for 2 hr at 4° C. A schema for the on-cell generation of dbBiTERs is shown in FIG. 9A. The results shown in FIG. 9B show that up to 90% cells are positive for M5A vs <1% for controls. However, it should be noted that unlike the on-cell degeneration of dbBiTE on T-cells that required 3 washes at 4° C. prior to reduce background uptake, the dbBiTER T-cells required a single wash. Interestingly, dbBiTERs could be also formed at room temperature and in media containing 10% FBS without any unspecific background interference (data not shown). A possible explanation for the additional washes for in situ formation of dbBiTEs is discussed later. Since it was possible that the in situ formation of dbBiTERs was more efficient than for dbBiTEs, the concentration dependence of their formation was determined. As shown in FIG. 9C, a dose dependent formation of dbBiTER vs control T cells that were not pre-coated with OKT3-C-oligo was found even at 2.5 µg/ml per $10^7$ cells/mL. In terms of re-directed cell lysis, up to 90% cell lysis was found for in situ generated dbBiTERS at either 5 µg/mL or 20 µg/mL at an E:T of 5:1 with cell lysis increasing to 100% at an E:T of 10:1 at which point OKT3 controls begin to show significant cell lysis (FIG. 9D). In order to confirm the presence of the in situ generated dbBiTERs on the cell surface of T-cells, immunogold-EM analysis was performed. The results show positive staining of the dbBiTERs on the cell surface.

Figure 19A:
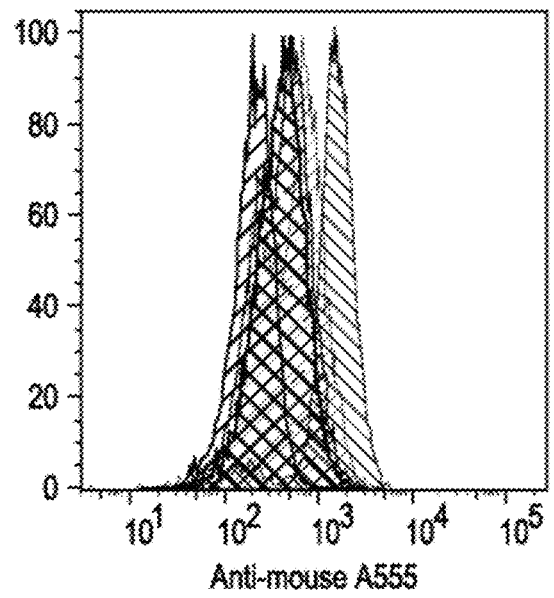
Figure 19B:
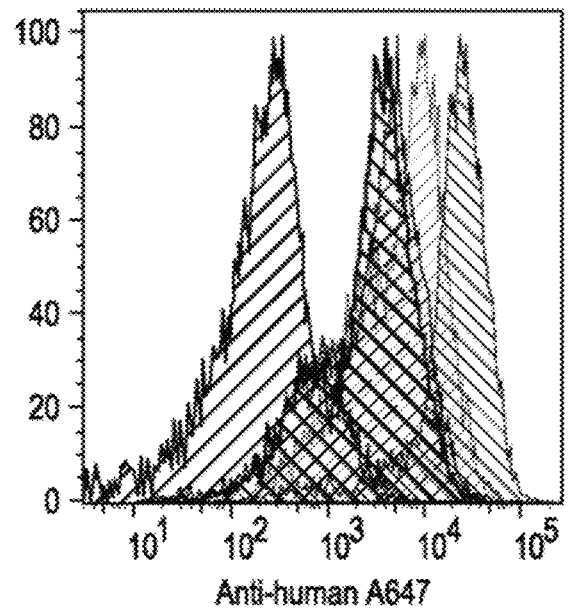
Figure 19C:
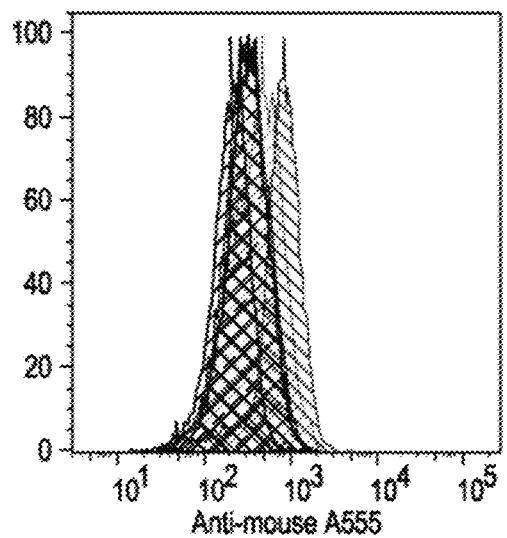
Figure 19D:
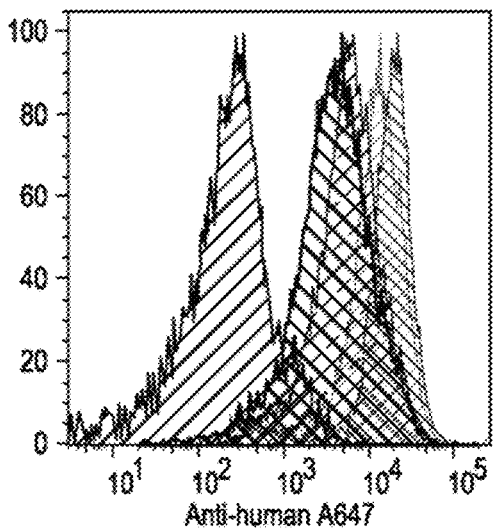

Since internalization may affect the useful lifetime of in situ formed dbBiTERs, we studied the kinetics of their disappearance from the cell surface of T-cells (FIGS. 19A-19E). The results show that T-cells coated with the parent antibody OKT3 internalize rapidly at 37° C. with only 56% cell surface positive T-cells found at 6 hrs (FIG. 19A), while 71% are found on the cell surface for T-cells coated with dbBiTEs (FIG. 19B). Interestingly, T-cells coated with OKT3-RNA-S showed faster internalization with only 39% positive cells after 6 hrs vs in situ formed dbBiTERs that were 82% positive, demonstrating that either dbBiTEs or dbBiTERs internalize more slowly than the parent antibody OKT3 or its 2'-OMe-RNA derivative FIGS. 19C, 19D). Thus, the residence time of in situ generated dbBiTERs is suitable for in vivo studies.

Figure 20A:
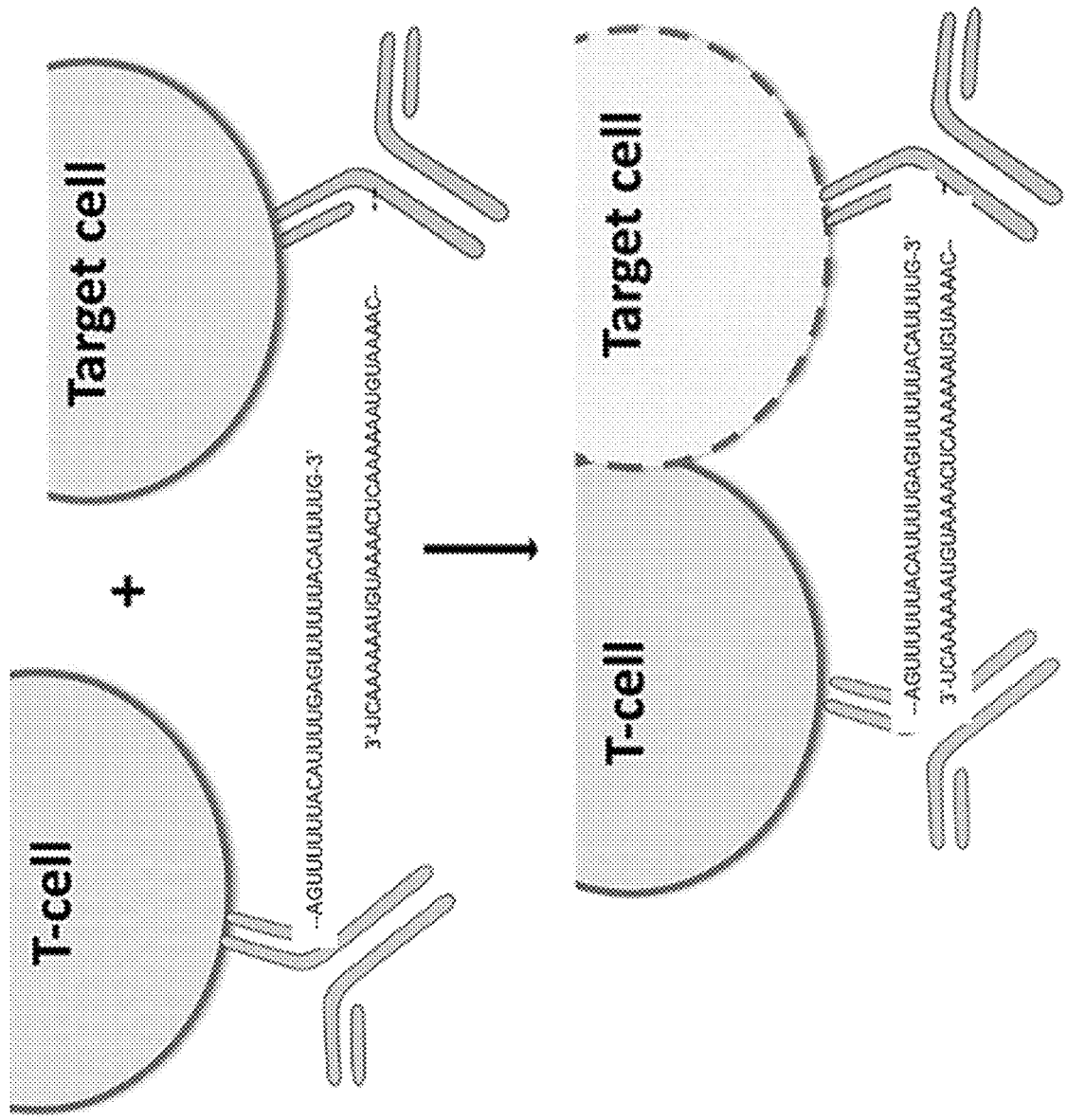
FIGS. 20A-20B. Cell to cell generation of dbBiTERs.

Cell to cell generation of dbBiTERs. Since T-cells coated with dbBiTERs kill uncoated target cells, we explored the option of OKT3-RNA-S precoated T-cells to kill M5A-RNA-S' precoated targeted cells. The schema for this approach is shown in FIG. 20A and the results in FIG. 20B. When the two precoated cells are mixed, a dose dependent increase in cytotoxicity is observed with about 75% cytotoxicity at an E:T of 10:1 vs 10% for uncoated controls or precoated target controls with M5A that cannot form duplexes. Similar to observations shown in FIG. 9D, a lesser but significant dose response was observed for OKT3-RNA-S coated T-cells against uncoated target cells (about 50% cytotoxicity at an E:T of 10:1).

Discussion

The generation of a potent T-cell response to tumor antigens, that are inherently self-antigens that are over-expressed in tumor vs normal tissue can be achieved by a redirected T-cell response such as bispecific antibodies in which one specificity is directed at the T-cell and the other at the tumor antigen. CEA is a good example of a tumor antigen that is highly expressed in solid tumors vs normal tissue,[20] but naked antibodies to CEA have little or no cytotoxic activity.[21-22] This lack of intrinsic cytotoxic activity can be overcome by generating a bispecific T-cell engager (BiTE) based on the parent antibodies to CD3 and anti-CEA. Although several anti-CEA BiTEs have been generated from scFvs,[23-26] their utility depends on genetic constructs that produce monovalent binding to CD3 and CEA. An alternative to genetically engineering a BiTE is to chemical cross-link the parent antibodies that retain their inherent avidity to the target antigens. The major limitation to the chemical cross-linking approach is low yields of the fully active desired product. Recently, we have shown that chemical modification of the antibody pairs in their hinge regions with paired click reagents can lead to the successful production of a 300 kDa bispecific antibody known as a dual specific bivalent BiTE or dbBiTE.[7] Although we demonstrated potent in vitro and in vivo redirected cell lysis for the dbBiTE, we thought that the requirement to purify the 300 kDa species away from the monomeric 150 kDa species was a potential bottleneck. We addressed this issue by generating the dbBiTE directly on the cell surface of the T cell.

The concept of performing click chemistry at a cell surface has precedent. For example, incorporation of azido-labeled sugars into cell surface glycoproteins enable click chemistry of paired reagents bearing various reporters.[27-29] The variety of small molecules that have been cell surface clicked is extensive[30] and includes targeting of antibodies bearing click reagent pairs to cells followed by click enable small molecules.[31-33] In our study we considered the possibility that two antibodies, one T cell specific and one tumor cell specific, bearing click reagent pairs would enable redirected cytotoxicity. Thus, we were asking if click chemistry could efficiently occur on the cell surface between two antibodies bearing click reagents. As depicted in FIG. 17B, incubation of T cells with 1 µg/mL of DBCO-hOKT3, the amount necessary to label >90% of the cells followed by incubation with 20 µg/mL azido-M5A, generated fully functional dbBiTEs on the surface of the T cell. Although encouraging, we concluded that the efficiency of the azido-DBCO click pair between antibodies was inherently inefficient and required a long incubation time and extensive washing.

Based on our previous work we knew that the click reaction between two antibodies bearing click reagents in their hinge regions required that the antibodies approach each other in a conformationally restricted manner, namely at their hinge regions.[7] Given the overall surface area of an antibody compared to the accessible hinge region, we estimated that this constraint would reduce the proper contact by at least a factor of 3, accounting for the majority of the reduction in the on cell click reaction. To improve the odds of an on-cell contact to enable the clicking of the reagent pairs, we considered that either the click reagents needed to be extended further from the antibody hinge region or that another complementary joining method should be employed. In consideration of the first approach, extending the reach of the click reagents beyond the hinge region, we discarded the idea of labeling antibody surface residues, since that approach suffers from loss of specificity if random lysine residues are labeled, and requires re-engineering the antibody if new surface residues are introduced. Extending the reach of the click reagents by tethering them to long linkers such as PEGs was also undesirable since the PEG oligomers >4 tend to fold into compact shapes,[34] negating their ability to distance the click reagents from the hinge region.

Since antibody-oligonucleotide conjugates have been extensively validated for their ability to form duplexes with their complementary counterparts,[35] we considered the following approach: conjugate oligo pairs to the hinge regions of two antibodies by efficient click chemistry and test their ability to form stable duplexes under mild conditions. We chose 2'OMe-RNA oligos for their advantages over DNA or RNA in terms of the formation of stable duplex formation and resistance to nuclease attack.[18] The extended length of the 2'OMe-RNA (FIG. 18A) was chosen to be at least 10-15 nm, based on the actual dimension of an antibody molecule[19]. Since the idea was to extend the dbBiTE technology to RNA guided duplex formation, we called the improved approach dbBiTER. We then showed that the click-based conjugation of azido-oligos to DBCO-Abs was efficient and formed stable conjugates under mild conditions (FIGS. 18B, 5A-5C, and 6A-6B). It should be noted that since at least two oligos per antibody was found (FIG. 18C), the formation of bispecific species with molecular sizes >300 kDa were isolated. In spite of the range in molecular size, we assumed that the binding to cell surfaces would not be affected and that the increased number of 2'OMe-RNAs would favor efficient duplex formation not only in solution but also at the cell surface level. In both cases, the formation of dbBiTERs was very fast and could be performed at low temperatures compatible for cells. In contrast to in situ generation of dbBiTEs, in situ generation of dbBiTERs required much lower concentrations of anti-CEA antibody with shorter incubation times and less wash steps to remove excess antibody. Moreover, on-cell generation of dbBiTERs resulted in far better antigen specific cytotoxic responses observed also for lower concentrations of antibodies. Interestingly, dbBiTERs generation at the cell surface significantly slowed the process of internalization making more available for cytotoxic synapse formation. Furthermore, we predict that the presence of oligos on dbdbBiTERs at the surface of T cells, would allow multiplexing by duplex formation with other antigen specific antibodies bearing complementary oligos.

Figure 20B:
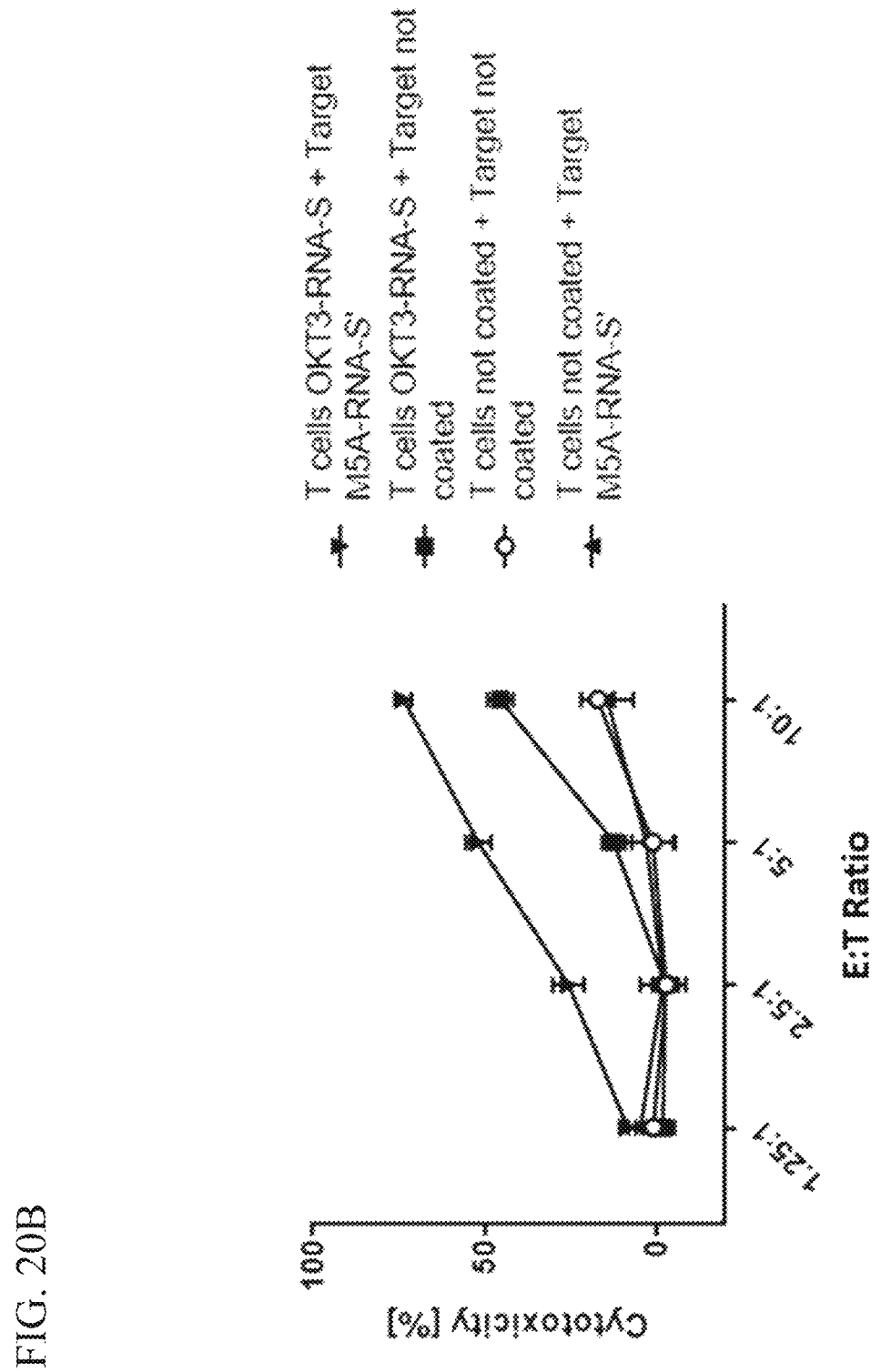

The improved efficiency of cell based dbBiTERs over cell based dbBiTEs prompted us to consider the possibility that the antibody targeting reagents could be coated onto separate cells, allowing the separation of the coating steps. The concept and validation are shown in FIGS. 20A-20B. Since tumor cells are intrinsic to the host, while T cells can be isolated, coated ex vivo and re-infused, the advantage to this approach to cancer therapy is not immediately obvious. However, we envision that a modification of this approach could be used to separate the dbBiTER steps in treatment strategies where infusion steps need to be separated in time.

REFERENCES

[1] K. Garber, Bispecific antibodies rise again. *Nat Rev Drug Discov* 2014, 13, 799-801.

[2] A. F. Labrijn, M. L. Janmaat, J. M. Reichert, P. Parren, Bispecific antibodies: a mechanistic review of the pipeline. *Nat Rev Drug Discov* 2019, 18, 585-608.

[3] M. Zhu, B. Wu, C. Brandl, J. Johnson, A. Wolf, A. Chow, S. Doshi, Blinatumomab, a Bispecific T-cell Engager (BiTE((R))) for CD-19 Targeted Cancer Immunotherapy: Clinical Pharmacology and Its Implications. *Clin Pharmacokinet* 2016, 55, 1271-1288.

[4] F. V. Suurs, M. N. Lub-de Hooge, E. G. E. de Vries, D. J. A. de Groot, A review of bispecific antibodies and antibody constructs in oncology and clinical challenges. *Pharmacol Ther* 2019, 201, 103-119.

[5] C. Klein, W. Schaefer, J. T. Regula, C. Dumontet, U. Brinkmann, M. Bacac, P. Umana, Engineering therapeutic bispecific antibodies using CrossMab technology. *Methods* 2019, 154, 21-31.

[6] M. B. Moreno, J. A. Titus, M. S. Cole, J. Y. Tso, N. Le, C. H. Paik, T. Bakacs, C. M. Zacharchuk, D. M. Segal, J. R. Wunderlich, Bispecific antibodies retarget murine T cell cytotoxicity against syngeneic breast cancer in vitro and in vivo. *Cancer Immunol Immunother* 1995, 40, 182-190.

[7] M. Kujawski, L. Li, S. Bhattacharya, P. Wong, W. H. Lee, L. Williams, H. Li, J. Chea, K. Poku, N. Bowles, N. Vaidehi, P. Yazaki, J. E. Shively, Generation of dual specific bivalent BiTEs (dbBIspecific T-cell engaging antibodies) for cellular immunotherapy. *BMC Cancer* 2019, 19, 882.

[8] S. I. Rudnick, G. P. Adams, Affinity and avidity in antibody-based tumor targeting. *Cancer Biother Radiopharm* 2009, 24, 155-161.

[9] J. K. Chan, C. A. Hamilton, M. K. Cheung, M. Karimi, J. Baker, J. M. Gall, S. Schulz, S. H. Thome, N. N. Teng, C. H. Contag, L. G. Lum, R. S. Negrin, Enhanced killing of primary ovarian cancer by retargeting autologous cytokine-induced killer cells with bispecific antibodies: a preclinical study. *Clin Cancer Res* 2006, 12, 1859-1867.

[10] J. M. Gall, P. A. Davol, R. C. Grabert, M. Deaver, L. G. Lum, T cells armed with anti-CD3×anti-CD20 bispecific antibody enhance killing of CD20+ malignant B cells and bypass complement-mediated rituximab resistance in vitro. *Exp Hematol* 2005, 33, 452-459.

[11] P. A. Davol, J. A. Smith, N. Kouttab, G. J. Elfenbein, L. G. Lum, Anti-CD3×anti-HER2 bispecific antibody effectively redirects armed T cells to inhibit tumor development and growth in hormone-refractory prostate cancer-bearing severe combined immunodeficient beige mice. *Clin Prostate Cancer* 2004, 3, 112-121.

[12] U. Reusch, M. Sundaram, P. A. Davol, S. D. Olson, J. B. Davis, K. Demel, J. Nissim, R. Rathore, P. Y. Liu, L. G. Lum, Anti-CD3×anti-epidermal growth factor receptor (EGFR) bispecific antibody redirects T-cell cytolytic activity to EGFR-positive cancers in vitro and in an animal model. *Clin Cancer Res* 2006, 12, 183-190.

[13] I. M. Zitron, A. Thakur, O. Norkina, G. R. Barger, L. G. Lum, S. Mittal, Targeting and killing of glioblastoma with activated T cells armed with bispecific antibodies. *BMC Cancer* 2013, 13, 83.

[14] A. Holzinger, M. Barden, H. Abken, The growing world of CAR T cell trials: a systematic review. *Cancer Immunol Immunother* 2016, 65, 1433-1450.

[15] A. Thakur, M. Huang, L. G. Lum, Bispecific antibody based therapeutics: Strengths and challenges. *Blood Rev* 2018, 32, 339-347.

[16] A. Thakur, L. G. Lum, S. Mittal, Bispecific Antibody Armed T Cells to Target Cancer Cells. *Methods Mol Biol* 2018, 1722, 117-126.

[17] P. J. Yazaki, M. A. Sherman, J. E. Shively, D. Ikle, L. E. Williams, J. Y. Wong, D. Colcher, A. M. Wu, A. A. Raubitschek, Humanization of the anti-CEA T84.66 antibody based on crystal structure data. *Protein Eng Des Sel* 2004, 17, 481-489.

[18] M. Majlessi, N. C. Nelson, M. M. Becker, Advantages of 2'-O-methyl oligoribonucleotide probes for detecting RNA targets. *Nucleic Acids Res* 1998, 26, 2224-2229.

[19] E. O. Saphire, R. L. Stanfield, M. D. Crispin, G. Morris, M. B. Zwick, R. A. Pantophlet, P. W. Parren, P. M. Rudd, R. A. Dwek, D. R. Burton, I. A. Wilson, Crystal structure of an intact human IgG: antibody asymmetry, flexibility, and a guide for HIV-1 vaccine design. *Adv Exp Med Biol* 2003, 535, 55-66.

[20] C. Hall, L. Clarke, A. Pal, P. Buchwald, T. Eglinton, C. Wakeman, F. Frizelle, A Review of the Role of Carcinoembryonic Antigen in Clinical Practice. *Ann Coloproctol* 2019, 35, 294-305.

[21] X. Xu, P. Clarke, G. Szalai, J. E. Shively, L. E. Williams, Y. Shyr, E. Shi, F. J. Primus, Targeting and therapy of carcinoembryonic antigen-expressing tumors in transgenic mice with an antibody-interleukin 2 fusion protein. *Cancer Res* 2000, 60, 4475-4484.

[22] S. E. Cha, M. Kujawski, J. Y. P, C. Brown, J. E. Shively, Tumor regression and immunity in combination therapy with anti-CEA chimeric antigen receptor T cells and anti-CEA-IL2 immunocytokine. *Oncoimmunology* 2021, 10, 1899469.

[23] M. Bacac, T. Fauti, J. Sam, S. Colombetti, T. Weinzierl, D. Ouaret, W. Bodmer, S. Lehmann, T. Hofer, R. J. Hosse, E. Moessner, O. Ast, P. Bruenker, S. Grau-Richards, T. Schaller, A. Seidl, C. Gerdes, M. Perro, V. Nicolini, N. Steinhoff, S. Dudal, S. Neumann, T. von Hirschheydt, C. Jaeger, J. Saro, V. Karanikas, C. Klein, P. Umana, A Novel Carcinoembryonic Antigen T-Cell Bispecific Antibody (CEA TCB) for the Treatment of Solid Tumors. *Clin Cancer Res* 2016, 22, 3286-3297.

[24] M. D. Oberst, S. Fuhrmann, K. Mulgrew, M. Amann, L. Cheng, P. Lutterbuese, L. Richman, S. Coats, P. A. Baeuerle, S. A. Hammond, CEA/CD3 bispecific antibody MEDI-565/AMG 211 activation of T cells and subsequent killing of human tumors is independent of mutations commonly found in colorectal adenocarcinomas. *MAbs* 2014, 6, 1571-1584.

[25] R. Gonzalez-Exposito, M. Semiannikova, B. Griffiths, K. Khan, L. J. Barber, A. Woolston, G. Spain, K. von Loga, B. Challoner, R. Patel, M. Ranes, A. Swain, J. Thomas, A. Bryant, C. Saffery, N. Fotiadis, S. Guettler, D. Mansfield, A. Melcher, T. Powles, S. Rao, D. Watkins, I. Chau, N. Matthews, F. Wallberg, N. Starling, D. Cunningham, M. Gerlinger, CEA expression heterogeneity and plasticity confer resistance to the CEA-targeting bispecific immunotherapy antibody cibisatamab (CEA-TCB) in patient-derived colorectal cancer organoids. *J Immunother Cancer* 2019, 7, 101.

[26] L. Peng, M. D. Oberst, J. Huang, P. Brohawn, C. Morehouse, K. Lekstrom, P. A. Baeuerle, H. Wu, Y. Yao, S. R. Coats, W. Dall'Acqua, M. Damschroder, S. A. Hammond, The CEA/CD3-bispecific antibody MEDI-565 (MT111) binds a nonlinear epitope in the full-length but not a short splice variant of CEA. *PLoS One* 2012, 7, e36412.

[27] J. A. Prescher, D. H. Dube, C. R. Bertozzi, Chemical remodelling of cell surfaces in living animals. *Nature* 2004, 430, 873-877.

[28] A. A. Neves, H. Stockmann, Y. A. Wainman, J. C. Kuo, S. Fawcett, F. J. Leeper, K. M. Brindle, Imaging cell surface glycosylation in vivo using "double click" chemistry. *Bioconjug Chem* 2013, 24, 934-941.

[29] W. Chen, J. M. Smeekens, R. Wu, Systematic and site-specific analysis of N-sialoglycosylated proteins on the cell surface by integrating click chemistry and MS-based proteomics. *Chem Sci* 2015, 6, 4681-4689.

[30] Y. Takayama, K. Kusamori, M. Nishikawa, Click Chemistry as a Tool for Cell Engineering and Drug Delivery. *Molecules* 2019, 24.

[31] R. Rossin, P. R. Verkerk, S. M. van den Bosch, R. C. Vulders, I. Verel, J. Lub, M. S. Robillard, In vivo chemistry for pretargeted tumor imaging in live mice. *Angew Chem Int Ed Engl* 2010, 49, 3375-3378.

[32] B. M. Zeglis, K. K. Sevak, T. Reiner, P. Mohindra, S. D. Carlin, P. Zanzonico, R. Weissleder, J. S. Lewis, A pretargeted PET imaging strategy based on bioorthogonal Diels-Alder click chemistry. *J Nucl Med* 2013, 54, 1389-1396.

[33] R. Rossin, R. M. Versteegen, J. Wu, A. Khasanov, H. J. Wessels, E. J. Steenbergen, W. Ten Hoeve, H. M. Janssen, A. van Onzen, P. J. Hudson, M. S. Robillard, Chemically triggered drug release from an antibody-drug conjugate leads to potent antitumour activity in mice. *Nat Commun* 2018, 9, 1484.

[34] Y. Lu, S. E. Harding, A. Turner, B. Smith, D. S. Athwal, J. G. Grossmann, K. G. Davis, A. J. Rowe, Effect of PEGylation on the solution conformation of antibody fragments. *J Pharm Sci* 2008, 97, 2062-2079.

[35] I. Dovgan, O. Koniev, S. Kolodych, A. Wagner, Antibody-Oligonucleotide Conjugates as Therapeutic, Imaging, and Detection Agents. *Bioconjug Chem* 2019, 30, 2483-2501.

INFORMAL SEQUENCE LISTING

SEQ ID NO:1 JSMK-8721 32-mer (sense)
5'-/5AzideC6/mAmGmU mUmUmU mUmUmA mCmAmU mUmUmU mGmAmG mUmUmU mUmUmU mAmCmA mUmUmU mUAmG/3AmMC6/-3'

SEQ ID NO:2 JSMK-8735 (antisense)
5'-/5AzideC6/mCmAmA mAmAmU mGmUmA mAmAmA mAmAmC mUmCmA mAmAmA mUmGmU mAmAmA mAmAmA mCmU/3AmMC6/-3'

Primary Sequence
SEQ ID NO: 3
5'-CAAAAUGUAAAAAACUCAAAAUGUAAAAAACU-3'

Secondary Sequence
SEQ ID NO: 4
5'-AGUUUUUUACAUUUUGAGUUUUUUACAUUUUG-3'

JSMK4231(4) azido
SEQ ID NO: 5
5'-/5AzideN//iSpC3//iSpC3//iSpC3/mAmUmU mGmGmA mUmUmA mCmAmG mAmCmA mCmUmU mUmAmC mAmCmU mUmAmC mAmCmU mUmU/3aminoC6/-3'

JSMK4335 azido
SEQ ID NO: 6
5'-/5AzideN//iSpC3//iSpC3//iSpC3/mAmAmA mGmUmG mUmAmA mGmUmG mUmAmA mAmGmU mGmUmC mUmGmU mAmAmU mCmCmA mAmU-3'

What is claimed is:

1. A pharmaceutical kit comprising:
   (i) a first dosage form comprising a first antibody covalently attached to a first oligoribonucleotide through a first chemical linker and a pharmaceutically acceptable excipient; and
   (ii) a second dosage form comprising a second antibody covalently attached to a second oligoribonucleotide through a second chemical linker and a pharmaceutically acceptable excipient
   wherein said first oligoribonucleotide has the sequence of SEQ ID NO:1, or wherein said second oligoribonucleotide has the sequence of SEQ ID NO:2.

2. The kit of claim 1, wherein said first antibody is an effector antigen-binding antibody, and wherein the second antibody is a target antigen-binding antibody.

3. The kit of claim 1, wherein the first chemical linker is attached to the hinge region of the first antibody, and the second chemical linker is attached to the hinge region of the second antibody.

4. The kit of claim 1, wherein said first dosage form comprises more than one antibody, wherein each of said more than one antibodies is different or the same.

5. The kit of claim 1, wherein said first oligoribonucleotide and said second oligoribonucleotide have a sequence complementarity of at least 85% over at least 20 continuous nucleotides.

6. The kit of claim 1, wherein said first oligoribonucleotide and said second oligoribonucleotide independently comprise one or more nucleobase analogs.

7. The kit of claim 1, wherein said first oligoribonucleotide has the sequence of SEQ ID NO: 1, and wherein said second oligoribonucleotide has the sequence of SEQ ID NO:2.

8. The kit of claim 1, wherein said first oligoribonucleotide or said second oligoribonucleotide independently do not comprise a phosphorothioate moiety.

9. The kit of claim 1, wherein said first dosage form comprises a cell bound to said first antibody and a pharmaceutically acceptable excipient, and wherein said cell is an effector cell or a target cell.

10. A pharmaceutical composition comprising a therapeutically effective amount of a cell composition comprising a cell bound to a first antibody covalently attached to a first oligoribonucleotide through a first chemical linker and a pharmaceutically acceptable excipient, wherein said first oligoribonucleotide has the sequence of SEQ ID NO:1.

11. The pharmaceutical composition of claim 10, wherein said cell is an effector cell or a target cell.

12. The pharmaceutical composition of claim 10, further comprising a second antibody covalently attached to a second oligoribonucleotide through a second chemical linker and a pharmaceutically acceptable excipient.

* * * * *